United States Patent
De Waal Malefyt et al.

(10) Patent No.: US 11,045,547 B2
(45) Date of Patent: Jun. 29, 2021

(54) ANTI-LAG3 ANTIBODIES AND ANTIGEN-BINDING FRAGMENTS

(71) Applicant: Merck Sharp & Dohme Corp., Rahway, NJ (US)

(72) Inventors: Rene De Waal Malefyt, Sunnyvale, CA (US); Laurence Fayadat-Dilman, Sunnyvale, CA (US); Linda Liang, Mountain View, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 95 days.

(21) Appl. No.: 16/062,355

(22) PCT Filed: Dec. 13, 2016

(86) PCT No.: PCT/US2016/066266
§ 371 (c)(1),
(2) Date: Jun. 14, 2018

(87) PCT Pub. No.: WO2017/106129
PCT Pub. Date: Jun. 22, 2017

(65) Prior Publication Data
US 2018/0369375 A1   Dec. 27, 2018

Related U.S. Application Data

(60) Provisional application No. 62/268,070, filed on Dec. 16, 2015.

(51) Int. Cl.
| | |
|---|---|
| *A61K 39/395* | (2006.01) |
| *C07K 16/28* | (2006.01) |
| *A61K 39/00* | (2006.01) |
| *A61P 35/00* | (2006.01) |
| *A61K 31/195* | (2006.01) |
| *A61K 31/365* | (2006.01) |
| *A61K 31/575* | (2006.01) |
| *A61K 38/00* | (2006.01) |
| *A61K 45/06* | (2006.01) |

(52) U.S. Cl.
CPC ...... *A61K 39/39558* (2013.01); *A61K 31/195* (2013.01); *A61K 31/365* (2013.01); *A61K 31/575* (2013.01); *A61K 39/00* (2013.01); *A61P 35/00* (2018.01); *C07K 16/2803* (2013.01); *C07K 16/2878* (2013.01); *A61K 38/00* (2013.01); *A61K 45/06* (2013.01); *A61K 2039/505* (2013.01); *A61K 2300/00* (2013.01); *C07K 2317/24* (2013.01); *C07K 2317/33* (2013.01); *C07K 2317/76* (2013.01); *C07K 2317/92* (2013.01); *C07K 2317/94* (2013.01)

(58) Field of Classification Search
CPC ............ C07K 2317/50; C07K 2317/56; C07K 2317/565; A61K 2039/505
USPC ..................................................... 424/133.1
See application file for complete search history.

(56) References Cited

U.S. PATENT DOCUMENTS

| | | |
|---|---|---|
| 5,773,578 A | 6/1998 | Hercend et al. |
| 5,874,250 A | 2/1999 | Hercend et al. |
| 5,955,300 A | 9/1999 | Faure et al. |
| 5,976,877 A | 11/1999 | Hercend et al. |
| 6,143,273 A | 11/2000 | Faure et al. |
| RE38,313 E | 11/2003 | Faure et al. |
| 2003/0040044 A1 | 2/2003 | Heavner et al. |
| 2011/0070238 A1 | 3/2011 | Triebel |
| 2011/0293605 A1 | 12/2011 | Sathish et al. |
| 2014/0127226 A1 | 5/2014 | Pardoll et al. |
| 2015/0259420 A1 | 9/2015 | Triebel et al. |
| 2015/0307609 A1 | 10/2015 | Lonberg et al. |
| 2017/0022273 A1 | 1/2017 | Zhou et al. |

FOREIGN PATENT DOCUMENTS

| | | |
|---|---|---|
| EP | 0510079 B1 | 7/1991 |
| EP | 0758383 B1 | 11/1995 |
| EP | 1897548 B1 | 3/2008 |
| EP | 2044949 A1 | 4/2009 |
| EP | 2320940 B1 | 5/2011 |
| EP | 2659893 A3 | 2/2014 |
| EP | 2792365 A1 | 10/2014 |
| WO | WO199110682 A1 | 7/1991 |
| WO | WO199530750 A2 | 11/1995 |
| WO | WO199823741 A1 | 6/1996 |
| WO | WO199703695 A1 | 2/1997 |
| WO | WO1998023748 A1 | 6/1998 |

(Continued)

OTHER PUBLICATIONS

Bauche0 et al., (2018, Immunity 49, 342-352).*
Baixeras et al., Characterization of the Lymphocyte Activation Gene3-Encoded Protein a New Ligand for Human Leukocyte Antigen Class II Antigens, J. Exp. Med, 1992, 327-337, 176.
Bruniquel et al., Regulation of Expression of the Human Lymphocyte Activation Gene-3 LAG-3 Molecule, Immunogenetics, 1998, Section 2, pp. 116-124, 48.

(Continued)

*Primary Examiner* — Lynn A Bristol
(74) *Attorney, Agent, or Firm* — Li Su; Anna L. Cocuzzo

(57) ABSTRACT

The present invention includes antibodies and antigen-binding fragments thereof that specifically bind to human or cynomolgous monkey LAG3 as well as immunoglobulin chains thereof and polynucleotides encoding the same along with injection devices comprising such antibodies or fragments. Vaccines including such antibodies and fragments as well as compositions comprising the antibodies and fragments (e.g., including anti-PD1 antibodies) are included in the invention. Methods for treating or preventing cancer or infection using such compositions are also provided. In addition, methods for recombinant expression of the antibodies and fragments are part of the present invention.

18 Claims, 4 Drawing Sheets
Specification includes a Sequence Listing.

(56) References Cited

FOREIGN PATENT DOCUMENTS

| WO | WO1998058059 A1 | 12/1998 |
|---|---|---|
| WO | WO2003031655 A1 | 4/2003 |
| WO | 2004078928 A2 | 9/2004 |
| WO | 2006104389 A1 | 10/2006 |
| WO | WO2008132601 A1 | 11/2008 |
| WO | 2010019570 A2 | 2/2010 |
| WO | WO2011109789 A2 | 9/2011 |
| WO | 2012177624 A2 | 12/2012 |
| WO | 2013003761 A1 | 1/2013 |
| WO | WO2013066761 A1 | 5/2013 |
| WO | WO2013079945 A1 | 6/2013 |
| WO | WO2013192215 A1 | 12/2013 |
| WO | 201408218 A1 | 1/2014 |
| WO | 2014030049 A2 | 2/2014 |
| WO | WO2014028560 A2 | 2/2014 |
| WO | WO2014030052 A2 | 2/2014 |
| WO | 2014140180 A1 | 9/2014 |
| WO | WO2014144791 A2 | 9/2014 |
| WO | WO2014163684 A1 | 10/2014 |
| WO | WO2014179664 A2 | 11/2014 |
| WO | WO2014209804 A1 | 12/2014 |
| WO | WO201516718 A1 | 2/2015 |
| WO | 2015042246 A1 | 3/2015 |
| WO | WO2015048312 A1 | 4/2015 |
| WO | WO2015069571 A1 | 5/2015 |
| WO | WO2015069770 A1 | 5/2015 |
| WO | WO2015085210 A1 | 6/2015 |
| WO | WO2015091970 A1 | 6/2015 |
| WO | WO2015092382 A1 | 6/2015 |
| WO | WO2015112534 A2 | 7/2015 |
| WO | WO2015116539 A1 | 8/2015 |
| WO | 2015138920 A1 | 9/2015 |
| WO | 2015200119 A1 | 12/2015 |
| WO | WO2015200828 A1 | 12/2015 |
| WO | WO2016028672 A1 | 2/2016 |
| WO | WO2016123285 A1 | 8/2016 |
| WO | WO2016126858 A2 | 8/2016 |
| WO | 2016168716 A1 | 10/2016 |
| WO | 2016200782 A1 | 12/2016 |
| WO | WO2017019894 A1 | 2/2017 |

OTHER PUBLICATIONS

Creg J. Workman et al., LAG-3 Regulates Plasmacytoid Dendritic Cell Homeostasis, The Journal of Immunology, 2009, 1885-1891, 182.
Demeure et al., Role of LAG-3/MHC Class II Interactions in Cell-Cell Contacts, Eur. J. Cancer, 2001, Issue 13, pp. 1709-1718, 37.
Freeman & Sharpe, A new therapeutic strategy for malaria: targeting T cell Exhaustion, Nat. Immunol., 2012, 113-115, 13(2).
Grosso et al., LAG-3 Regulates CD8+ T Cell Accumulation and Effector Function in Murine Self-and Tumor-Tolerance Systems, J. Clin. Invest., 2007, Section 11, pp. 3383-3392, 117.
Hannier et al., CD3/TCR Complex-Associated Lymphocyte Activation Gene-3 Molecules Inhibit CD3/TCR Signaling, J. Immunol., 1998, 4058-4065, 161.
Huard et al., Cellular expression and tissue distribution of the human LAG-3-encoded protein, an MHC class II ligand, Immunogenetics, 1994, 213-217, 39.
Huard et al., Characterization of the major histocompatibility complex class II binding site on LAG-3 protein, Proc. Nat. Acad. Sci. USA, 1997, 5744-5749, 94.
Huard et al., T Cell Major Histocompatibility, Eur. J. Immunol., 1996, Issue 5, pp. 1180-1186, 26.
Huard, B et al., Lymphocyte-activation gene 3/major histocompatibility complex class II interaction modulates the antigenic response of CD4+ T lymphocytes, Eur. J. Immunol., 1994, pp. 3216-3221, 24.
International Search Report of PCT/US2015/045481 dated Oct. 9, 2015, 14 pages.
Malgorzata Kisielow et al., Expression of lymphocyte activation gene 3 (LAG-3) on B cells is induced by T cells, European Journal of Immunology, 2005, 2081-2088, 35.
Miyazaki et al., LAG-3 T Helper Cells in CD4 Deficient Mice, Int. Immunol., 1996, Issue 5, pp. 725-729, 8.
Pardoll & Drake, Immunotherapy earns its spot in the ranks of cancer therapy, J. Exp. Med., 2012, 201-209, 209 (2).
Phan et al., PNAS Cancer Regression and Autoimmunity Induced by Cytotoxic T Lymphocyte associated antigen for Blockade, Patients with Metastic Melanoma, 2003, pp. 8372-8377, NA.
S.-R. Woo et al., Immune Inhibitory Molecules LAG-3 and PD-1 Synergistically Regulate T-Cell Function to Promote Tumoral Immune Escape, Cancer Research, Dec. 20, 2011, 917-927, 72-4.
Shawn D. Blackburn et al., Coregulation of CD8+ T cell exhaustion by multiple inhibitory receptors during chronic viral infection, Nature Immunology, Jan. 2009, 29-37, 10-1.
Sierro et al., The CD4 like Molecule LAG-3, Expert Opin. Ther. Targets, 2011, Section 1, pp. 91-101, 15.
Susanne Andreae et al., Maturation and Activation of Dendritic Cells Induced by Lymphocyte Activation Gene-3 (CD223), The Journal of Immunology, 2002, 3874-3880, 168.
Triebel et al., LAG-3 A Novel Lymphocyte Activation Gene, J. Exp. Med., 1990, Issue 5, pp. 1393-1405, 171.
Triebel et al., LAG-3 A Regulator of T-cell and CD Responses, Trends Immunol., 2003, Issue 12, pp. 619-622, 24.
Workman et al., LAG-3 CD223 Regulates the Expansion of Activated T Cells, Eur. J. Immunol., 2003, pp. 970-979, 33.
Workman et al., Phenotypic Analysis of the Murine CD-4 Related Glycoprotein, Eur. J. Immunol., 2002, pp. 2255-2263, 32.
Cemerski, Saso, T cell activation and anti-tumor efficacy of anti-LAG-3 antibodies is independent of LAG-3—MHCII blocking capacity, Journal for ImmunoTherapy of Cancer, 2015, 183, vol. 3, Suppl. 2.
Yamane-Ohnuki, Naoko, Production of therapeutic antibodies with controlled fucosylation, mAbs, 2009, 230-236, vol. 1, No. 3.
Diamond, B et al., Somatic mutation of the T15 heavy chain gives rise to an antibody with autoantibody specificity, Proc. Natl. Acad., 1984, pp. 5841-5844, 81.
Ohno, S et al., Antigen-binding specificities of antibodies are primarily determined by seven residues of Vh, Proc. Natl. Acad., 1985, pp. 2945-2949, 82.
Rudikoff, S et al., Single amino acid substitution altering antigen-binding specificity, PNAS, 1982, pp. 1979-1983, 79.
Studnicka, Gary M. et al., Human-engineered monoclonal antibodies retain full specific binding activity by preserving non-CDR complementaritymodulating residues, Protein Engineering, 1994, 805-814, 7(6).
Yarilin, A.A., Osnovy Immunologii, M.: Medicine, 1999, 172-174, N/A.

\* cited by examiner

Sequences of Adimab anti LAG3 clones

Anti-human Lag3 from Adimab ADI-12126

Human x [LAG3_H] mAb (ADI-12126 Q1E <u>M57G</u> M115L) IgG4 S228P / Kappa

Heavy chain
EVQLVQSGAEVKKPGASVKVSCKASGYTFTGYYMHWVRQAPGQGLEWMGWINANSGgTNYAQKFQG
RVTMTRDTSISTAYMELSRLRSDDTAVYYCARDIYDSSDQLNVWGQGTIVTVSSASTKGPSVFPLAPCS
RSTSESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK Nucleotide sequence
ATGGAGTGGAGCTGGGTCTTCCTGTTCTTTCTGTCCGTCACAACCGGCGTGCACTCCGAGGTCCAGCTGGTGCAGTC
CGGCG
CTGAGGTGAAGAAACCCGGCGCTTCCGTGAAAGTGAGCTGCAAAGCCTCCGGATACACCTTCACCGGCTACTACATG
CACTGGGTGAGGCAGGCCCC
TGGACAGGGACTGGAGTGGATGGGCTGGATCAACGCCAACAGCGGAGGCACCAACTACGCCCAGAAGTTCCAGGGCA
GAGTCACCATGACAAGGGAT
ACCTCCATCAGCACCGCCTACATGGAGCTGAGCAGGCTGAGAAGCGACGATACAGCCGTCTACTACTGCGCCAGGGA
TATCTACGACTCCAGCGACC
AGCTGAATGTGTGGGGCCAGGGCACACTGGTGACCGTGAGCAGCGCCTCCACCAAGGGCCCTAGCGTGTTCCCTCTG
GCCCCTTGCTCCAGATCCAC
ATCCGAATCCACAGCCGCCCTGGGCTGCCTGGTGAAGGACTATTTCCCCGAGCCCGTGACCGTGTCCTGGAACTCCG
GAGCCCTGACCAGCGGAGTG
CATACCTTCCCCGCCGTGCTGCAGTCCTCCGGACTGTACTCCCTGAGCAGCGTGGTCACCGTGCCCAGCAGCAGCCT
GGGCACCAAGACCTATACAT
GTAACGTGGACCACAAGCCCAGCAACACCAAGGTGGACAAGAGGGTGGAGAGCAAGTACGGACCCCCTTGCCCCCCC
TGTCCCGCCCCCGAGTTCCT
GGGAGGCCCCTCCGTGTTTCTGTTCCCCCCTAAACCCAAGGACACCCTGATGATCTCCAGGACACCCGAAGTGACCT
GTGTGGTGGTGGACGTGTCC
CAGGAAGATCCTGAGGTGCAGTTCAATTGGTACGTCGACGGCGTGGAGGTGCACAATGCCAAGACCAAGCCTAGGGA
GGAGCAGTTCAACTCCACCT
ATAGGGTGGTGAGCGTGCTGACAGTGCTGCACCAAGATTGGCTGAACGGAAAGGAATACAAGTGCAAGGTGTCCAAC
AAGGGCCTGCCTAGCAGCAT
CGAGAAAACCATCTCCAAAGCTAAGGGCCAGCCCAGAGAACCTCAAGTGTACACCCTGCCCCCCTCCCAGGAAGAGA
TGACCAAGAACCAGGTGAGC
CTCACCTGTCTGGTGAAGGGATTCTACCCCAGCGACATTGCCGTGGAGTGGGAATCCAATGGCCAGCCTGAGAACAA
TTACAAGACCACACCCCCCG
TGCTGGACAGCGATGGCAGCTTCTTTCTGTACTCCAGGCTGACCGTGGACAAGAGCAGGTGGCAGGAGGGCAATGTG
TTCTCCTGCAGCGTGATGCA
TGAGGCCCTCCACAATCACTACACCCAGAAGTCCCTGTCCCTCAGCCTCGGAAAATGA

FIG.2A

Light chain
EIVLTQSPATLSLSPGERATLSCRASQSVSSYLAWYQQKPGQAPRLLIYDASNRATGIPARFSGSGSGTD
FTLTISSLEPEDFAVYYCQQASIWPLTFGGGTKVEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSF
NRGEC Nucleotide sequence
ATGTCCGTGCCCACCCAGGTGCTGGGACTGCTGCTGCTGTGGCTGACCGACGCCCGGTGTGAGATC
GTGCTGACCCAGTCCCCCGCTACCCTGAGCCTGTCCCCTGGAGAGAGGGCTACCCTGTCCTGTAGG
GCCTCCCAGTCCGTGAGCTCCTACCTGGCCTGGTACCAGCAGAAACCCGGCCAGGCTCCTAGGCTG
CTGATCTACGACGCCTCCAATAGGGCCACCGGCATTCCCGCTAGGTTCTCCGGAAGCGGCTCCGGC
ACCGACTTCACCCTGACCATCTCCAGCCTGGAGCCCGAGGACTTCGCTGTGTACTACTGCCAGCAGG
CCAGCATCTGGCCCCTGACCTTCGGAGGCGGCACCAAGGTGGAGATCAAGAGGACCGTGGCCGCC
CCTTCCGTGTTCATCTTCCCCCCCTCCGATGAGCAGCTGAAGAGCGGCACCGCCAGCGTGGTGTGC
CTGCTGAACAACTTCTACCCCAGGGAGGCCAAGGTGCAGTGGAAGGTGGACAACGCCCTGCAGAGC
GGCAACTCCCAGGAGTCCGTGACAGAGCAGGACAGCAAGGACTCCACCTACAGCCTGAGCTCCACC
CTGACCCTGAGCAAGGCCGACTACGAAAAGCACAAGGTGTACGCCTGTGAGGTGACCCACCAGGGC
CTGTCCTCCCCTGTGACCAAGTCCTTTAACAGGGGCGAGTGCTGA ADI-12152 (anti-human LAG3)

Heavy chain
QVQLVQSGAEVKKPGASVKVSCKASGYTFQGYYMHWVRQAPGQGLEWMGQINPHSGGTNYAQKFQG
RVTMTRDTSISTAYMELSRLRSDDTAVYYCARDRGEFDIAFDIWGQGTMVTVSSASTKGPSVFPLAPCS
RSTSESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK Nucleotide sequence
ATGGAGTGGAGCTGGGTGTTCCTGTTTTTCCTGAGCGTCACCACAGGCGTGCACTCCCAGGTCCAG
CTGGTGCAGTCCGGAGCTGAGGTGAAGAAGCCTGGAGCCTCCGTGAAGGTGTCCTGCAAGGCCTCC
GGCTACACCTTCCAGGGCTATTACATGCACTGGGTGAGGCAGGCTCCTGGACAGGGACTGGAGTGG
ATGGGCCAGATTAATCCCCACAGCGGAGGCACCAACTACGCCCAGAAGTTCCAGGGCCGGGTGACA
ATGACACGGGACACCTCCATCAGCACAGCTTACATGGAGCTGTCCAGGCTCAGGTCCGACGACACC
GCCGTGTACTACTGCGCTCGGGATCGGGGAGAGTTTGACATCGCCTTCGACATCTGGGGCCAGGGC
ACAATGGTGACAGTGAGCTCCGCCTCCACCAAGGGCCCTTCCGTGTTTCCCCTCGCCCCCTGTAGCA
GGTCCACATCCGAGTCCACAGCTGCCCTGGGCTGTCTGGTGAAGGATTACTTCCCTGAGCCTGTGAC
AGTGAGCTGGAACAGCGGCGCTCTGACCTCCGGCGTGCATACCTTTCCCGCCGTGCTGCAGTCCAG
CGGACTGTACAGCCTGAGCTCCGTGGTGACAGTCCCCTCCTCCTCCCTGGGCACCAAAACCTACACC

FIG.2B

TGTAACGTGGACCACAAGCCCAGCAACACCAAGGTGGACAAGAGGGTGGAATCCAAGTACGGCCCT
CCTTGTCCTCCTTGCCCCGCTCCCGAGTTTCTGGGCGGACCTTCCGTGTTCCTGTTCCCTCCCAAGC
CCAAGGACACACTCATGATTAGCAGGACCCCCGAGGTCACATGTGTGGTGGTGGACGTGAGCCAGG
AGGACCCCGAGGTCCAGTTCAACTGGTACGTGGATGGCGTGGAGGTGCACAACGCTAAAACAAAGC
CCCGGGAAGAACAGTTCAACAGCACCTATCGGGTGGTGTCCGTGCTGACCGTGCTGCACCAGGACT
GGCTGAATGGCAAGGAGTACAAGTGCAAAGTCAGCAACAAGGGCCTGCCTTCCAGCATCGAGAAGA
CCATCAGCAAGGCTAAGGGCCAGCCCAGGGAGCCTCAGGTCTACACCCTCCCCCCTTCCCAGGAGG
AGATGACAAAGAACCAGGTGTCCCTCACCTGCCTGGTGAAGGGCTTCTACCCCAGCGACATCGCCG
TGGAATGGGAGTCCAACGGCCAGCCCGAGAATAACTACAAGACCACACCTCCTGTGCTGGATTCCG
ATGGCAGCTTCTTTCTGTACTCCAGGCTGACCGTGGATAAGTCCCGGTGGCAGGAGGGCAACGTCT
TTAGCTGCAGCGTGATGCATGAGGCTCTGCACAATCACTACACCCAGAAAAGCCTCAGCCTGTCCCT
GGGCAAATGA

Light chain
DIQMTQSPSSLSASVGDRVTITCQASQDITNYLNWYQQKPGKAPKLLIYDASNLETGVPSRFSGSGSGT
DFTFTISSLQPEDIATYYCQQVPPEPPYTFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKS
FNRGEC Nucleotide sequence
ATGTCCGTGCCCACCCAGGTGCTGGGACTGCTCCTGCTGTGGCTCACAGACGCCAGGTGCGACATC
CAGATGACCCAGTCCCCCTCCTCCCTGTCCGCTTCCGTGGGCGACAGGGTGACCATTACCTGCCAG
GCCTCCCAGGACATCACCAACTATCTGAACTGGTACCAGCAGAAGCCCGGCAAGGCCCCCAAACTG
CTGATCTACGACGCCTCCAACCTGGAGACCGGCGTGCCTTCCAGGTTCTCCGGAAGCGGCAGCGGC
ACCGACTTCACCTTCACCATCTCCAGCCTGCAGCCCGAGGACATCGCCACCTACTACTGCCAGCAGG
TGCCTCCTGAGCCCCCTACACCTTCGGAGGAGGCACCAAGGTGGAGATCAAGCGGACAGTGGCTG
CTCCCTCCGTCTTCATCTTCCCCCCCTCCGACGAGCAGCTGAAGAGCGGAACAGCCTCCGTGGTGTG
CCTCCTGAACAACTTCTACCCCCGGGAGGCCAAAGTGCAGTGGAAGGTGGACAATGCCCTGCAGAG
CGGCAACTCCCAGGAGTCCGTCACCGAGCAGGACAGCAAGGATTCCACCTACAGCCTGTCCTCCAC
CCTGACCCTGTCCAAGGCCGATTACGAGAAGCACAAGGTGTACGCCTGCGAGGTGACCCACCAGGG
ACTGTCCTCCCCCGTGACCAAGTCCTTCAACCGGGGCGAGTGCTGA

FIG.2C

SEQUENCE LISTING

```
<160> NUMBER OF SEQ ID NOS: 54

<210> SEQ ID NO 1
<211> LENGTH: 120
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Q or E
<220> FEATURE:
<221> NAME/KEY: MISC_FEATURE
<222> LOCATION: (57)..(57)
<223> OTHER INFORMATION: Xaa = M, G, L, S, T, Y, V or A
<220> FEATURE:
<221> NAME/KEY: MISC_FEATURE
<222> LOCATION: (115)..(115)
<223> OTHER INFORMATION: Xaa = M or L

<400> SEQUENCE: 1

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Ala Asn Ser Gly Xaa Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ile Tyr Asp Ser Ser Asp Gln Leu Asn Val Trp Gly Gln
            100                 105                 110

Gly Thr Xaa Val Thr Val Ser Ser
        115                 120

<210> SEQ ID NO 2
<211> LENGTH: 107
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ala Ser Ile Trp Pro Leu
                 85                  90                  95

Thr Phe Gly Gly Gly Thr Lys Val Glu Ile Lys
            100                 105

<210> SEQ ID NO 3
<211> LENGTH: 120
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Gln Gly Tyr
                20                  25                  30

Tyr Met His Trp Val Arg Gln Ala Pro Gly Gln Gly Leu Glu Trp Met
             35                  40                  45

Gly Gln Ile Asn Pro His Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Arg Gly Glu Phe Asp Ile Ala Phe Asp Ile Trp Gly Gln
            100                 105                 110

Gly Thr Met Val Thr Val Ser Ser
        115                 120

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Thr Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Val Pro Pro Glu Pro Pro
                 85                  90                  95

Tyr Thr Phe Gly Gly Gly Thr Lys Val Glu Ile Lys
            100                 105

<210> SEQ ID NO 5
<211> LENGTH: 10
<212> TYPE: PRT
<213> ORGANISM: Homo sapiens

<400> SEQUENCE: 5

Gly Tyr Thr Phe Thr Gly Tyr Tyr Met His

<210> SEQ ID NO 6
<211> LENGTH: 17
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa = M, G, L, S, T, Y, V or A

<400> SEQUENCE: 6

Trp Ile Asn Ala Asn Ser Gly Xaa Thr Asn Tyr Ala Gln Lys Phe Gln
1               5                   10                  15

Gly

<210> SEQ ID NO 7
<211> LENGTH: 11
<212> TYPE: PRT
<213> ORGANISM: Homo sapiens

<400> SEQUENCE: 7

Asp Ile Tyr Asp Ser Ser Asp Gln Leu Asn Val
1               5                   10

<210> SEQ ID NO 8
<211> LENGTH: 11
<212> TYPE: PRT
<213> ORGANISM: Homo sapiens

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Homo sapiens

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Homo sapiens

<400> SEQUENCE: 10

Gln Gln Ala Ser Ile Trp Pro Leu Thr
1               5

<210> SEQ ID NO 11
<211> LENGTH: 10
<212> TYPE: PRT
<213> ORGANISM: Homo sapiens

<400> SEQUENCE: 11

Gly Tyr Thr Phe Gln Gly Tyr Tyr Met His
1               5                   10

<210> SEQ ID NO 12
<211> LENGTH: 17
<212> TYPE: PRT
<213> ORGANISM: Homo sapiens

<400> SEQUENCE: 12

Gln Ile Asn Pro His Ser Gly Gly Thr Asn Tyr Ala Gln Lys Phe Gln
1               5                   10                  15

Gly

<210> SEQ ID NO 13
<211> LENGTH: 11
<212> TYPE: PRT
<213> ORGANISM: Homo sapiens

<400> SEQUENCE: 13

Asp Arg Gly Glu Phe Asp Ile Ala Phe Asp Ile
1               5                   10

<210> SEQ ID NO 14
<211> LENGTH: 11
<212> TYPE: PRT
<213> ORGANISM: Homo sapiens

<400> SEQUENCE: 14

Gln Ala Ser Gln Asp Ile Thr Asn Tyr Leu Asn
1               5                   10

<210> SEQ ID NO 15
<211> LENGTH: 7
<212> TYPE: PRT
<213> ORGANISM: Homo sapiens

<400> SEQUENCE: 15

Asp Ala Ser Asn Leu Glu Thr
1               5

<210> SEQ ID NO 16
<211> LENGTH: 10
<212> TYPE: PRT
<213> ORGANISM: Homo sapiens

<400> SEQUENCE: 16

Gln Gln Val Pro Pro Glu Pro Pro Tyr Thr
1               5                   10

<210> SEQ ID NO 17
<211> LENGTH: 1401
<212> TYPE: DNA
<213> ORGANISM: Homo sapiens

<400> SEQUENCE: 17

```
atggaatgga gctgggtgtt tctgttcttc ctgtccgtga caaccggcgt gcactcccag      60
gtgcagctgg tgcagtccgg cgctgaggtc aagaaacctg gcgccagcgt caaagtgagc     120
tgtaaggcct ccggctacac ctttaccgga tactacatgc actgggtcag gcaggcccct     180
ggacagggac tggaatggat gggctggatc aacgctaaca gcggaatgac caactacgcc     240
cagaagttcc agggccgggt gacaatgacc cgggacacct ccatcagcac cgcctacatg     300
gagctgtccc ggctgaggtc cgatgacacc gctgtgtact actgcgcccg ggacatctat     360
gactcctccg accagctgaa cgtgtggggc cagggcacaa tggtgacagt gagctccgct     420
tccaccaagg gcccagcgt gtttcccctg gctccctgca gcaggagcac atccgagtcc     480
accgctgccc tgggctgtct ggtgaaggac tactttcctg agcctgtgac cgtgtcctgg     540
aatagcggcg ccctgacaag cggagtgcac acattccccg ctgtgctcca atcctccgga    600
```

```
ctgtacagcc tgagctccgt cgtgacagtg cccagcagca gcctgggcac caagacctac    660
acctgcaacg tggaccacaa gccttccaac accaaggtgg acaagagggt ggagagcaag    720
tacggccccc cttgtcctcc ttgtcctgcc cctgagttcc tcggaggacc cagcgtgttc    780
ctgtttcctc ctaaacccaa ggacaccctg atgatctccc ggacacccga agtgacatgt    840
gtggtggtgg acgtgtccca ggaagacccc gaggtgcagt tcaactggta cgtggatggc    900
gtggaagtgc ataacgctaa gaccaagccc cgggaagagc agttcaacag cacctacagg    960
gtggtgtccg tgctgacagt gctgcaccag gactggctga atggcaaaga gtacaagtgc   1020
aaggtcagca acaagggcct gcctcctcc atcgagaaga ccatcagcaa ggccaaggga   1080
cagcctcggg agcctcaggt gtacaccctg ccccctccc aggaggagat gaccaagaac   1140
caggtcagcc tgacctgcct ggtgaagggc ttctacccct ccgacatcgc cgtcgagtgg   1200
gagtccaacg gccagcctga gaataactac aagaccaccc ccctgtcct ggacagcgac   1260 ggttctttct cctgtacag caggctgaca gtggacaagt ccaggtggca ggagggcaac   1320
gtgttctcct gctccgtgat gcacgaagcc ctgcacaatc actatacca gaagtccctc   1380 agcctgtccc tcggcaaatg a                                            1401

<210> SEQ ID NO 18
<211> LENGTH: 705
<212> TYPE: DNA
<213> ORGANISM: Homo sapiens

<400> SEQUENCE: 18
atgtccgtgc ccacccaggt gctgggactg ctgctgctgt ggctgaccga cgcccggtgt     60
gagatcgtgc tgacccagtc ccccgctacc ctgagcctgt cccctggaga gagggctacc    120
ctgtcctgta gggcctccca gtccgtgagc tcctacctgg cctggtacca gcagaaaccc    180
ggccaggctc ctaggctgct gatctacgac gcctccaata gggccaccgg cattcccgct    240
aggttctccg gaagcggctc cggcaccgac ttcaccctga ccatctccag cctggagccc    300
gaggacttcg ctgtgtacta ctgccagcag gccagcatct ggcccctgac cttcggaggc    360
ggcaccaagg tggagatcaa agaggaccgt ggccgcccctt ccgtgttcat cttccccccc    420
tccgatgagc agctgaagag cggcaccgcc agcgtggtgt gcctgctgaa caacttctac    480
cccagggagg ccaaggtgca gtggaaggtg gacaacgccc tgcagagcgg caactcccag    540
gagtccgtga cagagcagga cagcaaggac tccacctaca gcctgagctc caccctgacc    600
ctgagcaagg ccgactacga aaagcacaag gtgtacgcct gtgaggtgac ccaccagggc    660
ctgtcctccc ctgtgaccaa gtccttaac aggggcgagt gctga                    705

<210> SEQ ID NO 19
<211> LENGTH: 1401
<212> TYPE: DNA
<213> ORGANISM: Homo sapiens

<400> SEQUENCE: 19
atggagtgga gctgggtgtt cctgtttttc ctgagcgtca ccacaggcgt gcactcccag     60
gtccagctgt gcagtccgg agctgaggtg aagaagcctg gagcctccgt gaaggtgtcc    120
tgcaaggcct ccggctacac cttccagggc tattacatgc actgggtgag gcaggctcct    180
ggacagggac tggagtggat gggccagatt aatccccaca gcggaggcac caactacgcc    240
cagaagttcc agggccgggt gacaatgaca cgggacacct ccatcagcac agcttacatg    300
```

-continued

```
gagctgtcca ggctcaggtc cgacgacacc gccgtgtact actgcgctcg ggatcgggga    360
gagtttgaca tcgccttcga catctggggc cagggcacaa tggtgacagt gagctccgcc    420
tccaccaagg gcccttccgt gtttcccctc gcccctgta gcaggtccac atccgagtcc     480
acagctgccc tgggctgtct ggtgaaggat tacttccctg agcctgtgac agtgagctgg    540
aacagcggcg ctctgacctc cggcgtgcat acctttcccg ccgtgctgca gtccagcgga    600
ctgtacagcc tgagctccgt ggtgacagtc cctcctcct ccctgggcac caaaacctac     660
acctgtaacg tggaccacaa gcccagcaac accaaggtgg acaagagggt ggaatccaag    720
tacgcccctc cttgtcctcc ttgccccgct cccgagtttc tgggcggacc ttccgtgttc    780
ctgttccctc ccaagcccaa ggacacactc atgattagca ggaccccga ggtcacatgt     840 gtggtggtgg acgtgagcca ggaggacccc gaggtccagt tcaactggta cgtggatggc    900
gtggaggtgc acaacgctaa acaaagccc cgggaagaac agttcaacag cacctatcgg     960
gtggtgtccg tgctgaccgt gctgcaccag gactggctga atggcaagga gtacaagtgc    1020
aaagtcagca caagggcct gccttccagc atcgagaaga ccatcagcaa ggctaagggc     1080
cagcccaggg agcctcaggt ctacaccctc ccccttccc aggaggagat gacaaagaac      1140
caggtgtccc tcacctgcct ggtgaagggc ttctacccca cgacatcgc cgtggaatgg     1200 gagtccaacg gccagcccga gaataactac aagaccacac tcctgtgct ggattccgat      1260 ggcagcttct ttctgtactc caggctgacc gtggataagt cccggtggca ggagggcaac    1320
gtctttagct gcagcgtgat gcatgaggct ctgcacaatc actacaccca gaaaagcctc    1380
agcctgtccc tgggcaaatg a                                              1401
```

<210> SEQ ID NO 20
<211> LENGTH: 708
<212> TYPE: DNA
<213> ORGANISM: Homo sapiens

<400> SEQUENCE: 20

```
atgtccgtgc ccacccaggt gctgggactg ctcctgctgt ggctcacaga cgccaggtgc    60
gacatccaga tgacccagtc cccctcctcc ctgtccgctt ccgtgggcga cagggtgacc    120
attacctgcc aggcctccca ggacatcacc aactatctga actggtacca gcagaagccc    180
ggcaaggccc ccaaactgct gatctacgac gcctccaacc tggagaccgg cgtgccttcc    240
aggttctccg gaagcggcag cggcaccgac ttcaccttca ccatctccag cctgcagccc    300
gaggacatcg ccacctacta ctgccagcag gtgcctcctg agccccccta caccttcgga    360
ggaggcacca aggtggagat caagcggaca gtggctgctc cctccgtctt catcttcccc    420 cctccgacg agcagctgaa gagcggaaca gcctccgtgg tgtgcctcct gaacaacttc    480
tacccccggg aggccaaagt gcagtggaag gtggacaatg ccctgcagag cggcaactcc    540
caggagtccg tcaccgagca ggacagcaag gattccacct acagcctgtc ctccaccctg    600
accctgtcca aggccgatta cgagaagcac aaggtgtacg cctgcgaggt gacccaccag    660
ggactgtcct cccccgtgac caagtccttc aaccggggcg agtgctga                 708
```

<210> SEQ ID NO 21
<211> LENGTH: 447
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Q or E

```
<220> FEATURE:
<221> NAME/KEY: MISC_FEATURE
<222> LOCATION: (57)..(57)
<223> OTHER INFORMATION: Xaa = M, G, L, S, T, Y, V or A
<220> FEATURE:
<221> NAME/KEY: MISC_FEATURE
<222> LOCATION: (115)..(115)
<223> OTHER INFORMATION: Xaa = M or L

<400> SEQUENCE: 21
```

| | | | | | | | | | | | | | | |
|---|---|---|---|---|---|---|---|---|---|---|---|---|---|---|
| Xaa | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Gly | Tyr |
| | | | 20 | | | | | 25 | | | | | 30 | | |
| Tyr | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Asn | Ala | Asn | Ser | Gly | Xaa | Thr | Asn | Tyr | Ala | Gln | Lys | Phe |
| 50 | | | | | 55 | | | | | 60 | | | | | |
| Gln | Gly | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Arg | Asp | Ile | Tyr | Asp | Ser | Ser | Asp | Gln | Leu | Asn | Val | Trp | Gly | Gln |
| | | | 100 | | | | | 105 | | | | | 110 | | |
| Gly | Thr | Xaa | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Cys | Ser | Arg | Ser | Thr | Ser | Glu | Ser | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Lys | Thr | Tyr | Thr | Cys | Asn | Val | Asp | His | Lys |
| | | 195 | | | | | 200 | | | | | 205 | | | |
| Pro | Ser | Asn | Thr | Lys | Val | Asp | Lys | Arg | Val | Glu | Ser | Lys | Tyr | Gly | Pro |
| | 210 | | | | | 215 | | | | | 220 | | | | |
| Pro | Cys | Pro | Pro | Cys | Pro | Ala | Pro | Glu | Phe | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | Gln | Glu | Asp | Pro | Glu |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Phe | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Gln | Glu | Glu | Met | Thr | Lys | Asn | Gln | Val | Ser | Leu | Thr | Cys | Leu |
| | | 355 | | | | | 360 | | | | | 365 | | | |

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 22
<211> LENGTH: 214
<212> TYPE: PRT
<213> ORGANISM: Homo sapiens

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Ile Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 447
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gln Gly Tyr
            20                  25                  30

```
Tyr Met His Trp Val Arg Gln Ala Pro Gly Gln Gly Leu Glu Trp Met
        35                  40                  45
Gly Gln Ile Asn Pro His Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Thr Ala Val Tyr Tyr Cys
                85                  90                  95
Ala Arg Asp Arg Gly Glu Phe Asp Ile Ala Phe Asp Ile Trp Gly Gln
                100                 105                 110
Gly Thr Met Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445
```

<210> SEQ ID NO 24
<211> LENGTH: 215
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Pro Pro Glu Pro Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 25
<211> LENGTH: 11
<212> TYPE: PRT
<213> ORGANISM: Artificial Sequence
<220> FEATURE:
<223> OTHER INFORMATION: Anti-IL10 CDR

<400> SEQUENCE: 25

Lys Thr Ser Gln Asn Ile Phe Glu Asn Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: anti-IL10 CDR

<400> SEQUENCE: 26

Asn Ala Ser Pro Leu Gln Ala
1               5

<210> SEQ ID NO 27
<211> LENGTH: 8

```
<212> TYPE: PRT
<213> ORGANISM: Artificial Sequence
<220> FEATURE:
<223> OTHER INFORMATION: anti-IL10 CDR

<400> SEQUENCE: 27

His Gln Tyr Tyr Ser Gly Tyr Thr
1               5

<210> SEQ ID NO 28
<211> LENGTH: 10
<212> TYPE: PRT
<213> ORGANISM: Artificial Sequence
<220> FEATURE:
<223> OTHER INFORMATION: anti-IL10 CDR

<400> SEQUENCE: 28

Gly Phe Thr Phe Ser Asp Tyr His Met Ala
1               5                   10

<210> SEQ ID NO 29
<211> LENGTH: 17
<212> TYPE: PRT
<213> ORGANISM: Artificial Sequence
<220> FEATURE:
<223> OTHER INFORMATION: anti-IL10 CDR

<400> SEQUENCE: 29

Ser Ile Thr Leu Asp Ala Thr Tyr Thr Tyr Tyr Arg Asp Ser Val Arg
1               5                   10                  15

Gly

<210> SEQ ID NO 30
<211> LENGTH: 10
<212> TYPE: PRT
<213> ORGANISM: Artificial Sequence
<220> FEATURE:
<223> OTHER INFORMATION: anti-IL10 CDR

<400> SEQUENCE: 30

His Arg Gly Phe Ser Val Trp Leu Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: anti-TSLP CDR

<400> SEQUENCE: 31

Gly Tyr Ile Phe Thr Asp Tyr Ala Met His
1               5                   10

<210> SEQ ID NO 32
<211> LENGTH: 16
<212> TYPE: PRT
<213> ORGANISM: Artificial Sequence
<220> FEATURE:
<223> OTHER INFORMATION: anti-TSLP CDR

<400> SEQUENCE: 32

Thr Phe Ile Pro Leu Leu Asp Thr Ser Asp Tyr Asn Gln Asn Phe Lys
1               5                   10                  15

<210> SEQ ID NO 33
```

```
<211> LENGTH: 11
<212> TYPE: PRT
<213> ORGANISM: Artificial Sequence
<220> FEATURE:
<223> OTHER INFORMATION: anti-TSLP CDR

<400> SEQUENCE: 33

Met Gly Val Thr His Ser Tyr Val Met Asp Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: anti-TSLP CDR

<400> SEQUENCE: 34

Arg Ala Ser Gln Pro Ile Ser Ile Ser Val His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: anti-TSLP CDR

<400> SEQUENCE: 35

Phe Ala Ser Gln Ser Ile Ser
1               5

<210> SEQ ID NO 36
<211> LENGTH: 9
<212> TYPE: PRT
<213> ORGANISM: Artificial Sequence
<220> FEATURE:
<223> OTHER INFORMATION: anti-TSLP CDR

<400> SEQUENCE: 36

Gln Gln Thr Phe Ser Leu Pro Tyr Thr
1               5

<210> SEQ ID NO 37
<211> LENGTH: 10
<212> TYPE: PRT
<213> ORGANISM: Artificial Sequence
<220> FEATURE:
<223> OTHER INFORMATION: anti-CD27 CDR

<400> SEQUENCE: 37

Gly Phe Ile Ile Lys Ala Thr Tyr Met His
1               5                   10

<210> SEQ ID NO 38
<211> LENGTH: 17
<212> TYPE: PRT
<213> ORGANISM: Artificial Sequence
<220> FEATURE:
<223> OTHER INFORMATION: anti-CD27 CDR

<400> SEQUENCE: 38

Arg Ile Asp Pro Ala Asn Gly Glu Thr Lys Tyr Asp Pro Lys Phe Gln
1               5                   10                  15

Val
```

-continued

```
<210> SEQ ID NO 39
<211> LENGTH: 7
<212> TYPE: PRT
<213> ORGANISM: Artificial Sequence
<220> FEATURE:
<223> OTHER INFORMATION: anti-CD27 CDR

<400> SEQUENCE: 39

Tyr Ala Trp Tyr Phe Asp Val
1               5

<210> SEQ ID NO 40
<211> LENGTH: 11
<212> TYPE: PRT
<213> ORGANISM: Artificial Sequence
<220> FEATURE:
<223> OTHER INFORMATION: anti-CD27 CDR

<400> SEQUENCE: 40

Arg Ala Ser Glu Asn Ile Tyr Ser Phe Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: anti-CD27 CDR

<400> SEQUENCE: 41

His Ala Lys Thr Leu Ala Glu
1               5

<210> SEQ ID NO 42
<211> LENGTH: 9
<212> TYPE: PRT
<213> ORGANISM: Artificial Sequence
<220> FEATURE:
<223> OTHER INFORMATION: anti-CD27 CDR

<400> SEQUENCE: 42

Gln His Tyr Tyr Gly Ser Pro Leu Thr
1               5

<210> SEQ ID NO 43
<211> LENGTH: 447
<212> TYPE: PRT
<213> ORGANISM: Artificial Sequence
<220> FEATURE:
<223> OTHER INFORMATION: humanized mouse immunoglobulin

<400> SEQUENCE: 43

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95
```

-continued

```
Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 44
<211> LENGTH: 218
<212> TYPE: PRT
<213> ORGANISM: Artificial Sequence
<220> FEATURE:
<223> OTHER INFORMATION: humanized mouse immunoglobulin

<400> SEQUENCE: 44

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Lys Gly Val Thr Ser
             20                  25                  30

Gly Tyr Ser Tyr Leu His Trp Tyr Gln Gln Lys Pro Gly Gln Ala Pro
             35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 45
<211> LENGTH: 440
<212> TYPE: PRT
<213> ORGANISM: Artificial Sequence
<220> FEATURE:
<223> OTHER INFORMATION: immunoglobulin chain

<400> SEQUENCE: 45

Gln Val Gln Leu Val Glu Ser Gly Gly Val Val Gln Pro Gly Arg
 1               5                  10                  15

Ser Leu Arg Leu Asp Cys Lys Ala Ser Gly Ile Thr Phe Ser Asn Ser
             20                  25                  30

Gly Met His Trp Val Arg Gln Ala Pro Gly Lys Gly Leu Glu Trp Val
             35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Ser Gly Leu Tyr
            165                 170                 175
Ser Leu Ser Ser Val Val Thr Val Pro Ser Ser Ser Leu Gly Thr Lys
        180                 185                 190
Thr Tyr Thr Cys Asn Val Asp His Lys Pro Ser Asn Thr Lys Val Asp
        195                 200                 205
Lys Arg Val Glu Ser Lys Tyr Gly Pro Pro Cys Pro Pro Cys Pro Ala
210                 215                 220
Pro Glu Phe Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
            245                 250                 255
Val Asp Val Ser Gln Glu Asp Pro Glu Val Gln Phe Asn Trp Tyr Val
            260                 265                 270
Asp Gly Val Glu Val His Asn Ala Lys Thr Lys Pro Arg Glu Glu Gln
            275                 280                 285
Phe Asn Ser Thr Tyr Arg Val Val Ser Val Leu Thr Val Leu His Gln
        290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
            325                 330                 335
Arg Glu Pro Gln Val Tyr Thr Leu Pro Pro Ser Gln Glu Glu Met Thr
            340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
        370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
            405                 410                 415
Ser Cys Ser Val Met His Glu Ala Leu His Asn His Tyr Thr Gln Lys
            420                 425                 430
Ser Leu Ser Leu Ser Leu Gly Lys
        435                 440

<210> SEQ ID NO 46
<211> LENGTH: 214
<212> TYPE: PRT
<213> ORGANISM: Artificial Sequence
<220> FEATURE:
<223> OTHER INFORMATION: immunoglobulin chain

<400> SEQUENCE: 46

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 1401
<212> TYPE: DNA
<213> ORGANISM: Homo sapiens

<400> SEQUENCE: 47

| | | | | | |
|---|---|---|---|---|---|
| atggagtgga | gctgggtctt | cctgttcttt | ctgtccgtca | caaccggcgt | gcactccgag | 60 |
| gtccagctgg | tgcagtccgg | cgctgaggtg | aagaaacccg | gcgcttccgt | gaaagtgagc | 120 |
| tgcaaagcct | ccggatacac | cttcaccggc | tactacatgc | actgggtgag | gcaggcccct | 180 |
| ggacagggac | tggagtggat | gggctggatc | aacgccaaca | gcggaggcac | caactacgcc | 240 |
| cagaagttcc | agggcagagt | caccatgaca | agggatacct | ccatcagcac | cgcctacatg | 300 |
| gagctgagca | ggctgagaag | cgacgataca | gccgtctact | actgcgccag | ggatatctac | 360 |
| gactccagcg | accagctgaa | tgtgtggggc | cagggcacac | tggtgaccgt | gagcagcgcc | 420 |
| tccaccaagg | gccctagcgt | gttccctctg | gccccttgct | ccagatccac | atccgaatcc | 480 |
| acagccgccc | tgggctgcct | ggtgaaggac | tatttccccg | agcccgtgac | cgtgtcctgg | 540 |
| aactccggag | ccctgaccag | cggagtgcat | accttccccg | ccgtgctgca | gtcctccgga | 600 |
| ctgtactccc | tgagcagcgt | ggtcaccgtg | cccagcagca | gcctgggcac | caagacctat | 660 |
| acatgtaacg | tggaccacaa | gcccagcaac | accaaggtgg | acaagagggt | ggagagcaag | 720 |
| tacggacccc | cttgcccccc | ctgtcccgcc | ccgagttcc | tgggaggccc | ctccgtgttt | 780 |
| ctgttccccc | ctaaacccaa | ggacaccctg | atgatctcca | ggacaccga | agtgacctgt | 840 |
| gtggtggtgg | acgtgtccca | ggaagatcct | gaggtgcagt | tcaattggta | cgtcgacggc | 900 |
| gtggaggtgc | acaatgccaa | gaccaagcct | agggaggagc | agttcaactc | cacctatagg | 960 |
| gtggtgagcg | tgctgacagt | gctgcaccaa | gattggctga | acggaaagga | atacaagtgc | 1020 |
| aaggtgtcca | acaagggcct | gcctagcagc | atcgagaaaa | ccatctccaa | agctaagggc | 1080 |
| cagcccagag | aacctcaagt | gtacaccctg | cccccctccc | aggaagagat | gaccaagaac | 1140 |
| caggtgagcc | tcacctgtct | ggtgaaggga | ttctacccca | gcgacattgc | cgtggagtgg | 1200 |
| gaatccaatg | gccagcctga | gaacaattac | aagaccacac | cccccgtgct | ggacagcgat | 1260 |
| ggcagcttct | ttctgtactc | caggctgacc | gtggacaaga | gcaggtggca | ggagggcaat | 1320 |

```
gtgttctcct gcagcgtgat gcatgaggcc ctccacaatc actacaccca gaagtccctg    1380
tccctcagcc tcggaaaatg a                                              1401
```

<210> SEQ ID NO 48
<211> LENGTH: 20
<212> TYPE: PRT
<213> ORGANISM: Artificial Sequence
<220> FEATURE:
<223> OTHER INFORMATION: signal peptide

<400> SEQUENCE: 48

Met Ser Val Pro Thr Gln Val Leu Gly Leu Leu Leu Leu Trp Leu Thr
1               5                   10                  15

Asp Ala Arg Cys
            20

<210> SEQ ID NO 49
<211> LENGTH: 19
<212> TYPE: PRT
<213> ORGANISM: Artificial Sequence
<220> FEATURE:
<223> OTHER INFORMATION: signal peptide

<400> SEQUENCE: 49

Met Glu Trp Ser Trp Val Phe Leu Phe Phe Leu Ser Val Thr Thr Gly
1               5                   10                  15

Val His Ser

<210> SEQ ID NO 50
<211> LENGTH: 447
<212> TYPE: PRT
<213> ORGANISM: Artificial Sequence
<220> FEATURE:
<223> OTHER INFORMATION: ADI-12126 heavy chain

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Ala Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ile Tyr Asp Ser Ser Asp Gln Leu Asn Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
                180              185                 190
Ser Ser Ser Leu Gly Thr Lys Thr Tyr Thr Cys Asn Val Asp His Lys
            195                 200             205

Pro Ser Asn Thr Lys Val Asp Lys Arg Val Glu Ser Lys Tyr Gly Pro
    210                 215             220

Pro Cys Pro Pro Cys Pro Ala Pro Glu Phe Leu Gly Gly Pro Ser Val
225             230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265             270

Val Gln Phe Asn Trp Tyr Val Asp Gly Val Glu Val His Asn Ala Lys
            275                 280             285

Thr Lys Pro Arg Glu Glu Gln Phe Asn Ser Thr Tyr Arg Val Val Ser
        290                 295             300

Val Leu Thr Val Leu His Gln Asp Trp Leu Asn Gly Lys Glu Tyr Lys
305             310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360             365

Val Lys Gly Phe Tyr Pro Ser Asp Ile Ala Val Glu Trp Glu Ser Asn
370             375                 380

Gly Gln Pro Glu Asn Asn Tyr Lys Thr Thr Pro Pro Val Leu Asp Ser
385             390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425             430

His Asn His Tyr Thr Gln Lys Ser Leu Ser Leu Ser Leu Gly Lys
        435                 440                 445

<210> SEQ ID NO 51
<211> LENGTH: 447
<212> TYPE: PRT
<213> ORGANISM: Artificial Sequence
<220> FEATURE:
<223> OTHER INFORMATION: ADI-12152 heavy chain consensus
<220> FEATURE:
<221> NAME/KEY: MISC_FEATURE
<222> LOCATION: (1)..(1)
<223> OTHER INFORMATION: Xaa = Q or E
<220> FEATURE:
<221> NAME/KEY: MISC_FEATURE
<222> LOCATION: (115)..(115)
<223> OTHER INFORMATION: Xaa = M or L

<400> SEQUENCE: 51

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gln Gly Tyr
            20                  25                  30

Tyr Met His Trp Val Arg Gln Ala Pro Gly Gln Gly Leu Glu Trp Met
        35                  40                  45

Gly Gln Ile Asn Pro His Ser Gly Gly Thr Asn Tyr Ala Gln Lys Phe
    50                  55                  60
```

-continued

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
            85                  90                  95

Ala Arg Asp Arg Gly Glu Phe Asp Ile Ala Phe Asp Ile Trp Gly Gln
        100                 105                 110

Gly Thr Xaa Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 52
<211> LENGTH: 120
<212> TYPE: PRT
<213> ORGANISM: Artificial Sequence
<220> FEATURE:

```
<223> OTHER INFORMATION: ADI-12152 heavy chain variable region consensus
<220> FEATURE:
<221> NAME/KEY: MISC_FEATURE
<222> LOCATION: (1)..(1)
<223> OTHER INFORMATION: Xaa = Q or E
<220> FEATURE:
<221> NAME/KEY: MISC_FEATURE
<222> LOCATION: (115)..(115)
<223> OTHER INFORMATION: Xaa = M or L

<400> SEQUENCE: 52
```

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gln Gly Tyr
            20                  25                  30

Tyr Met His Trp Val Arg Gln Ala Pro Gly Gln Gly Leu Glu Trp Met
        35                  40                  45

Gly Gln Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Glu Phe Asp Ile Ala Phe Asp Ile Trp Gly Gln
            100                 105                 110

Gly Thr Xaa Val Thr Val Ser Ser
        115                 120

```
<210> SEQ ID NO 53
<211> LENGTH: 525
<212> TYPE: PRT
<213> ORGANISM: Homo sapiens

<400> SEQUENCE: 53
```

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
                275                 280                 285

Gly Thr Arg Ser Phe Leu Thr Ala Lys Trp Thr Pro Pro Gly Gly Gly
                290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
                355                 360                 365

Cys Glu Val Thr Pro Val Ser Gly Gln Glu Arg Phe Val Trp Ser Ser
            370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
                420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Gln Leu
            515                 520                 525

<210> SEQ ID NO 54
<211> LENGTH: 521
<212> TYPE: PRT
<213> ORGANISM: Murine

<400> SEQUENCE: 54

Met Arg Glu Asp Leu Leu Gly Phe Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser

```
                35                  40                  45
Pro Asn Leu Asp Pro Asn Phe Leu Arg Arg Gly Gly Val Ile Trp Gln
 50                  55                  60

His Gln Pro Asp Ser Gly Gln Pro Thr Pro Ile Pro Ala Leu Asp Leu
 65                  70                  75                  80

His Gln Gly Met Pro Ser Pro Arg Gln Pro Ala Pro Gly Arg Tyr Thr
                 85                  90                  95

Val Leu Ser Val Ala Pro Gly Leu Arg Ser Gly Arg Gln Pro Leu
                100                 105                 110

His Pro His Val Gln Leu Glu Glu Arg Gly Leu Gln Arg Gly Asp Phe
                115                 120                 125

Ser Leu Trp Leu Arg Pro Ala Leu Arg Thr Asp Ala Gly Glu Tyr His
                130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
                180                 185                 190

Pro Val Ser Val His Trp Phe Gln Gly Gln Asn Arg Val Pro Val Tyr
                195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
                260                 265                 270

Glu Leu Pro Cys His Leu Pro Pro Gly Val Gly Thr Pro Ser Leu Leu
                275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
                340                 345                 350

Gly Leu Pro Gly Ser Arg Gly Lys Leu Leu Cys Glu Val Thr Pro Ala
                355                 360                 365

Ser Gly Lys Glu Arg Phe Val Trp Arg Pro Leu Asn Asn Leu Ser Arg
                370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Gly Ala His Ser Ala Arg Arg
                420                 425                 430

Ile Ser Gly Asp Leu Lys Gly Gly His Leu Val Leu Val Leu Ile Leu
                435                 440                 445

Gly Ala Leu Ser Leu Phe Leu Leu Val Ala Gly Ala Phe Gly Phe His
450                 455                 460
```

-continued

```
Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520
```

ANTI-LAG3 ANTIBODIES AND ANTIGEN-BINDING FRAGMENTS

This Application claims the benefit of U.S. Provisional Patent Application No. 62/268,070, filed Dec. 16, 2015 which is herein incorporated by reference in its entirety.

The instant application contains a Sequence Listing which has been submitted electronically in ASCII format and is hereby incorporated by reference in its entirety. Said ASCII copy, created on Feb. 9, 2021, is named 24270USPCTSE-QTXT-09FEB2021.txt and is 63 kilobytes in size.

FIELD OF THE INVENTION

The present invention relates to anti-LAG3 antibodies as well as use of the antibodies of the present invention in the treatment of diseases such as cancer and infection.

BACKGROUND OF THE INVENTION

LAG3 (CD223) is a cell surface molecule expressed on activated T cells (Huard et al. Immunogenetics 39:213-217, 1994), NK cells (Triebel et al. J Exp Med 171:1393-1405, 1990), B cells (Kisielow et al. Eur J Immunol 35:2081-2088, 2005), and plasmacytoid dendritic cells (Workman et al. J Immunol 182:1885-1891, 2009) that plays an important role in the function of these lymphocyte subsets. In addition, the interaction between LAG3 and its major ligand, Class II MHC, is thought to play a role in modulating dendritic cell function (Andreae et al. J Immunol 168:3874-3880, 2002). Recent preclinical studies have documented a role for LAG-3 in CD8 T-cell exhaustion (Blackburn et al. Nat Immunol 10:29-37, 2009).

As with chronic viral infection, tumor antigen-specific $CD4^+$ and $CD8^+$ T cells display impaired effector function and an exhausted phenotype characterized by decreased production of pro-inflammatory cytokines and hyporesponsiveness to antigenic re-stimulation. This is mediated by cell extrinsic mechanisms, such as regulatory T-cells (Treg), and cell intrinsic mechanisms, such as inhibitory molecules that are upregulated on exhausted, tumor-infiltrating lymphocytes (TIL). These inhibitory mechanisms represent a formidable barrier to effective antitumor immunity.

LAG3 is expressed on tolerized TILs suggesting that they contribute to tumor-mediated immune suppression. Inhibition of LAG3 may lead to enhanced activation of antigen-specific T cells from which a therapeutic benefit may be gained. There is a need in the art for high efficacy therapeutic antibodies which antagonize the activity of LAG3 which can be used to generate a robust immune response to tumors.

SUMMARY OF THE INVENTION

The present invention provides an antibody or antigen-binding fragment thereof (e.g., an antibody) that specifically binds human LAG3 comprising: (a) the CDR1, CDR2, and CDR3 of a $V_L$ domain of an immunoglobulin chain that comprises the amino acid sequence set forth in SEQ ID NO: 3 or 4; and/or (b) the CDR1, CDR2, and CDR3 of a $V_H$ domain of an immunoglobulin chain that comprises the amino acid sequence set forth in SEQ ID NO: 1 or 2. For example, in an embodiment of the invention, the antibody or fragment comprises a light chain variable domain comprising: CDR-L1 that comprises the amino acid sequence: 8; CDR-L2 that comprises the amino acid sequence: 9; and CDR-L3 that comprises the amino acid sequence: 10; and/or a heavy chain variable domain comprising: CDR-H1 that comprises the amino acid sequence: 5; CDR-H2 that comprises the amino acid sequence: 6; and CDR-H3 that comprises the amino acid sequence: 7. In an embodiment of the invention, the antibody or antigen-binding fragment comprises a light chain variable domain comprising: CDR-L1 that comprises the amino acid sequence: 14; CDR-L2 that comprises the amino acid sequence: 15; and CDR-L3 that comprises the amino acid sequence: 16; and/or a heavy chain variable domain comprising: CDR-H1 that comprises the amino acid sequence: 11; CDR-H2 that comprises the amino acid sequence: 12; and CDR-H3 that comprises the amino acid sequence: 13.

The present invention also provides an antibody or antigen-binding fragment thereof (e.g., an antibody) that specifically binds human LAG3 comprising a light chain immunoglobulin, a heavy chain immunoglobulin, or both a light and heavy chain immunoglobulin, selected from the group consisting of: a light chain immunoglobulin comprising an amino acid sequence having at least 90% (e.g., 95%, 96%, 97%, 98%, 99% or 100%) amino acid sequence identity to the amino acid sequence set forth in SEQ ID NO: 3, and/or a heavy chain immunoglobulin comprising an amino acid sequence having at least 90% (e.g., 95%, 96%, 97%, 98%, 99% or 100%) amino acid sequence identity to the amino acid sequence set forth in SEQ ID NO: 1. In an embodiment of the invention, the antibody or antigen-binding fragment comprises a light chain immunoglobulin comprising an amino acid sequence having at least 90% (e.g., 95%, 96%, 97%, 98%, 99% or 100%) amino acid sequence identity to the amino acid sequence set forth in SEQ ID NO: 4, and/or a heavy chain immunoglobulin comprising an amino acid sequence having at least 90% (e.g., 95%, 96%, 97%, 98%, 99% or 100%) amino acid sequence identity to the amino acid sequence set forth in SEQ ID NO: 2. In an embodiment of the invention, the antibody or antigen-binding fragment comprises a light chain immunoglobulin comprising CDR-L1, CDR-L2 and CDR-L3 of the immunoglobulin comprising the amino acid sequence of SEQ ID NO: 3, and having at least 90% (e.g., 95%, 96%, 97%, 98%, 99% or 100%) amino acid sequence identity to the amino acid sequence set forth in SEQ ID NO: 3; and/or a heavy chain immunoglobulin comprising CDR-H1, CDR-H2 and CDR-H3 of the immunoglobulin comprising the amino acid sequence of SEQ ID NO: 1, and having at least 90% (e.g., 95%, 96%, 97%, 98%, 99% or 100%) amino acid sequence identity to the amino acid sequence set forth in SEQ ID NO: 1. In an embodiment of the invention, the antibody or antigen-binding fragment comprises a light chain immunoglobulin comprising CDR-L1, CDR-L2 and CDR-L3 of the immunoglobulin comprising the amino acid sequence of SEQ ID NO: 4, and having at least 90% (e.g., 95%, 96%, 97%, 98%, 99% or 100%) amino acid sequence identity to the amino acid sequence set forth in SEQ ID NO: 4; and/or a heavy chain immunoglobulin comprising CDR-H1, CDR-H2 and CDR-H3 of the immunoglobulin comprising the amino acid sequence of SEQ ID NO: 2, and having at least 90% (e.g., 95%, 96%, 97%, 98%, 99% or 100%) amino acid sequence identity to the amino acid sequence set forth in SEQ ID NO: 2. In an embodiment of the invention, the antibody or antigen-binding fragment comprises a light chain immunoglobulin comprising the amino acid sequence set forth in SEQ ID NO: 3; and/or a heavy chain immunoglobulin comprising the amino acid sequence set forth in SEQ ID NO: 1. In an embodiment of the invention, the antibody or antigen-binding fragment comprises a light chain immunoglobulin comprising the amino acid sequence set forth in SEQ ID NO: 4; and/or a heavy chain immunoglobulin comprising the amino acid sequence set forth in SEQ ID NO: 2. In an embodiment of the invention, the anti-LAG3 antibody or antigen-binding fragment thereof comprises a light chain immunoglobulin comprising the amino acid sequence set forth in SEQ ID NO: 22; and a heavy chain immunoglobulin comprising the amino acid sequence set forth in SEQ ID NO: 21. In an embodiment of the invention, the anti-LAG3 antibody or antigen-binding fragment thereof comprises a light chain immunoglobulin comprising the amino acid sequence set forth in SEQ ID NO: 24; and a heavy chain immunoglobulin comprising the amino acid sequence set forth in SEQ ID NO: 23.

In an embodiment of the invention, an anti-LAG3 antibody or antigen-binding fragment thereof of the present invention is glycosylated with engineered yeast N-linked glycans or CHO N-linked glycans.

The present invention also provides a polypeptide comprising the amino acid sequence of a member selected from the group consisting of SEQ ID NOs: 1-16 and 21-24; as well as polynucleotides encoding such polypeptides, vectors comprising the polynucleotides as well as host cells comprising any of the polypeptides, antibodies, antigen-binding fragments, vectors or polynucleotides.

The present invention also provides a composition or kit comprising the antibody, antigen-binding fragment, polypeptide, polynucleotide or vector of the present invention and, optionally, a pharmaceutically acceptable carrier or diluent; which is optionally in association with a further therapeutic agent. For example, in an embodiment of the invention, the further therapeutic agent is a member selected from the group consisting of an anti-cancer therapeutic agent, an inhibitor of an immunomodulatory receptor, an anti-emetic, an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, a farnesyl protein transferase inhibitor, an anti-PD1 antibody or an antigen-binding fragment thereof, pembrolizumab, nivolumab, CT-011, anti-CTLA4 antibody or an antigen-binding fragment thereof, anti-TIM3 antibody or an antigen-binding fragment thereof, anti-CS1 antibody or an antigen-binding fragment thereof, elotuzumab, anti-KIR2DL1/2/3 antibody or an antigen-binding fragment thereof, lirilumab, anti-CD137 antibody or an antigen-binding fragment thereof, urelumab, anti-GITR antibody or an antigen-binding fragment thereof, TRX518, anti-PD-L1 antibody or an antigen-binding fragment thereof, BMS-936559, MSB0010718C, MPDL3280A, anti-PD-L2 antibody or an antigen-binding fragment thereof, anti-ILT1 antibody or an antigen-binding fragment thereof, anti-CEACAM1 antibody or antigen-binding fragment thereof, anti-ILT2 antibody or an antigen-binding fragment thereof, anti-ILT3 antibody or an antigen-binding fragment thereof, anti-ILT4 antibody or an antigen-binding fragment thereof, anti-ILT5 antibody or an antigen-binding fragment thereof, anti-ILT6 antibody or an antigen-binding fragment thereof, anti-ILT7 antibody or an antigen-binding fragment thereof, anti-ILT8 antibody or an antigen-binding fragment thereof, anti-CD40 antibody or an antigen-binding fragment thereof, anti-OX40 antibody or an antigen-binding fragment thereof, anti-CD137 antibody or an antigen-binding fragment thereof, anti-KIR2DL1 antibody or an antigen-binding fragment thereof, anti-KIR2DL2/3 antibody or an antigen-binding fragment thereof, anti-KIR2DL4 antibody or an antigen-binding fragment thereof, anti-KIR2DL5A antibody or an antigen-binding fragment thereof, anti-KIR2DL5B antibody or an antigen-binding fragment thereof, anti-KIR3DL1 antibody or an antigen-binding fragment thereof, anti-KIR3DL2 antibody or an antigen-binding fragment thereof, anti-KIR3DL3 antibody or an antigen-binding fragment thereof, anti-NKG2A antibody or an antigen-binding fragment thereof, anti-NKG2C antibody or an antigen-binding fragment thereof, anti-NKG2E antibody or an antigen-binding fragment thereof, IL-10, anti-IL10, anti-TSLP, PEGylated IL-10, 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, aflibercept, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, ATI3387, atrasentan, axitinib, AZD1152, *Bacillus* Calmette-Guerin (BCG) vaccine, batabulin, BC-210, BGJ398, besodotux, bevacizumab, bicalutamide, Bio111, BIO140, BKM120, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, CEA vaccine, cediranib, CG-1521, CG-781, chlamydocin, chlorambucil, chlorotoxin, cilengitide, cimitidine, cisplatin, cladribine, clodronate, cobimetnib, COL-3, CP-724714, cyclophosphamide, cyproterone, cyproteroneacetate, cytarabine, cytosinearabinoside, dabrafenib, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, DNE03, docetaxel, dovitinib, doxorubicin, droloxifene, edotecarin, yttrium-90 labeled-edotreotide, edotreotide, EKB-569, EMD121974, encorafenib, endostatin, enzalutamide, enzastaurin, epirubicin, epithilone B, ERA-923, erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, fulvestrant, galeterone, ganetespib, gefitinib, gemcitabine, gimatecan, glucopyranosyl lipid A, goserelin, goserelin acetate, gossypol, GSK461364, GSK690693, EMIR-3339, hydroxyprogesteronecaproate, hydroxyurea, IC87114, idarubicin, idoxyfene, ifosfamide, IM862, imatinib, imiquimod, IMC-1C11, INCB24360, INC280, INO1001, interferon, interleukin-2, interleukin-12, ipilimumab, irinotecan, JNJ-16241199, ketoconazole, KRX-0402, lapatinib, lasofoxifene, LEE011, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY3009120, LY317615, marimastat, mechlorethamine, medroxyprogesteroneacetate, megestrolacetate, MEK162, melphalan, mercaptopurine, mesna, methotrexate, mithramycin, mitomycin, mitotane, mitoxantrone, tozasertib, MLN8054, a suspension of heat killed *Mycobacterium obuense*, natitoclax, neovastat, neratinib, neuradiab, nilotinib, nilutimide, nolatrexed, NVP-BEZ235, oblimersen, octreotide, ofatumumab, oregovomab, ornatuzumab, orteronel, oxaliplatin, paclitaxel, palbociclib, pamidronate, panitumumab, pazopanib, PD0325901, PD184352, PEG-interferon, pemetrexed, pentostatin, perifosine, phenylalanine mustard, PI-103, pictilisib, PIK-75, pipendoxifene, PKI-166, plicamycin, PLX8394, poly-ICLC, porfimer, prednisone, procarbazine, progestins, PSK, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, 6-thioguanine, thiotepa, ticilimumab, tipifarnib, tivozanib, TKI-258, TLK286, TNFα, topotecan, toremifene citrate, trabectedin, trametinib, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vemurafenib, vinblastine, vincristine, vindesine, vinorelbine, vitaxin, vitespan, vorinostat, VX-745, wortmannin, Xr311, zanolimumab, ZK186619, ZK-304709, ZM336372, ZSTK474, Z-100, casopitant, netupitant, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, GCSF, PEG-GCSF, erythropoietin, epoetin alfa, darbepoetin alfa, a Bruton's tyrosine kinase (BTK) inhibitor, a prostate specific antigen vaccine, azacitidine, eribulin mesylate, lenvatinib mesylate, epacadostat, an anti-4-1BB agonist antibody or antigen-binding fragment, crizotinib, a CSF1 receptor kinase inhibitor, entinostat, birinapant, and niraparib. In an embodiment of the invention, the further therapeutic agent is pembrolizumab.

The present invention also provides a vaccine comprising an antigen and a pharmaceutically acceptable carrier in association with any anti-LAG3 antibody or fragment or composition of the present invention.

The present invention also provides a vessel or injection device comprising an anti-LAG3 antibody, antigen-binding fragment, composition, polypeptide, polynucleotide, vector or vaccine of the present invention; optionally, wherein the vessel or device includes a pharmaceutically acceptable carrier or diluent.

The present invention also provides a method for antagonizing LAG3 in a human patient in need thereof comprising administering, to the subject, an effective amount of an anti-LAG3 antibody or antigen-binding fragment of the present invention.

The present invention also provides a method of treating a cancer or infectious disease in a subject, comprising administering to the subject an effective amount of the antibody or antigen-binding fragment thereof, optionally, in association with a further therapeutic agent (e.g., any of those set forth herein, such as pembrolizumab), therapeutic procedure or vaccine. For example, in an embodiment of the invention, the cancer is metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer.

The present invention also provides a method of administering an anti-LAG3 antibody or antigen-binding fragment, composition, polypeptide, vaccine, vector or polynucleotide of the present invention to a subject, comprising injecting the antibody, fragment, polypeptide, vaccine or polynucleotide into the body of the subject using an injection device; and, optionally, also administering a further therapeutic agent (e.g., any of those set forth herein) or therapeutic procedure to the subject.

The present invention also provides a method of producing an anti-LAG3 antibody or antigen-binding fragment thereof or polypeptide of the present invention comprising: a. culturing a host cell (e.g., Chinese hamster ovary cell) comprising a polynucleotide encoding the polypeptide or an immunoglobulin chain of the antibody or antigen-binding fragment in a culture medium under conditions favorable to expression of the polynucleotide; and b. optionally, recovering the antibody, antigen-binding fragment or polypeptide from the host cell and/or culture medium. Any antibody or antigen-binding fragment thereof that specifically binds human LAG3 or polypeptide which is the product of such a method is part of the present invention.

The present invention also provides a method for detecting the presence of a LAG3 peptide or a fragment thereof in a sample comprising contacting the sample with an anti-LAG3 antibody or antigen-binding fragment of the present invention and detecting the presence of a complex between the antibody or fragment and the peptide; wherein detection of the complex indicates the presence of the LAG3 peptide.

BRIEF DESCRIPTION OF THE FIGURES

FIG. 2A-2C. ADI-12126 and ADI-12152 amino acid and nucleotide sequences. (A) ADI-12126 heavy chain (SEQ ID NO: 50), ADI-12126 heavy chain nucleotide sequence (SEQ ID NO: 47), (B) ADI-12126 light chain (SEQ ID NO: 22), ADI-12126 light chain nucleotide sequence (SEQ ID NO: 18), ADI-12152 heavy chain (SEQ ID NO: 23), ADI-12152 heavy chain nucleotide sequence (SEQ ID NO: 19), (C) ADI-12152 light chain (SEQ ID NO: 24), ADI-12152 light chain nucleotide sequence (SEQ ID NO: 20).

DETAILED DESCRIPTION

Figure 1:
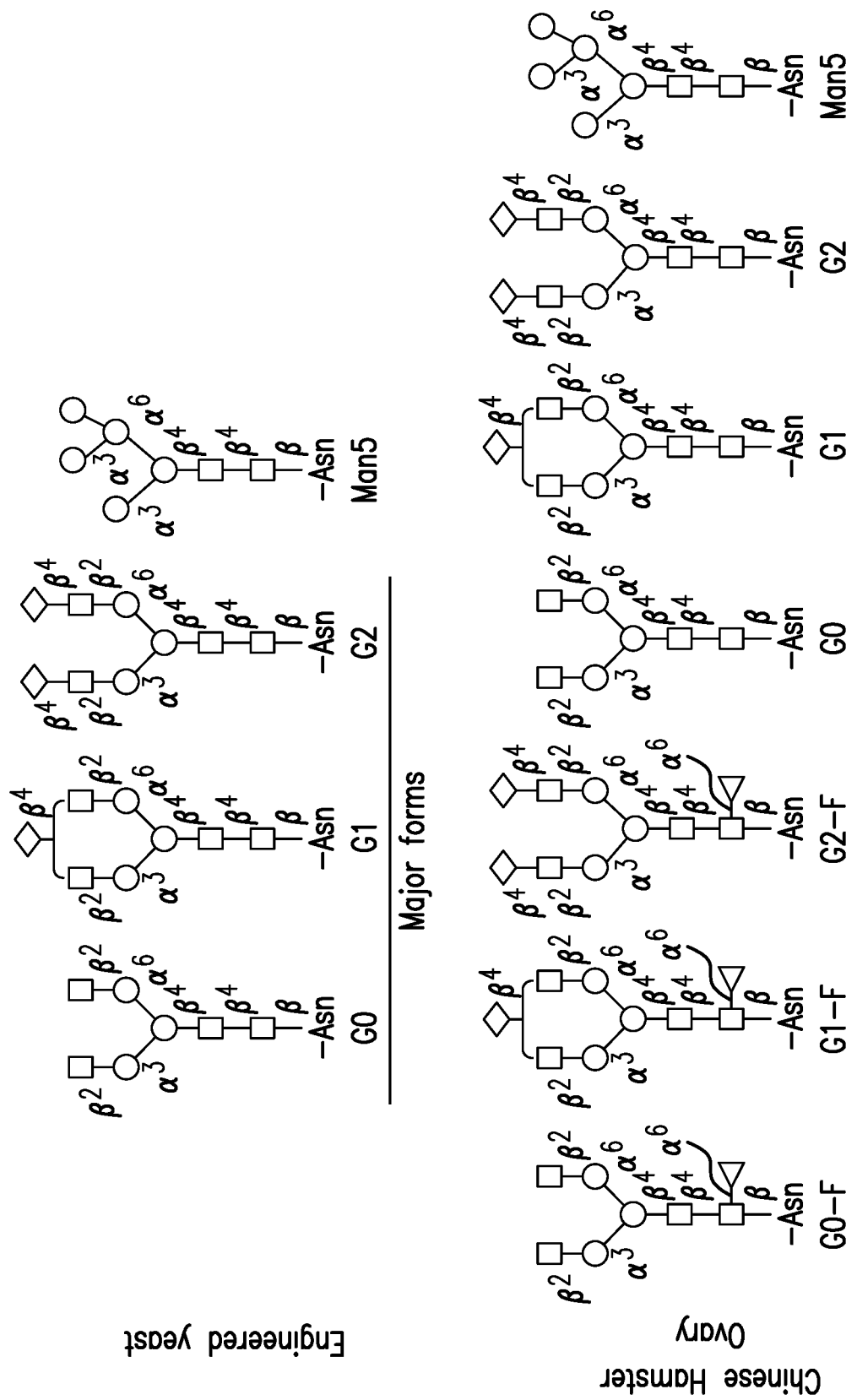
FIG. 1. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

The present invention includes anti-LAG3 antibodies comprising fully human immunoglobulin chain amino acid sequences. Such antibodies were isolated from a human immunoglobulin library using a yeast surface display system. Uses of such antibodies include stimulation of the immune system, which can be used to treat cancer or infectious diseases.

Abbreviations

Throughout the detailed description and examples of the invention the following abbreviations will be used:
ADCC Antibody-dependent cellular cytotoxicity
CDC Complement-dependent cytotoxicity CDR Complementarity determining region in the immunoglobulin variable regions, defined using the Kabat numbering system
CHO Chinese hamster ovary
ELISA Enzyme-linked immunosorbant assay
FR Antibody framework region: the immunoglobulin variable regions excluding the CDR regions.
HRP Horseradish peroxidase
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
PCR Polymerase chain reaction
V region The segment of IgG chains which is variable in sequence between different antibodies. It extends to Kabat residue 109 in the light chain and 113 in the heavy chain.
VH Immunoglobulin heavy chain variable region
VK or VL Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

LAG3

The term "LAG3", with respect to the polypeptide to which antibodies and antigen-binding fragments of the present invention bind, refers to human and cynomolgous monkey, e.g., *Macaca fascicularis* or *Macaca* mulatta LAG3 as well as fragments thereof such as the mature fragment thereof lacking the signal peptide.

In an embodiment of the invention, the amino acid sequence of human LAG (Lymphocyte Activation Gene-3) comprises the amino acid sequence:

```
                                        (SEQ ID NO: 53)
MWEAQFLGLL FLQPLWVAPV KPLQPGAEVP VVWAQEGAPA

QLPCSPTIPL QDLSLLRRAG VTWQHQPDSG PPAAAPGHPL

APGPHPAAPS SWGPRPRRYT VLSVGPGGLR SGRLPLQPRV

QLDERGRQRG DFSLWLRPAR RADAGEYRAA VHLRDRALSC

RLRLRLGQAS MTASPPGSLR ASDWVILNCS FSRPDRPASV

HWFRNRGQGR VPVRESPHHH LAESFLFLPQ VSPMDSGPWG

CILTYRDGFN VSIMYNLTVL GLEPPTPLTV YAGAGSRVGL

PCRLPAGVGT RSFLTAKWTP PGGGPDLLVT GDNGDFTLRL

EDVSQAQAGT YTCHIHLQEQ QLNATVTLAI ITVTPKSFGS

PGSLGKLLCE VTPVSGQERF VWSSLDTPSQ RSFSGPWLEA

QEAQLLSQPW QCQLYQGERL LGAAVYFTEL SSPGAQRSGR

APGALPAGHL LLFLILGVLS LLLLVTGAFG FHLWRRQWRP

RRFSALEQGI HPPQAQSKIE ELEQEPEPEP EPEPEPEPEP

EPEQL;
see also Uniprot accession no. P18627.
```

In an embodiment of the invention, the amino acid sequence of mouse LAG3 comprises the amino acid sequence:

```
                                        (SEQ ID NO: 54)
MREDLLLGFL LLGLLWEAPV VSSGPGKELP VVWAQEGAPV

HLPCSLKSPN LDPNFLRRGG VIWQHQPDSG QPTPIPALDL

HQGMPSPRQP APGRYTVLSV APGGLRSGRQ PLHPHVQLEE

RGLQRGDFSL WLRPALRTDA GEYHATVRLP NRALSCSLRL

RVGQASMIAS PSGVLKLSDW VLLNCSFSRP DRPVSVHWFQ

GQNRVPVYNS PRHFLAETFL LLPQVSPLDS GTWGCVLTYR

DGFNVSITYN LKVLGLEPVA PLTVYAAEGS RVELPCHLPP

GVGTPSLLIA KWTPPGGGPE LPVAGKSGNF TLHLEAVGLA

QAGTYTCSIH LQGQQLNATV TLAVITVTPK SFGLPGSRGK

LLCEVTPASG KERFVWRPLN NLSRSCPGPV LEIQEARLLA

ERWQCQLYEG QRLLGATVYA AESSSGAHSA RRISGDLKGG

HLVLVLILGA LSLFLLVAGA FGFHWWRKQL LLRRFSALEH

GIQPFPAQRK IEELERELET EMGQEPEPEP EPQLEPEPRQ

L;
See also Uniprot accession no. Q61790
```

In an embodiment of the invention, the amino acid sequence of cynomolgous monkey LAG3 comprises the amino acid sequence of NCBI reference number XP_005570011.1.

The mature sequence of human, mouse LAG3, i.e. the sequence after removal of the signal peptide, comprises amino acids 1-28 of SEQ ID NO: 53, or 54.

Anti-LAG3 Antibodies and

Antigen-Binding Fragments Thereof

The present invention provides antibodies or antigen-binding fragments thereof that specifically bind LAG3 (e.g., ADI-12126 or ADI-12152) and uses of such antibodies or fragments. In an embodiment of the invention, the antibody or fragment is an antibody.

The present invention includes "antagonist" anti-LAG3 antibodies and antigen-binding fragments thereof and methods of use thereof, e.g., human antagonist anti-LAG3 antibodies and fragments. An antagonist anti-LAG3 antibody or antigen-binding fragment thereof antagonizes an activity of LAG3 (e.g., human LAG3) such as by inhibiting LAG3 binding to MHC class II molecules; competing with MHC class II molecules for LAG3 binding; or when a cell or subject is contacted with the antibody or fragment, a biological phenotype associated with LAG3 antagonism, such as stimulation of antigen-specific T-cell production of IL-2, is produced.

The present invention provides human anti-LAG3 antibody and antigen-binding fragment molecules that comprise only human immunoglobulin chain sequences. Such human molecules are not derived directly from the body of a human subject. Rather, the molecules may be derived, for example, from a yeast library having cells that comprise human immunoglobulin genes which, in turn, produce the human antibodies and antigen-binding fragments. See e.g., Xu et al. Prot. Eng. Design & Selection 26(10):663-70 (2013).

ADI-12126 and ADI-12152 were isolated from a fully human antibody library displayed at the surface of engineered yeast strains. ADI-12126 and ADI-12152 were selected for binding by Cell ELISA (CHO cells expressing human or cynomolgous monkey LAG3) and Biacore, and for activity in functional assays: MHC class II binding in Daudi cells (Blocking assay) and in the engineered 3A9 assay with IL-2 read-out. ADI-12126 and ADI-12152 were subsequently affinity-matured to achieve the desired affinity.

The present invention includes anti-LAG3 antibodies (e.g., ADI-12126 or ADI-12152) and methods of use thereof. As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies (wherein one or more of such antibodies or an antigen-binding fragment thereof comprises an ADI-12126 and/or ADI-12152 sequence set forth herein or a variant thereof), multispecific antibodies (e.g., bispecific antibodies), biparatopic antibodies, fully human antibodies, chimeric antibodies and camelized single domain antibodies.

The present invention includes anti-LAG3 antigen-binding fragments (e.g., of ADI-12126 and ADI-12152) and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; single-chain antibody molecules, e.g., sc-Fv; nanobodies and multispecific antibodies formed from antibody fragments.

The present invention includes anti-LAG3 Fab fragments (e.g., of ADI-12126 and ADI-12152) and methods of use thereof. A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

The present invention includes anti-LAG3 antibodies (e.g., ADI-12126 or ADI-12152) and antigen-binding fragments thereof which comprise an Fc region and methods of use thereof. An "Fc" region contains two heavy chain fragments comprising the $C_H1$ and $C_H2$ domains of an antibody (e.g., $C_H1$ and $C_H2$ and $C_H3$). The two heavy chain fragments are held together by two or more disulfide bonds and by hydrophobic interactions of the $C_H3$ domains.

The present invention includes anti-LAG3 Fab' fragments (e.g., of ADI-12126 and ADI-12152) and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab') 2 molecule.

The present invention includes anti-LAG3 F(ab')$_2$ fragments (e.g., of ADI-12126 and ADI-12152) and methods of use thereof. A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The present invention includes anti-LAG3 Fv fragments (e.g., of ADI-12126 and ADI-12152) and methods of use thereof. The "Fv region" comprises the variable regions from both the heavy and light chains, but lacks the constant regions.

The present invention includes anti-LAG3 scFv fragments (e.g., of ADI-12126 and ADI-12152) and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO88/01649 and U.S. Pat. Nos. 4,946,778 and 5,260,203.

The present invention includes anti-LAG3 domain antibodies (e.g., derived from sequences of ADI-12126 and/or ADI-12152, e.g., 3 HCDRS and/or 3 LCDRs) and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens. In an embodiment of the invention, the domain antibody is a single domain antibody or nanobody. In an embodiment of the invention, a domain antibody is a nanobody comprising the 3 ADI-12126 HCDRs or 3 ADI-12126 LCDRS or 3 ADI-12152 HCDRs or 3 ADI-12152 LCDRs or a variant of any thereof.

The present invention includes anti-LAG3 bivalent antibodies (e.g., ADI-12126 or ADI-12152) and methods of use thereof. A "bivalent antibody" comprises two antigen-binding sites. In some instances, the two binding sites have the same antigen specificities. However, bivalent antibodies may be bispecific (e.g., with affinity for LAG3 and another antigen).

The present invention includes bispecific antibodies and antigen-binding fragments having a binding specificity for LAG3 and another antigen and methods of use thereof. A bispecific antibody is an artificial hybrid antibody having two different heavy/light chain pairs and two different binding sites, for example, 1 heavy and 1 light chain of ADI-12126 or of ADI-12152 along with 1 heavy and 1 light chain of another antibody having specificity for an antigen which is different from those of the other heavy and light chain pair. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

Biparatopic antibodies are antibodies having binding specificity for different epitopes on the same antigen. The present invention includes biparatopic antibodies having 1 heavy and 1 light chain of ADI-12126 or of ADI-12152 along with 1 heavy and 1 light chain of another antibody having specificity for a LAG3 epitope which is different from those of the other heavy and light chain pair.

The present invention includes anti-LAG3 antibodies and antigen-binding fragments thereof comprising 1 heavy and 1 light chain of ADI-12126 and 1 heavy and 1 light chain of ADI-12152; as well as anti-LAG3 antibodies and antigen-binding fragments thereof comprising 1 heavy and 1 light chain having the 3 CDR-Hs and 3 CDR-Ls of ADI-12126 along with 1 heavy and 1 light chain having the 3 CDR-Hs and 3 CDR-Ls of ADI-12152.

The present invention includes anti-LAG3 camelized single domain antibodies (e.g., of ADI-12126 and ADI-12152) and methods of use thereof. In certain embodiments, antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

The present invention includes anti-LAG3 diabodies (e.g., of ADI-12126 and ADI-12152) and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404, 097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

Typically, an antibody (e.g., ADI-12126 or ADI-12152) or antigen-binding fragment of the invention which is modified in some way retains at least 10% of its LAG3 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the LAG3 binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-LAG3 antibodies (e.g., ADI-12126 or ADI-12152) and antigen-binding fragments thereof and methods of use thereof as well as isolated polypeptide immunoglobulin chains thereof and isolated polynucleotides encoding such polypeptides and isolated vectors including such polynucleotides. "Isolated" antibodies or antigen-binding fragments thereof, polypeptides, polynucleotides and vectors, are at least partially free of other biological molecules from the cells or cell culture from which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention includes monoclonal anti-LAG3 antibodies (e.g., ADI-12126 or ADI-12152) and antigen-binding fragments thereof as well as monoclonal compositions comprising a plurality of isolated monoclonal antibodies. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816, 567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

The present invention includes anti-LAG3 chimeric antibodies (e.g., derived from or based on ADI-12126 and ADI-12152) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). In an embodiment of the invention, the variable domains are obtained from a human antibody (the "parental antibody"), and the constant domain sequences are obtained from non-human antibodies (e.g., mouse, rat, dog, monkey, gorilla, horse).

The present invention includes anti-LAG3 fully human antibodies (e.g., ADI-12126 or ADI-12152) and antigen-binding fragments thereof and methods of use thereof. The term "fully human antibody or antigen-binding fragment thereof" or "human antibody or antigen-binding fragment thereof" refers to an antibody or antigen-binding fragment thereof that comprises human immunoglobulin protein sequences only which has been isolated from a non-human source. A fully human antibody may contain murine carbohydrate chains if produced in a mouse, in a mouse cell, or in a hybridoma derived from a mouse cell. A "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only. In an embodiment of the invention, an fully human anti-LAG3 antibody or antigen-binding fragment thereof is the product of isolation from a transgenic animal, e.g., a mouse (e.g., a HUMAB® mouse, see e.g., U.S. Pat. Nos. 5,545,806; 5,569,825; 5,625,126; 5,633,425; 5,661,016; 5,770,429; 5,789,650; 5,814,318; 5,874,299 and 5,877,397; and Harding, et al., (1995) Ann. NY Acad. Sci. 764:536 546; or a XENOMOUSE®, see e.g., Green et al., 1999, J. Immunol. Methods 231:11-23), which has been genetically modified to have fully human immunoglobulin genes; or the product of isolation from a phage or virus which expresses the immunoglobulin chains of the anti-LAG3 fully human antibody or antigen-binding fragment thereof.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention comprises anti-LAG3 antibodies and antigen-binding fragments of any of these classes or subclasses of antibodies.

In one embodiment, the anti-LAG3 antibody or antigen-binding fragment comprises a heavy chain constant region, e.g. a human constant region, such as γ1, γ2, γ3, or γ4 human heavy chain constant region or a variant thereof. In another embodiment, the anti-LAG3 antibody or antigen-binding fragment comprises a light chain constant region, e.g. a human light chain constant region, such as lambda or kappa human light chain region or variant thereof. By way of example, and not limitation, the human heavy chain constant region can be γ4 and the human light chain constant region can be kappa. In an alternative embodiment, the Fc region of the antibody is γ4 with a Ser228Pro mutation (Schuurman, J et. al., *Mol. Immunol.* 38: 1-8, 2001).

In some embodiments, different constant domains may be appended to $V_L$ and $V_H$ regions derived from the CDRs provided herein. For example, if a particular intended use of an antibody (or fragment) of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. The present invention includes anti-LAG3 antibodies and antigen-binding fragments thereof which comprise an IgG4 constant domain, e.g., antagonist human anti-LAG3 antibodies and fragments, and methods of use thereof. In one embodiment, the IgG4 constant domain can differ from the native human IgG4 constant domain (Swiss-Prot Accession No. P01861.1) at a position corresponding to position 228 in the EU system and position 241 in the KABAT system, where the native Ser108 is replaced with Pro, in order to prevent a potential interchain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) *Mol. Imunol.* 30:105. In other instances, a modified IgG1 constant domain which has been modified to increase half-life or reduce effector function can be used.

In an embodiment of the invention, anti-LAG3 antibodies of the present invention (e.g., ADI-12126 or ADI-12152) comprise a full tetrameric structure having two light chains and two heavy chains, including constant regions.

The variable regions of each light/heavy chain pair form the antibody binding site. Thus, in general, an intact antibody has two binding sites. Except in bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" or "complementarity determining region" or "CDR" refers to the amino acid residues of an antibody or antigen-binding fragment thereof that are responsible for antigen-binding. The CDRs include the CDR-L1, CDR-L2 and CDR-L3 in the light chain variable domain and CDR-H1, CDR-H2 and CDR-H3 in the heavy chain variable domain). See Kabat et al. (1991) Sequences of Proteins of Immunological Interest, 5th Ed. Public Health Service, National Institutes of Health, Bethesda, Md.; Johnson et al. (2001) Nucleic Acids Res. 2001; 29(1): 205-206 (defining the CDR regions of an antibody by sequence); see also Chothia and Lesk (1987) *J. Mol. Biol.* 196: 901-917; Chothia et al. Nature 342, 877 (1989), and Tramontano et al. J. Mol. Biol. 215, 175 (1990) (defining the CDR regions of an antibody by structure); see also Macallum et al. J Mol Biol. 1996 Oct. 11; 262(5):732-45. As used herein, the term "framework" or "FR" residues refers to those variable domain residues other than the CDR residues defined herein as CDR residues.

"Isolated nucleic acid molecules" or "isolated polynucleotides" (e.g., DNA or RNA) are also not associated with polynucleotides in which the isolated polynucleotide is found in nature, or are linked to a polynucleotide to which it is not linked in nature. For purposes of this disclosure, it should be understood that "a polynucleotide comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences. As is discussed below, the present invention includes isolated polynucleotides encoding any of the immunoglobulin chains discussed herein.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," and "cell line," are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

Physical and Functional Properties of the Exemplary Anti-LAG3 Antibodies

The present invention provides anti-LAG3 antibodies and antigen-binding fragments thereof and methods of use of the antibodies or antigen-binding fragments thereof in the treatment or prevention of disease. In one embodiment, the invention provides for human anti-LAG3 antibodies and antigen-binding fragments thereof and methods of use of the antibodies or antigen-binding fragments thereof in the treatment or prevention of disease. In one embodiment, the invention provides for antagonistic anti-LAG3 antibodies and methods of use of the antibodies or antigen-binding fragments thereof in the treatment or prevention of disease.

An "anti-LAG3" antibody or antigen-binding fragment thereof of the present invention includes any antibody or antigen-binding fragment thereof comprising one or more CDRs (e.g., 3 HCDRs and 3 LCDRs), any variable region, any heavy immunoglobulin chain or any light immunoglobulin chain of ADI-12126 or ADI-12152 or a variant thereof; which specifically binds to LAG3. For example, the present invention also includes anti-LAG3 antibodies and antigen-binding fragments including any combination of the light and heavy chains that are set forth herein or variants of such chains. Anti-LAG3 antibodies and antigen-binding fragments include those having any one or more of the CDRs (e.g., CDR-L1, CDR-L2, CDR-L3, CDR-H1, CDR-H2 and CDR-H3) of the immunoglobulin chains set forth herein or one or more variants of such CDRs; which specifically bind LAG3. A particular embodiment of the invention includes anti-LAG3 antibodies and fragments comprising only ADI-12126 or only ADI-12152 immunoglobulin heavy and light immunoglobulin chains and/or only ADI-12126 or only ADI-12152 LCDRs and HCDRs. These antibodies and fragments are part of the present invention along with their uses, e.g., as set forth herein.

The present invention also includes any antibody or antigen-binding fragment thereof that binds to the same epitope in LAG3 to which the antibodies and fragments discussed herein bind and any antibody or antigen-binding fragment that cross-blocks (partially or fully) or is cross-blocked (partially or fully) by an antibody or fragment discussed herein for LAG3 binding; as well as any variant thereof.

The cross-blocking antibodies and antigen-binding fragments thereof discussed herein can be identified based on their ability to block any of the anti-LAG3 antibodies or fragments specifically set forth herein, e.g., ADI-12126 or ADI-12152, from binding to LAG3, in binding assays (e.g., bio-layer interferometry (BLI; for example FORTEBIO OCTET binding assay; Pall ForteBio Corp; Menlo Park, Calif.), surface plasmon resonance (SPR), BIACore, ELISA, flow cytometry). For example, in an embodiment of the invention, when using BLI, the tip of a fiber-optic probe is coated with ligand (e.g., LAG3) and acts as the biosensor wherein binding of anti-LAG3 antibody or antigen-binding fragment to the LAG3 alters the interference pattern of white light reflected from the probe layer bound to LAG3 and an internal reference layer. The shift is indicative of antigen/ antibody or fragment binding. In an embodiment of the invention, the LAG3 coated tip is immersed in a solution of analyte containing antibody or antigen-binding fragment, e.g., in the well of either a 96- or 384-well plate. In an embodiment of the invention, the plate is shaken during reading to create orbital flow. To read the assay, white light is directed down the length of the fiber. As mentioned above, interference between light reflecting off the reference layer and immobilized surfaces containing LAG3 of the tip creates a distinctive pattern of light returning up the fiber. As molecules bind to the immobilized sensor surface, that pattern changes in proportion to the extent of binding. For example, assays can be used in which a LAG3 protein is immobilized on a BLI probe or plate, a reference anti-LAG3 antibody or fragment (e.g., ADI-12126 or ADI-12152) binds to LAG3 (e.g., at saturating concentration) and a test anti-LAG3 antibody or fragment is added. The ability of the test antibody to compete with the reference antibody for LAG3 binding is then determined. In the BLI format, light interference of the LAG3 complex is monitored to determine if the test antibody effectively competes with the reference antibody, e.g., nanometers of light wavelength shift over time is monitored wherein a shift indicates additional binding of the test antibody and a lack of cross-blocking. In an embodiment of the invention, in the BLI format, crossblocking is qualitatively deemed to have occurred between the antibodies if no additional binding of test antibody is observed. In an embodiment of the invention, as a control, cross-blocking of the reference antibody with itself is confirmed; wherein the assay is determined to be operating correctly if the reference antibody can cross-block itself from LAG3 binding. The ability of a test antibody to inhibit the binding of, for example, an anti-LAG3 antibody or fragment, to LAG3 demonstrates that the test antibody can cross-block the an anti-LAG3 for binding to LAG3 and thus, may, in some cases, bind to the same epitope on LAG3 as the anti-LAG3. As stated above, antibodies and fragments that bind to the same epitope as any of the anti-LAG3 antibodies or fragments of the present invention also form part of the present invention. In an embodiment of the invention, BLI is conducted in a sandwich format wherein a reference anti-LAG3 antibody or antigen-binding fragment is immobilized to the probe and then bound with LAG3. Test anti-LAG3 antibody or antigen-binding fragment is then tested for the ability to block binding of the references antibody or fragment. The scope of the present invention includes such a method for identifying an antibody or antigen-binding fragment that cross-blocks an anti-LAG3 antibody or antigen-binding fragment of the present invention (e.g., ADI-12126 or ADI-12152) from binding to LAG3; as well as any cross-blocking antibody or fragment identified using such a method.

The scope of the present invention, includes anti-LAG3 antibodies and antigen-binding fragments thereof that specifically bind LAG3, which have any combination of CDRs (e.g., 3 CDR-Ls) from the immunoglobulin light chains of SEQ ID NOs: 2 and 4 and/or which have any combination of CDRs (e.g., 3 CDR-Hs) from the immunoglobulin heavy chains of SEQ ID NOs: 1 and 3; wherein the CDRs are as defined by Kabat and Chothia (see above).

The immunoglobulin chains of antibodies ADI-12126 and ADI-12152 with the CDRs thereof indicated are set forth below. An "ADI-12126" antibody or antigen-binding fragment thereof comprises:

the light and heavy chain immunoglobulins of ADI-12126; or the light and heavy chain variable regions of ADI-12126; or the CDRs (CDR-L1, CDR-L2, CDR-L3 (CDR-H1, CDR-H2 and CDR-H3) of ADI-12126.

An "ADI-12152" antibody or antigen-binding fragment thereof comprises:

the light and heavy chain immunoglobulins of ADI-12152; or the light and heavy chain variable regions of ADI-12152; or the CDRs (CDR-L1, CDR-L2, CDR-L3 (CDR-H1, CDR-H2 and CDR-H3) of ADI-12152.

The term "ADI-12126" includes such antibodies and antigen-binding fragments comprising a heavy chain comprising the amino acid sequence of SEQ ID NO: 1 or 21, wherein the $X_1$ is Q or E; $X_2$ is M, G, L, S, T, Y, V or A; and/or wherein $X_3$ is M or L. ADI-12126 and ADI-12152 antibodies and antigen-binding fragments thereof are part of the present invention. The parental ADI-12126 antibody heavy chain has allele Q1/M115/M57, i.e., wherein $X_1$ is Q, $X_2$ is M and $X_3$ is M.

Mutations may be indicated using the format (parental residue)(position number)(mutant residue). Thus, for example, Q1E refers to mutation of Q at position 1 to E. Also, Q1 refers to the parental allele-Q at position 1. Residues at positions 1, 115 and 57 correspond to $X_1$, $X_2$ and $X_3$, respectively, in SEQ ID NO: 21 below.

Anti-LAG3 Antibody ADI-12126

```
ADI-12126 heavy chain:
X1VQLVQSGAEVKKPGASVKVSCKASGYTFTGYYMHWVRQAPGQGLEWMG

WINANSGX2TNYAQKFQGRVTMTRDTSISTAYMELSRLRSDDTAVYYCAR

DIYDSSDQLNVWGQGTX3VTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK
(SEQ ID NO: 21; wherein X1 is Q or E; X2 is M, G,
L, S, T, Y, V or A; and X3 is M or L)

ADI-12126 heavy chain variable region:
X1VQLVQSGAEVKKPGASVKVSCKASGYTFTGYYMHWVRQAPGQGLEWMG

WINANSGX2TNYAQKFQGRVTMTRDTSISTAYMELSRLRSDDTAVYYCAR

DIYDSSDQLNVWGQGTX3VTVSS
(SEQ ID NO: 1; wherein X1 is Q or E; X2 is G, L,
S, T, Y, V or A; and X3 is M or L)
```

-continued

CDR-H1:
(SEQ ID NO: 5)
GYTFTGYYMH

CDR-H2:
WINANSGX₂TNYAQKFQG
(SEQ ID NO: 6; wherein X₂ is M,G, L, S, T, Y,
V or A)

CDR-H3:
(SEQ ID NO: 7)
DIYDSSDQLNV;

In an embodiment of the invention, the heavy chain includes an N-terminal signal sequence, e.g., that comprises the amino acid sequence:

(SEQ ID NO: 49)
MEWSWVFLFFLSVTTGVHS.

ADI-12126 light chain:
(SEQ ID NO: 22)
EIVLTQSPATLSLSPGERATLSCRASQSVSSYLAWYQQKPGQAPRLLIYD
ASNRATGIPARFSGSGSGTDFTLTISSLEPEDFAVYYCQQASIWPLTEGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC ADI-12126 light chain variable region:
(SEQ ID NO: 2)
EIVLTQSPATLSLSPGERATLSCRASQSVSSYLAWYQQKPGQAPRLLIYD
ASNRATGIPARFSGSGSGTDFTLTISSLEPEDFAVYYCQQASIWPLTFGG
GTKVEIK

CDR-L1:
(SEQ ID NO: 8)
RASQSVSSYLA

CDR-L2:
(SEQ ID NO: 9)
DASNRAT

CDR-L3:
(SEQ ID NO: 10)
QQASIWPLT

In an embodiment of the invention, the light chain includes an N-terminal signal sequence, e.g., that comprises the amino acid sequence:

(SEQ ID NO: 48)
MSVPTQVLGLLLLWLTDARC.

The present invention includes the following anti-LAG3 antibodies and antigen-binding fragments:
ADI-12126 heavy chain (Q1, M57, M115 IgG4 S228P) (SEQ ID NO: 1 or 21, wherein $X_1$=Q, $X_2$=M and $X_3$=M) and ADI-12126 light chain Kappa;
ADI-12126 heavy chain (Q1E, M57G, M115L IgG4 S228P) (SEQ ID NO: 1 or 21, wherein $X_1$=E, $X_2$=G and $X_3$=L) and ADI-12126 light chain Kappa;
ADI-12126 heavy chain (Q1E, M57S, M115L IgG4 S228P) (SEQ ID NO: 1 or 21, wherein $X_1$=E, $X_{2=S}$ and $X_3$=L) and ADI-12126 light chain Kappa;
ADI-12126 heavy chain (Q1E, M57T, M115L IgG4 S228P) (SEQ ID NO: 1 or 21, wherein $X_1$=E, $X_2$=T and $X_3$=L) and ADI-12126 light chain Kappa;
ADI-12126 heavy chain (Q1E, M57Y, M115L IgG4 S228P) (SEQ ID NO: 1 or 21, wherein $X_1$=E, $X_2$=Y and $X_3$=L) and ADI-12126 light chain Kappa;
ADI-12126 heavy chain (Q1E, M57V, M115L IgG4 S228P) (SEQ ID NO: 1 or 21, wherein $X_1$=E, $X_2$=V and $X_3$=L) and ADI-12126 light chain Kappa;
ADI-12126 heavy chain (Q1E, M57A, M115L IgG4 S228P) (SEQ ID NO: 1 or 21, wherein $X_1$=E, $X_2$=A and $X_3$=L) and ADI-12126 light chain Kappa; or
ADI-12126 heavy chain (Q1E, M57, M115L IgG4 S228P) (SEQ ID NO: 1 or 21, wherein $X_1$=E, $X_2$=M and $X_3$=L) and ADI-12126 light chain Kappa.

Anti-LAG3 Antibody ADI-12152

ADI-12152 heavy chain:
X1VQLVQSGAEVKKPGASVKVSCKASGYTFQGYYMHWVRQAPGQGLEWMG
QINPHSGGTNYAQKFQGRVTMTRDTSISTAYMELSRLRSDDTAVYYCARD
RGEFDIAFDIWGQGTX2VTVSSASTKGPSVFPLAPCSRSTSESTAALGCL
VKDYFPEPVTVSWNSGALTSGVHTFPAVLQSSGLYSLSSVVTVPSSSLGT
KTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK
(SEQ ID NO: 51; wherein X1 is Q or E and X2 is M or L)
for example, ADI-12152 heavy chain:
(SEQ ID NO: 23)
QVQLVQSGAEVKKPGASVKVSCKASGYTFQGYYMHWVRQAPGQGLEWMGQ
INPHSGGTNYAQKFQGRVTMTRDTSISTAYMELSRLRSDDTAVYYCARDR
GEFDIAFDIWGQGTMVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK ADI-12152 heavy chain variable region:
X1VQLVQSGAEVKKPGASVKVSCKASGYTFQGYYMHWVRQAPGQGLEWMG
QINPHSGGTNYAQKFQGRVTMTRDTSISTAYMELSRLRSDDTAVYYCARD
RGEFDIAFDIWGQGTX2VTVSS
(SEQ ID NO: 52; wherein X1 is Q or E and X2 is M or L)
for example, ADI-12152 heavy chain variable region:
(SEQ ID NO: 3)
QVQLVQSGAEVKKPGASVKVSCKASGYTFQGYYMHWVRQAPGQGLEWMGQ
INPHSGGTNYAQKFQGRVTMTRDTSISTAYMELSRLRSDDTAVYYCARDR
GEFDIAFDIWGQGTMVTVSS -continued

CDR-H1:
(SEQ ID NO: 11)
GYTFQGYYMH

CDR-H2:
(SEQ ID NO: 12)
QINPHSGGTNYAQKFQG

CDR-H3:
(SEQ ID NO: 13)
DRGEFDIAFDI

In an embodiment of the invention, the heavy chain includes an N-terminal signal sequence, e.g., that comprises the amino acid sequence:

(SEQ ID NO: 49)
MEWSWVFLFFLSVTTGVHS.

ADI-12152 light chain:
(SEQ ID NO: 24)
DIQMTQSPSSLSASVGDRVTITCQASQDITNYLNWYQQKPGKAPKLLIYD
ASNLETGVPSRFSGSGSGTDFTFTISSLQPEDIATYYCQQVPPEPPYTEG
GGTKVEIKRTVAAPSVFIFPPSDEQLKSGTASVVCLLNNEYPREAKVQWK
VDNALQSGNSQESVTEQDSKDSTYSLSSTLTLSKADYEKHKVYACEVTHQ
GLSSPVTKSFNRGEC ADI-12152 light chain variable region:
(SEQ ID NO: 4)
DIQMTQSPSSLSASVGDRVTITCQASQDITNYLNWYQQKPGKAPKLLIYD
ASNLETGVPSRFSGSGSGTDFTFTISSLQPEDIATYYCQQVPPEPPYTEG
GGTKVEIK

CDR-L1:
(SEQ ID NO: 14)
QASQDITNYLN

CDR-L2:
(SEQ ID NO: 15)
DASNLET

CDR-L3:
(SEQ ID NO: 16)
QQVPPEPPYT

In an embodiment of the invention, the light chain includes an N-terminal signal sequence, e.g., that comprises the amino acid sequence:

(SEQ ID NO: 48)
MSVPTQVLGLLLLWLTDARC.

A "variant" of a polypeptide, such as an ADI-12126 or ADI-12152 immunoglobulin chain, refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment). Anti-LAG3 antibodies and antigen-binding fragments thereof of the present invention may comprise such variant immunoglobulin chains.

A "variant" of a polynucleotide refers to a polynucleotide comprising a nucleotide sequence that is at least about 70-99.9% (e.g., 80-99, 85-99, 90-99, 95-99, 70, 72, 74, 75, 76, 79, 80, 81, 82, 83, 84, 85, 86, 87, 88, 89, 90, 91, 92, 93, 94, 95, 96, 97, 98, 99, 99.5 or 99.9%) identical to a referenced nucleotide sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear). Anti-LAG3 antibodies and antigen-binding fragments thereof of the present invention may comprise immunoglobulin chains that are encoded by such variant polynucleotides.

In addition, a variant may be a polypeptide having sequence identity or homology to a heavy or light immunoglobulin chain or CDR of ADI-12126 or ADI-12152 or comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. Anti-LAG3 antibodies and antigen-binding fragments thereof of the present invention may comprise such variant immunoglobulin chains or CDRs.

As discussed herein, the present invention includes anti-LAG3 antibodies and antigen-binding fragments thereof that include one or more variants of the framework sequences (e.g., any one or more of FR-L1, FR-L2, FR-L3, FR-L4, FR-H1, FR-H2, FR-H3 and/or FR-H4), CDRs (e.g., 1, 2 or 3 variant CDR-Ls and/or 1, 2, or 3 variant CDR-Hs) and/or immunoglobulin chains (e.g., 1 or 2 variant $V_{LS}$ and/or 1 or 2 variant VHS) whose sequences are specifically set forth herein. Such antibodies and antigen-binding fragments may, themselves, be referred to as variants. Simple polypeptide chains, that include one or more variant FRs, CDR-Ls, CDR-Hs and/or immunoglobulin chains, themselves are also part of the present invention. Polynucleotides encoding such variant polypeptide chains are also part of the present invention.

The present invention includes anti-LAG3 antibodies and antigen-binding fragments wherein the CDRs are identical to those of the ADI-12126 or ADI-12152 $V_H$ and $V_L$ but having differences from such $V_H$ and $V_L$ that occur in the frameworks and/or immunoglobulin constant domains. For example, the present invention provides anti-LAG3 antibodies and antigen-binding fragments thereof that comprise variants of the ADI-12126 or ADI-12152 $V_H$ and/or $V_L$ chains set forth herein comprising the CDR-L1, CDR-L2, CDR-L3, CDR-H1, CDR-H2 and CDR-H3 of said $V_H$ of SEQ ID NO: 1 or 2 and $V_L$ of SEQ ID NO: 3 or 4 but comprising 70% or more (e.g., 80%, 85%, 90%, 95%, 97% or 99%) overall amino acid sequence identity or similarity to said $V_H$ of SEQ ID NO: 1 or 2 and $V_L$ of SEQ ID NO: 3 or 4, respectively.

Conservatively modified variants of ADI-12126 and ADI-12152 antibodies and antigen-binding fragments thereof are also part of the present invention. A "conservatively modified variant" or a "conservative substitution" refers to a variant wherein there is one or more substitutions of amino acids in a polypeptide with other amino acids having similar characteristics (e.g. charge, side-chain size, hydrophobicity/hydrophilicity, backbone conformation and rigidity, etc.).

Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to significantly disrupt biological activity. Variant anti-LAG3 antibodies or antigen-binding fragments of the present invention, which are discussed herein, comprise one or more CDRs (e.g., 1, 2 or 3 variant CDR-Ls and/or 1, 2, or 3 variant CDR-H); framework regions (e.g., any one or more of FR1, FR2, FR3 and/or FR4); and/or immunoglobulin chains having one or more conservative substitutions. For example, such antibodies and fragments may comprise the amino acid sequences disclosed herein, e.g., SEQ ID NOs: 1-16; wherein such amino acid sequences may comprise 1, 2, 3, 4, 5, 6, 7, 8, 9, 10, 12, 15, 20 or more conservative amino acid substitutions thereof. Exemplary conservative substitutions are set forth in Table 1.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln(Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the ADI-12126 and ADI-12152 antibodies and antigen-binding fragments thereof are also part of the present invention. Any of the variants of the ADI-12126 and ADI-12152 antibodies and antigen-binding fragments thereof (as discussed herein) may be "function-conservative variants". Such function-conservative variants may, in some cases, also be characterized as conservatively modified variants. "Function-conservative variants," as used herein, refers to variants of the ADI-12126 and ADI-12152 antibodies or antigen-binding fragments thereof in which one or more amino acid residues have been changed without significantly altering one or more functional properties of the antibody or fragment. In an embodiment of the invention, a function-conservative variant ADI-12126 and ADI-12152 antibody and antigen-binding fragments thereof of the present invention comprise a variant of an immunoglobulin chain and/or of a CDR of any of those set forth herein, e.g., any of SEQ ID NOs: 1-16; exhibiting one or more of the following functional properties:

Binds to human LAG3 with a $K_D$ of about 18 pM to about 25 pM (e.g., by Kinexa assay), for example, about 25 pM, 18 pM, 21 pM or 22 pM Binds to cynomolgous monkey LAG3 with a $K_D$ of about 43 pM to about 367 pM (e.g., by Kinexa assay), for example, about 43 pM, 126 pM, 367 pM or 48 pM.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The anti-LAG3 antibodies or antigen-binding fragments thereof of the present invention (e.g., antagonist antibodies) can comprise one, two, three, four, five, or six of the complementarity determining regions (CDRs) of the immunoglobulin chains disclosed herein (wherein 1, 2, 3, 4, 5 or 6 of the CDRs are, optionally, variants of those set forth herein). The one, two, three, four, five, or six CDRs may be independently selected from the CDR sequences of the various immunoglobulin chains disclosed herein. Alternatively, all CDRs may be selected from ADI-12126; or all CDRS may be selected from ADI-12152.

The anti-LAG3 antibodies or antigen-binding fragments thereof of the present invention can comprise at least one antibody heavy chain variable ($V_H$) domain comprising one or more (e.g., 3) of CDR-H1, CDR-H2 or CDR-H3 of ADI-12126 $V_H$ (e.g., SEQ ID NO: 1); e.g., wherein the CDRs comprise the amino acid sequences set forth in SEQ ID NOs: 5 (or a variant thereof having 1, 2, 3, 4, 5, 6, 7, 8, 9 or 10 point mutations and/or point deletions), 6 (or a variant thereof having 1, 2, 3, 4, 5, 6, 7, 8, 9 or 10 point mutations and/or point deletions), and 7 (or a variant thereof having 1, 2, 3, 4, 5, 6, 7, 8, 9 or 10 point mutations and/or point deletions), respectively.

The anti-LAG3 antibodies or antigen-binding fragments thereof of the present invention can comprise at least one antibody light chain variable ($V_L$) domain comprising one or more (e.g., 3) of CDR-L1, CDR-L2 and CDR-L3 of the ADI-12126 $V_L$ (e.g., SEQ ID NO: 3); e.g., wherein the CDRs comprise the amino acid sequences set forth in SEQ ID NOs: 8 (or a variant thereof having 1, 2, 3, 4, 5, 6, 7, 8, 9 or 10 point mutations and/or point deletions), 9 (or a variant thereof having 1, 2, 3, 4, 5, 6 or 7 point mutations and/or point deletions) and 10 (or a variant thereof having 1, 2, 3, 4, 5, 6, 7, 8 or 9 point mutations and/or point deletions), respectively.

The anti-LAG3 antibodies or antigen-binding fragments thereof of the present invention can comprise at least one antibody heavy chain variable ($V_H$) domain comprising one or more (e.g., 3) of CDR-H1, CDR-H2 or CDR-H3 of the ADI-12152 $V_H$ (e.g., SEQ ID NO: 2); e.g., wherein the CDRs comprise the amino acid sequences set forth in SEQ ID NOs: 11 (or a variant thereof having 1, 2, 3, 4, 5, 6, 7, 8, 9 or 10 point mutations and/or point deletions), 12 (or a variant thereof having 1, 2, 3, 4, 5, 6, 7, 8, 9 or 10 point mutations and/or point deletions) and 13 (or a variant thereof having 1, 2, 3, 4, 5, 6, 7, 8, 9 or 10 point mutations and/or point deletions), respectively.

The anti-LAG3 antibodies or antigen-binding fragments thereof of the present invention can comprise at least one antibody light chain variable ($V_L$) domain comprising one or more (e.g., 3) of CDR-L1, CDR-L2 and CDR-L3 of the ADI-12152 $V_L$ (e.g., SEQ ID NO: 4); e.g., wherein the CDRs comprise the amino acid sequences set forth in SEQ ID NOs: 14 (or a variant thereof having 1, 2, 3, 4, 5, 6, 7, 8, 9 or 10 point mutations and/or point deletions), 15 (or a variant thereof having 1, 2, 3, 4, 5, 6 or 7 point mutations and/or point deletions) and 16 (or a variant thereof having 1, 2, 3, 4, 5, 6, 7, 8, 9 or 10 point mutations and/or point deletions), respectively.

The present invention provides an anti-LAG3 antibody or antigen-binding fragment thereof that comprises:
the ADI-12126 CDR-H1, CDR-H2 and CDR-H3; and the ADI-12126 CDR-L1, CDR-L2 and CDRL3; or
the ADI-12152 CDR-H1, CDR-H2 and CDR-H3; and the ADI-12152 CDR-L1, CDR-L2 and CDRL3;
wherein, optionally, 1, 2, 3, 4, 5 or 6 of the CDRs are variants of those set forth herein.

The anti-LAG3 antibodies or antigen-binding fragments thereof of the present invention can comprise a heavy chain variable ($V_H$) domain comprising one or more (e.g., 3) of CDR-H1, CDR-H2 or CDR-H3 of ADI-12126 $V_H$ (e.g., SEQ ID NO: 1); e.g., wherein the CDRs comprise the amino acid sequences set forth in SEQ ID NOs: 5 (or a variant thereof having 1, 2, 3, 4, 5, 6, 7, 8, 9 or 10 point mutations and/or point deletions), 6 (or a variant thereof having 1, 2, 3, 4, 5, 6, 7, 8, 9 or 10 point mutations and/or point deletions), and 7 (or a variant thereof having 1, 2, 3, 4, 5, 6, 7, 8, 9 or 10 point mutations and/or point deletions), respectively; and a light chain variable ($V_L$) domain comprising one or more (e.g., 3) of CDR-L1, CDR-L2 and CDR-L3 of the ADI-12126 $V_L$ (e.g., SEQ ID NO: 3); e.g., wherein the CDRs comprise the amino acid sequences set forth in SEQ ID NOs: 8 (or a variant thereof having 1, 2, 3, 4, 5, 6, 7, 8, 9 or 10 point mutations and/or point deletions), 9 (or a variant thereof having 1, 2, 3, 4, 5, 6, 7 point mutations and/or point deletions) and 10 (or a variant thereof having 1, 2, 3, 4, 5, 6, 7, 8 or 9 point mutations and/or point deletions), respectively.

The anti-LAG3 antibodies or antigen-binding fragments thereof of the present invention can comprise a heavy chain variable ($V_H$) domain comprising one or more (e.g., 3) of CDR-H1, CDR-H2 or CDR-H3 of the ADI-12152 $V_H$ (e.g., SEQ ID NO: 2); e.g., wherein the CDRs comprise the amino acid sequences set forth in SEQ ID NOs: 11 (or a variant thereof having 1, 2, 3, 4, 5, 6, 7, 8, 9 or 10 point mutations and/or point deletions), 12 (or a variant thereof having 1, 2, 3, 4, 5, 6, 7, 8, 9 or 10 point mutations and/or point deletions) and 13 (or a variant thereof having 1, 2, 3, 4, 5, 6, 7, 8, 9 or 10 point mutations and/or point deletions), respectively; and a light chain variable ($V_L$) domain comprising one or more (e.g., 3) of CDR-L1, CDR-L2 and CDR-L3 of the ADI-12152 $V_L$ (e.g., SEQ ID NO: 4); e.g., wherein the CDRs comprise the amino acid sequences set forth in SEQ ID NOs: 14 (or a variant thereof having 1, 2, 3, 4, 5, 6, 7, 8, 9 or 10 point mutations and/or point deletions), 15 (or a variant thereof having 1, 2, 3, 4, 5, 6 or 7 point mutations and/or point deletions) and 16 (or a variant thereof having 1, 2, 3, 4, 5, 6, 7, 8, 9 or 10 point mutations and/or point deletions), respectively.

The present invention provides an anti-LAG3 antibody or antigen-binding fragment thereof or an immunoglobulin polypeptide that comprises:
the ADI-12126 $V_H$ immunoglobulin domain and/or the ADI-12126 $V_L$ immunoglobulin domain; or
the ADI-12152 $V_H$ immunoglobulin domain and/or the ADI-12152 $V_L$ immunoglobulin domain;
wherein, optionally, the $V_L$ and/or $V_H$ is a variant of a $V_L$ or $V_H$ that is set forth herein (e.g., SEQ ID NOs: 1-4).

The present invention further provides an anti-LAG3 antibody or antigen-binding fragment thereof that comprises the $V_L$ domain of ADI-12126 wherein the $V_L$ domain comprises the amino acid sequence of SEQ ID NO: 3 or a variant thereof.

The present invention further provides an anti-LAG3 antibody or antigen-binding fragment thereof that comprises the $V_H$ domain of ADI-12126 wherein the $V_H$ domain comprises the amino acid sequence of SEQ ID NO: 1; or a variant thereof.

The present invention further provides an anti-LAG3 antibody or antigen-binding fragment thereof that comprises the $V_L$ domain of ADI-12152 wherein the $V_L$ domain comprises the amino acid sequence of SEQ ID NO: 4 or a variant thereof.

The present invention further provides an anti-LAG3 antibody or antigen-binding fragment thereof that comprises the $V_H$ domain of ADI-12152 wherein the $V_H$ domain comprises the amino acid sequence of SEQ ID NO: 2; or a variant thereof.

The present invention further provides an anti-LAG3 antibody or antigen-binding fragment thereof that comprises the $V_L$ domain of ADI-12126 wherein the $V_L$ domain comprises the amino acid sequence of SEQ ID NO: 3 or a variant thereof; and the $V_H$ domain of ADI-12126 wherein the $V_H$ domain comprises the amino acid sequence of SEQ ID NO: 1; or a variant thereof.

The present invention further provides an anti-LAG3 antibody or antigen-binding fragment thereof that comprises the $V_L$ domain of ADI-12152 wherein the $V_L$ domain comprises the amino acid sequence of SEQ ID NO: 4 or a variant thereof; and the $V_H$ domain of ADI-12152 wherein the $V_H$ domain comprises the amino acid sequence of SEQ ID NO: 2; or a variant thereof.

The invention also provides polypeptides comprising the amino acid sequence set forth in SEQ ID NO: 1 or a variant thereof; or any polynucleotide encoding such a polypeptide.

The invention also provides polypeptides comprising the amino acid sequence set forth in SEQ ID NO: 2 or a variant thereof; or any polynucleotide encoding such a polypeptide.

The invention also provides polypeptides comprising the amino acid sequence set forth in SEQ ID NO: 3 or a variant thereof; or any polynucleotide encoding such a polypeptide.

The invention also provides polypeptides comprising the amino acid sequence set forth in SEQ ID NO: 4 or a variant thereof; or any polynucleotide encoding such a polypeptide.

The invention also provides polypeptides (e.g., a human immunoglobulin chain) comprising the CDR-H1, CDR-H2, and CDR-H3 of a $V_H$ domain comprising SEQ ID NO: 1; or any polynucleotide encoding such a polypeptide. Optionally, 1, 2 or 3 of such CDRs are variants of the sequence set forth herein. In an embodiment of the invention, the CDRs comprise the amino acid sequences set forth in SEQ ID NOs: 5-7, respectively.

The invention also provides polypeptides (e.g., a human immunoglobulin chain) comprising the CDR-H1, CDR-H2, and CDR-H3 of a $V_H$ domain comprising SEQ ID NO: 2; or any polynucleotide encoding such a polypeptide. Optionally, 1, 2 or 3 of such CDRs are variants of the sequence set forth herein. In an embodiment of the invention, the CDRs comprise the amino acid sequences set forth in SEQ ID NOs: 11-13, respectively.

The invention also provides polypeptides (e.g., a human immunoglobulin chain) comprising the CDR-L1, CDR-L2, and CDR-L3 of a $V_L$ domain comprising SEQ ID NO: 3; or any polynucleotide encoding such a polypeptide. Optionally, 1, 2 or 3 of such CDRs are variants of the sequence set forth herein. In an embodiment of the invention, the CDRs comprise the amino acid sequences set forth in SEQ ID NOs: 8-10, respectively.

The invention also provides polypeptides (e.g., a human immunoglobulin chain) comprising the CDR-L1, CDR-L2, and CDR-L3 of a $V_L$ domain comprising SEQ ID NO: 4; or any polynucleotide encoding such a polypeptide. Optionally, 1, 2 or 3 of such CDRs are variants of the sequence set forth herein. In an embodiment of the invention, the CDRs comprise the amino acid sequences set forth in SEQ ID NOs: 14-16, respectively.

The present invention includes crystalline compositions of the ADI-12126 and ADI-12152 anti-LAG3 antibodies and antigen-binding fragments thereof of the present invention.

Polynucleotides

The present invention further comprises the polynucleotides encoding any of the polypeptides or immunoglobulin chains of anti-LAG3 antibodies and antigen-binding fragments thereof disclosed herein (including variants of the amino acid chains specifically set forth herein). For example, the present invention includes the polynucleotides described in SEQ ID NOs: 17-20 and 47 and variants thereof (e.g., comprising nucleotide sequences having at least 70%, 80%, 90%, 95% or 99% BLAST sequence identity to such nucleotide sequences (as discussed above)); and polynucleotides encoding the amino acids described therein, e.g., in SEQ ID NOs: 1-4. The scope of the present invention also includes variant polynucleotides that hybridize to any of such polynucleotides.

In an embodiment of the invention the ADI-12126 heavy chain is encoded by a polynucleotide comprising the nucleotide sequence:

```
                                          (SEQ ID NO: 17)
ATGGAATGGAGCTGGGTGTTTCTGTTCTTCCTGTCCGTGACAACCGGCGT

GCACTCCCAGGTGCAGCTGGTGCAGTCCGGCGCTGAGGTCAAGAAACCTG

GCGCCAGCGTCAAAGTGAGCTGTAAGGCCTCCGGCTACACCTTTACCGGA

TACTACATGCACTGGGTCAGGCAGGCCCCTGGACAGGGACTGGAATGGAT

GGGCTGGATCAACGCTAACAGCGGAATGACCAACTACGCCCAGAAGTTCC

AGGGCCGGGTGACAATGACCCGGGACACCTCCATCAGCACCGCCTACATG

GAGCTGTCCCGGCTGAGGTCCGATGACACCGCTGTGTACTACTGCGCCCG

GGACATCTATGACTCCTCCGACCAGCTGAACGTGTGGGGCCAGGGCACAA

TGGTGACAGTGAGCTCCGCTTCCACCAAGGGCCCCAGCGTGTTTCCCCTG

GCTCCCTGCAGCAGGAGCACATCCGAGTCCACCGCTGCCCTGGGCTGTCT

GGTGAAGGACTACTTTCCTGAGCCTGTGACCGTGTCCTGGAATAGCGGCG

CCCTGACAAGCGGAGTGCACACATTCCCCGCTGTGCTCCAATCCTCCGGA

CTGTACAGCCTGAGCTCCGTCGTGACAGTGCCCAGCAGCAGCCTGGGCAC

CAAGACCTACACCTGCAACGTGGACCACAAGCCTTCCAACACCAAGGTGG

ACAAGAGGGTGGAGAGCAAGTACGGCCCCCCTTGTCCTCCTTGTCCTGCC

CCTGAGTTCCTCGGAGGACCCAGCGTGTTCCTGTTTCCTCCTAAACCCAA

GGACACCCTGATGATCTCCCGGACACCCGAAGTGACATGTGTGGTGGTGG

ACGTGTCCCAGGAAGACCCCGAGGTGCAGTTCAACTGGTACGTGGATGGC

GTGGAAGTGCATAACGCTAAGACCAAGCCCCGGGAAGAGCAGTTCAACAG

CACCTACAGGGTGGTGTCCGTGCTGACAGTGCTGCACCAGGACTGGCTGA

ATGGCAAAGAGTACAAGTGCAAGGTCAGCAACAAGGGCCTGCCCTCCTCC

ATCGAGAAGACCATCAGCAAGGCCAAGGGACAGCCTCGGGAGCCTCAGGT

GTACACCCTGCCCCCCTCCCAGGAGGAGATGACCAAGAACCAGGTCAGCC

TGACCTGCCTGGTGAAGGGCTTCTACCCCTCCGACATCGCCGTCGAGTGG

GAGTCCAACGGCCAGCCTGAGAATAACTACAAGACCACCCCCCCTGTCCT

GGACAGCGACGGTTCTTTCTTCCTGTACAGCAGGCTGACAGTGGACAAGT

CCAGGTGGCAGGAGGGCAACGTGTTCTCCTGCTCCGTGATGCACGAAGCC

CTGCACAATCACTATACCCAGAAGTCCCTCAGCCTGTCCCTCGGCAAATG

A
```

In an embodiment of the invention the ADI-12126 heavy chain is encoded by a polynucleotide comprising the nucleotide sequence:

```
                                          (SEQ ID NO: 47)
atggagtgga gctgggtctt cctgttctttt ctgtccgtca caaccggcgt gcactccgag gtccagctgg tgcagtccgg cgctgaggtg aagaaacccg gcgcttccgt gaaagtgagc tgcaaagcct ccggatacac cttcaccggc tactacatgc actgggtgag gcaggcccct ggacagggac tggagtggat
```

```
gggctggatc aacgccaaca gcggaggcac caactacgcc
cagaagttcc agggcagagt caccatgaca agggatacct
ccatcagcac cgcctacatg gagctgagca ggctgagaag
cgacgataca gccgtctact actgcgccag ggatatctac
gactccagcg accagctgaa tgtgtggggc cagggcacac
tggtgaccgt gagcagcgcc tccaccaagg gccctagcgt
gttccctctg gccccttgct ccagatccac atccgaatcc
acagccgccc tgggctgcct ggtgaaggac tatttccccg
agcccgtgac cgtgtcctgg aactccgagc cctgaccag
cggagtgcat accttcccg ccgtgctgca gtcctccgga
ctgtactccc tgagcagcgt ggtcaccgtg cccagcagca
gcctgggcac caagacctat acatgtaacg tggaccacaa
gcccagcaac accaaggtgg acaagagggt ggagagcaag
tacggacccc cttgccccc ctgtcccgcc cccgagttcc
tgggaggccc ctccgtgttt ctgttccccc ctaaacccaa
ggacaccctg atgatctcca ggacaccga agtgacctgt
gtggtggtgg acgtgtccca ggaagatcct gaggtgcagt
tcaattggta cgtcgacggc gtggaggtgc acaatgccaa
gaccaagcct agggaggagc agttcaactc cacctatagg
gtggtgagcg tgctgacagt gctgcaccaa gattggctga
acggaaagga atacaagtgc aaggtgtcca caagggcct
gcctagcagc atcgagaaaa ccatctccaa agctaagggc
cagcccagag aacctcaagt gtacaccctg cccccctccc
aggaagagat gaccaagaac caggtgagcc tcacctgtct
ggtgaaggga ttctacccca gcgacattgc cgtggagtgg
gaatccaatg gccagcctga gaacaattac aagaccacac
cccccgtgct ggacagcgat ggcagcttct ttctgtactc
caggctgacc gtggacaaga gcaggtggca ggagggcaat
gtgttctcct gcagcgtgat gcatgaggcc ctccacaatc
actacaccca gaagtccctg tccctcagcc tcggaaaatg a
```

In an embodiment of the invention the ADI-12126 light chain is encoded by a polynucleotide comprising the nucleotide sequence:

(SEQ ID NO: 18)
```
ATGTCCGTGCCCACCCAGGTGCTGGGACTGCTGCTGCTGTGGCTGACCGA
CGCCCGGTGTGAGATCGTGCTGACCCAGTCCCCCGCTACCCTGAGCCTGT
CCCCTGGAGAGAGGGCTACCCTGTCCTGTAGGGCCTCCCAGTCCGTGAGC
TCCTACCTGGCCTGGTACCAGCAGAAACCCGGCCAGGCTCCTAGGCTGCT
GATCTACGACGCCTCCAATAGGGCCACCGGCATTCCCGCTAGGTTCTCCG
GAAGCGGCTCCGGCACCGACTTCACCCTGACCATCTCCAGCCTGGAGCCC
GAGGACTTCGCTGTGTACTACTGCCAGCAGGCCAGCATCTGGCCCCTGAC
CTTCGGAGGCGGCACCAAGGTGGAGATCAAGAGGACCGTGGCCGCCCCTT
CCGTGTTCATCTTCCCCCCCTCCGATGAGCAGCTGAAGAGCGGCACCGCC
AGCGTGGTGTGCCTGCTGAACAACTTCTACCCCAGGGAGGCCAAGGTGCA
GTGGAAGGTGGACAACGCCCTGCAGAGCGGCAACTCCCAGGAGTCCGTGA
CAGAGCAGGACAGCAAGGACTCCACCTACAGCCTGAGCTCCACCCTGACC
CTGAGCAAGGCCGACTACGAAAAGCACAAGGTGTACGCCTGTGAGGTGAC
CCACCAGGGCCTGTCCTCCCCTGTGACCAAGTCCTTTAACAGGGGCGAGT
GCTGA
```

In an embodiment of the invention the ADI-12152 heavy chain is encoded by a polynucleotide comprising the nucleotide sequence:

(SEQ ID NO: 19)
```
ATGGAGTGGAGCTGGGTGTTCCTGTTTTTCCTGAGCGTCACCACAGGCGT
GCACTCCCAGGTCCAGCTGGTGCAGTCCGGAGCTGAGGTGAAGAAGCCTG
GAGCCTCCGTGAAGGTGTCCTGCAAGGCCTCCGGCTACACCTTCCAGGGC
TATTACATGCACTGGGTGAGGCAGGCTCCTGGACAGGGACTGGAGTGGAT
GGGCCAGATTAATCCCCACAGCGGAGGCACCAACTACGCCCAGAAGTTCC
AGGGCCGGGTGACAATGACACGGGACACCTCCATCAGCACAGCTTACATG
GAGCTGTCCAGGCTCAGGTCCGACGACACCGCCGTGTACTACTGCGCTCG
GGATCGGGGAGAGTTTGACATCGCCTTCGACATCTGGGGCCAGGGCACAA
TGGTGACAGTGAGCTCCGCCTCCACCAAGGGCCCTTCCGTGTTTCCCCTC
GCCCCCTGTAGCAGGTCCACATCCGAGTCCACAGCTGCCCTGGGCTGTCT
GGTGAAGGATTACTTCCCTGAGCCTGTGACAGTGAGCTGGAACAGCGGCG
CTCTGACCTCCGGCGTGCATACCTTTCCCGCCGTGCTGCAGTCCAGCGGA
CTGTACAGCCTGAGCTCCGTGGTGACAGTCCCCTCCTCCTCCCTGGGCAC
CAAAACCTACACCTGTAACGTGGACCACAAGCCCAGCAACACCAAGGTGG
ACAAGAGGGTGGAATCCAAGTACGGCCCTCCTTGTCCTCCTTGCCCCGCT
CCCGAGTTTCTGGGCGGACCTTCCGTGTTCCTGTTCCCTCCCAAGCCCAA
GGACACACTCATGATTAGCAGGACCCCCGAGGTCACATGTGTGGTGGTGG
ACGTGAGCCAGGAGGACCCCGAGGTCCAGTTCAACTGGTACGTGGATGGC
GTGGAGGTGCACAACGCTAAAACAAAGCCCCGGGAAGAACAGTTCAACAG
CACCTATCGGGTGGTGTCCGTGCTGACCGTGCTGCACCAGGACTGGCTGA
ATGGCAAGGAGTACAAGTGCAAAGTCAGCAACAAGGGCCTGCCTTCCAGC
ATCGAGAAGACCATCAGCAAGGCTAAGGGCCAGCCCAGGGAGCCTCAGGT
CTACACCCTCCCCCCTTCCCAGGAGGAGATGACAAAGAACCAGGTGTCCC
TCACCTGCCTGGTGAAGGGCTTCTACCCCAGCGACATCGCCGTGGAATGG
GAGTCCAACGGCCAGCCCGAGAATAACTACAAGACCACACCTCCTGTGCT
GGATTCCGATGGCAGCTTCTTTCTGTACTCCAGGCTGACCGTGGATAAGT
CCCGGTGGCAGGAGGGCAACGTCTTTAGCTGCAGCGTGATGCATGAGGCT
CTGCACAATCACTACACCCAGAAAAGCCTCAGCCTGTCCCTGGGCAAATG
A
```

In an embodiment of the invention the ADI-12152 light chain is encoded by a polynucleotide comprising the nucleotide sequence:

(SEQ ID NO: 20)
ATGTCCGTGCCCACCCAGGTGCTGGGACTGCTCCTGCTGTGGCTCACAGA

CGCCAGGTGCGACATCCAGATGACCCAGTCCCCCTCCTCCCTGTCCGCTT

CCGTGGGCGACAGGGTGACCATTACCTGCCAGGCCTCCCAGGACATCACC

AACTATCTGAACTGGTACCAGCAGAAGCCCGGCAAGGCCCCCAAACTGCT

GATCTACGACGCCTCCAACCTGGAGACCGGCGTGCCTTCCAGGTTCTCCG

GAAGCGGCAGCGGCACCGACTTCACCTTCACCATCTCCAGCCTGCAGCCC

GAGGACATCGCCACCTACTACTGCCAGCAGGTGCCTCCTGAGCCCCCCTA

CACCTTCGGAGGAGGCACCAAGGTGGAGATCAAGCGGACAGTGGCTGCTC

CCTCCGTCTTCATCTTCCCCCCCTCCGACGAGCAGCTGAAGAGCGGAACA

GCCTCCGTGGTGTGCCTCCTGAACAACTTCTACCCCCGGGAGGCCAAAGT

GCAGTGGAAGGTGGACAATGCCCTGCAGAGCGGCAACTCCCAGGAGTCCG

TCACCGAGCAGGACAGCAAGGATTCCACCTACAGCCTGTCCTCCACCCTG

ACCCTGTCCAAGGCCGATTACGAGAAGCACAAGGTGTACGCCTGCGAGGT

GACCCACCAGGGACTGTCCTCCCCCGTGACCAAGTCCTTCAACCGGGGCG

AGTGCTGA

Moreover, the present invention includes anti-LAG3 antibodies and antigen-binding fragments thereof comprising immunoglobulin heavy and light chains (e.g., variable regions thereof) and/or heavy and light chain CDRs encoded by the polynucleotides set forth herein.

For example, the present invention includes anti-LAG3 antibodies and antigen-binding fragments thereof comprising a heavy chain immunoglobulin encoded by a polynucleotide comprising the nucleotide sequence set forth in SEQ ID NO: 17, 19 or 47 (or encoding a variable domain thereof) and a light chain immunoglobulin encoded by the nucleotide sequence set forth in SEQ ID NO: 18 or 20 (or encoding a variable domain thereof).

The invention also provides polynucleotide comprising the nucleotide sequence set forth in SEQ ID NO: 17; or a variant thereof.

The invention also provides polynucleotide comprising the nucleotide sequence set forth in SEQ ID NO: 18; or a variant thereof. The invention also provides polynucleotide comprising the nucleotide sequence set forth in SEQ ID NO: 19; or a variant thereof.

The invention also provides polynucleotides comprising the nucleotide sequence set forth in SEQ ID NO: 20; or a variant thereof.

The invention also provides polynucleotide comprising the nucleotide sequence set forth in SEQ ID NO: 47; or a variant thereof.

Variant polynucleotides set forth herein include those that hybridize under low, moderate or high stringency conditions to the polynucleotides set forth herein or to polynucleotides that encode the polypeptides set forth herein, and encode immunoglobulin chains of anti-LAG3 antibodies or antigen-binding fragments thereof which maintain the ability to specifically bind to LAG3 (human and/or cynomolgous monkey, e.g., *Macaca fascicularis* or *Macaca mulatta*). A first polynucleotide molecule is "hybridizable" to a second polynucleotide molecule when a single stranded form of the first polynucleotide molecule can anneal to the second polynucleotide molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two polynucleotide contain complementary sequences, although, depending on the stringency of the hybridization, mismatches between bases are possible. The appropriate stringency for hybridizing polynucleotides depends on the length of the polynucleotides and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter polynucleotides, e.g., oligonucleotides, the position of mismatches becomes more important, and the length of the oligonucleotide determines its specificity (see Sambrook, et al., supra, 11.7-11.8).

In another embodiment of the invention, a polynucleotide, for example DNA, encoding the immunoglobulin polypeptide chains of the anti-LAG3 antibodies or antigen-binding fragments set forth herein forms part of the present invention. In one embodiment, the polynucleotide encodes at least one immunoglobulin polypeptide light chain variable ($V_L$) domain and at least one immunoglobulin polypeptide heavy chain variable ($V_H$) domain, wherein the $V_L$ domain comprises a CDR-L1, CDR-L2 and CDR-L3 having the amino acid sequence set forth in SEQ ID NOs: 8-10, respectively or 14-16, respectively; and the $V_H$ domain comprises CDR-H1, CDR-H2 and CDR-H3 having the amino acid sequence set forth in SEQ ID NOs: 5-7, respectively or SEQ ID NOs: 11-13, respectively. In one embodiment, the nucleic acid encodes the ADI-12126 or ADI-12152 light chain variable region and/or the ADI-12126 or ADI-12152 heavy chain variable region sequences. In some embodiments of the invention, the polynucleotide encodes both a light chain and a heavy chain on a single polynucleotide molecule, and, in other embodiments of the invention, the light and heavy chains are encoded on separate polynucleotide molecules, e.g., in separate or common host cells. In another embodiment the polynucleotides further encodes a signal sequence.

In one embodiment of the invention, the polynucleotide encodes a ADI-12126 immunoglobulin light chain variable ($V_L$) domain comprising the CDR-L1, CDR-L2 and CDR-L3 of SEQ ID NOs: 8-10, respectively. Variants of such polynucleotides are also part of the present invention.

In one embodiment of the invention, the polynucleotide encodes a ADI-12152 immunoglobulin light chain variable ($V_L$) domain comprising the CDR-L1, CDR-L2 and CDR-L3 of SEQ ID NOs: 14-16, respectively. Variants of such polynucleotides are also part of the present invention.

In one embodiment of the invention, the polynucleotide encodes a ADI-12126 immunoglobulin heavy chain variable ($V_H$) domain comprising the CDR-H1, CDR-H2 and CDR- H3 of SEQ ID NOs: 5-7, respectively. Variants of such polynucleotides are also part of the present invention.

In one embodiment of the invention, the polynucleotide encodes a ADI-12152 immunoglobulin heavy chain variable ($V_H$) domain comprising the CDR-H1, CDR-H2 and CDR-H3 of SEQ ID NOs: 11-13, respectively. Variants of such polynucleotides are also part of the present invention.

In one embodiment of the invention, the polynucleotide encodes the immunoglobulin light chain variable ($V_L$) domain of SEQ ID NO: 3. Variants of such polynucleotides are also part of the present invention.

In one embodiment of the invention, the polynucleotide encodes the immunoglobulin light chain variable ($V_L$) domain of SEQ ID NO: 4. Variants of such polynucleotides are also part of the present invention.

In one embodiment of the invention, the polynucleotide encodes the immunoglobulin heavy chain variable ($V_H$) domain of SEQ ID NO: 1. Variants of such polynucleotides are also part of the present invention.

In one embodiment of the invention, the polynucleotide encodes the immunoglobulin heavy chain variable ($V_H$) domain of SEQ ID NO: 2. Variants of such polynucleotides are also part of the present invention.

This present invention also provides vectors, e.g., expression vectors, such as plasmids, comprising the polynucleotides of the invention (sequences set forth herein and variants thereof, e.g., SEQ ID NO: 17-20 or 47), wherein the polynucleotide may be operably linked to control sequences, such as a promoter, that are recognized by a host cell when the host cell is transfected with the vector. Also provided are host cells comprising a polynucleotide (e.g., integrated into the genome, e.g., a chromosome, of the host cell or ectopic in the host cell) or vector of the present invention. As discussed below, methods for producing the antibody or antigen-binding fragment thereof or polypeptide disclosed herein are part of the present invention.

Binding Affinity

By way of example, and not limitation, the anti-LAG3 antibodies and antigen-binding fragments thereof disclosed herein bind LAG3 e.g., with a μD value of at least about 100 nM ($1 \times 10^{-7}$ M); at least about 10 nM; or at least about 1 nM. In further embodiments, the antibodies have μD values of at least about 200 pM ($2 \times 10^{-10}$ M), 100 pM, 50 pM, 20 pM, 10 pM, 5 pM or even 2 pM. For example, the μD is about $2.77 \times 10^{12}$M, $1.47 \times 10^{11}$M, $1.47 \times 10^{i9}$M, or $9.03 \times 10^{11}$ M; or a higher affinity. In an embodiment of the invention, the μD is as measured in a KinExA assay or similar kinetic exclusion assay. See e.g., Darling et al. *Assay and Drug Dev. Tech.* 2(6): 647-657 (2004).

Methods of Making Antibodies and Antigen-Binding Fragments Thereof

The anti-LAG3 antibodies disclosed herein may also be produced recombinantly (e.g., in an *E. coli*/T7 expression system). In this embodiment, nucleic acids encoding the anti-LAG3 antibody immunoglobulin molecules of the invention (e.g., $V_H$ or $V_L$; e.g., any one or more of SEQ ID NO: 1-4 or 21-24) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-LAG3 antibody or antigen-binding fragment thereof of the present invention (e.g., ADI-12126 or ADI-12152), or an immunoglobulin chain thereof, comprising (i) introducing a polynucleotide encoding one or more immunoglobulin chains of the antibody or fragment e.g., heavy chain immunoglobulin of ADI-12126 or ADI-12152; e.g., SEQ ID NOs: 1 or 3 and/or light chain immunoglobulin of e.g., ADI-12126 or ADI-12152; e.g., SEQ ID NO: 2 or 4, for example, wherein the polynucleotide is in a vector and/or is operably linked to a promoter;

(ii) culturing the host cell (e.g., CHO or *Pichia* or *Pichia pastoris*) under condition favorable to expression of the polynucleotide and, (iii) optionally, isolating the antibody or fragment or chain from the host cell and/or medium in which the host cell is grown.

In an embodiment of the invention, the polypeptide, antibodies or antigen-binding fragments expressed by the host cell are secreted from the host cell into the culture medium. In an embodiment of the invention, the secreted polypeptides or immunoglobulin chains are expressed with a secretion signal sequence that directs secretion of the expressed product from the cell. In an embodiment of the invention, such a method comprises introducing the polynucleotide or vector in the host cell, e.g., by transformation or transfection.

When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. Such methods are part of the present invention. The methods of the present invention include those wherein only a heavy immunoglobulin chain or only a light immunoglobulin chain is expressed. Such chains are useful, for example, as intermediates in the expression of an antibody or antigen-binding fragment that includes such a chain. The present invention also includes anti-LAG3 antibodies and antigen-binding fragments thereof comprising a heavy chain immunoglobulin and a light chain immunoglobulin which are the products of such production methods, and, optionally, the purification methods set forth herein.

Anti-LAG3 antibodies can also be synthesized by any of the methods set forth in U.S. Pat. No. 6,331,415.

Eukaryotic and prokaryotic host cells, including mammalian cells as hosts for expression of the anti-LAG3 antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp., *Yarrowia hpolytica*, and *Neurospora crassa*.

Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-LAG3 antibody or antigen-binding fragment thereof of the present invention comprising introducing a sample (e.g., culture medium, cell lysate or cell lysate fraction, e.g., a soluble fraction of the lysate) comprising the antibody or fragment to a purification medium and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the antibody or fragment is secreted into the culture medium by the host cell and the medium or a fraction thereof is applied to the purification medium. In an embodiment of the invention, the purification medium is a cation-exchange medium, anion-exchange medium, hydrophobic exchange medium, size exchange chromatography medium and/or an affinity purification medium (e.g., protein-A, protein-G, protein-A/G, protein-L).

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

The present invention includes anti-LAG3 antibodies and antigen-binding fragments thereof (e.g., ADI-12126 or ADI-12152) comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the antibody or antigen-binding fragment comprises one or more of the "engineered yeast N-linked glycans" or "CHO N-linked glycans" that are set forth in FIG. 1 (e.g., G0 and/or G0-F and/or G1 and/or G1-F and/or G2-F and/or Man5). In an embodiment of the invention, the antibody or antigen-binding fragment comprises the engineered yeast N-linked glycans, i.e., G0 and/or G1 and/or G2, optionally, further including Man5. In an embodiment of the invention, the antibody or antigen-binding fragment comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the antibody or antigen-binding fragment immunoglobulin chains are engineered yeast N-linked glycans or CHO N-linked glycans. See Nett et al. *Yeast.* 28(3): 237-252 (2011); Hamilton et al. *Science.* 313(5792): 1441-1443 (2006); Hamilton et al. *Curr Opin Biotechnol.* 18(5): 387-392 (2007). For example, in an embodiment of the invention, an engineered yeast cell is GFI5.0 or YGLY8316 or strains set forth in U.S. Pat. No. 7,795,002 or Zha et al. *Methods Mol Biol.* 988:31-43 (2013). See also international patent application publication no. WO2013/066765.

The present invention includes polyclonal anti-LAG3 antibodies and antigen-binding fragments thereof, e.g., a composition comprising a plurality of anti-LAG3 antibodies and fragments, which include one or more of the antibodies or antigen-binding fragments thereof of the present invention (e.g., ADI-12126 or ADI-12152), and methods of use thereof. A polyclonal antibody is an antibody which was produced among or in the presence of one or more other, non-identical antibodies. In general, polyclonal antibodies are produced from collections of different B-lymphocytes, e.g., the B-lymphocyte of an animal treated with an immunogen of interest, which produces a population of different antibodies but which are all directed to the immunogen. Usually, polyclonal antibodies are obtained directly from an immunized animal, e.g., spleen, serum or ascites fluid.

The present invention further includes anti-LAG3 antigen-binding fragments of the antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a V$_L$-C$_L$ chain appended to a V$_H$-C$_{H1}$ chain by a disulfide bridge. A F(ab)$_2$ fragment is two Fab fragments which, in turn, are appended by two disulfide bridges. The Fab portion of an F(ab)$_2$ molecule includes a portion of the Fc region between which disulfide bridges are located. An F$_V$ fragment is a V$_L$ or V$_H$ region.

Antibody Engineering of the Fc Region

The anti-LAG3 antibodies and antigen-binding fragments thereof disclosed herein (e.g., ADI-12126 or ADI-12152) may also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies and antigen-binding fragments thereof (e.g., ADI-12126 or ADI-12152) can be chemically modified (e.g., one or more chemical moieties can be attached to the antibody) or be modified to alter its glycosylation, again to alter one or more functional properties of the antibody or fragment. Each of these embodiments is described in further detail below. The numbering of residues in the Fc region is that of the EU index of Kabat. Any such anti-LAG3 antibody or antigen-binding fragment thereof having the modifications (e.g., Fc modifications) and/or alterations discussed herein are part of the present invention.

The anti-LAG3 antibodies and antigen-binding fragments thereof disclosed herein (e.g., ADI-12126 or ADI-12152) also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. See Presta (2005) *J. Allergy Clin. Immunol.* 116:731 at 734-35.

In one embodiment, the anti-LAG3 antibody or antigen-binding fragment (e.g., ADI-12126 or ADI-12152) is an IgG4 isotype antibody or fragment comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an anti-LAG3 antibody or antigen-binding fragment (e.g., ADI-12126 or ADI-12152) is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the anti-LAG3 antibody or antigen-binding fragment (e.g., ADI-12126 or ADI-12152) is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the anti-LAG3 antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the anti-LAG3 antibody or antigen-binding fragment has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the anti-LAG3 antibody or antigen-binding fragment thereof to fix complement. This approach is described further in PCT Publication WO94/29351.

In yet another example, the Fc region is modified to decrease the ability of the anti-LAG3 antibody or antigen-binding fragment (e.g., ADI-12126 or ADI-12152) to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604).

In one embodiment of the invention, the Fc region is modified to decrease the ability of the anti-LAG3 antibody or antigen-binding fragment (e.g., ADI-12126 or ADI-12152) to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

In still another embodiment, the anti-LAG3 antibody or antigen-binding fragment (e.g., ADI-12126 or ADI-12152) comprises a particular glycosylation pattern. For example, an aglycosylated antibody or fragment can be made (i.e., the antibody lacks glycosylation) and such antibodies and fragments are part of the present invention. The glycosylation pattern of an antibody or fragment may be altered to, for example, increase the affinity or avidity of the antibody or fragment for a LAG3 antigen. Such modifications can be accomplished by, for example, altering one or more of the glycosylation sites within the antibody or fragment sequence. For example, one or more amino acid substitutions can be made that result removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Anti-LAG3 antibodies and antigen-binding fragments disclosed herein (e.g., ADI-12126 or ADI-12152) include those produced in lower eukaryote host cells, in particular fungal host cells such as yeast (e.g., *Pichia pastoris*) and filamentous fungi, that have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the anti-LAG3 antibodies and antigen-binding fragments thereof disclosed herein (e.g., ADI-12126 or ADI-12152) further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the anti-LAG3 antibodies and antigen-binding fragments thereof provided herein (e.g., ADI-12126 or ADI-12152) may comprise antibodies or fragments having at least one hybrid N-glycan selected from the group consisting of $GlcNAcMan_5GlcNAc_2$; $GalGlcNAcMan_5GlcNAc2$; and $NANAGalGlcNAcMan_5GlcNAc2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the anti-LAG3 antibodies and antigen-binding fragments thereof provided herein (e.g., ADI-12126 or ADI-12152) comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the anti-LAG3 antibody and antigen-binding fragment N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc_{1-2})Man_3GlcNAc_2$, $NANAGal_2GlcNAc_2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects, the anti-LAG3 antibodies or antigen-binding fragments thereof comprise high mannose N-glycans, including but not limited to, $Man_8GlcNAc_2$, $Man_7GlcNAc_2$, $Man_6GlcNAc_2$, $Man_5GlcNAc_2$, $Man_4GlcNAc_2$, or N-glycans that consist of the $Man_3GlcNAc_2$ N-glycan structure.

In further aspects of the above, the complex N-glycans further include fucosylated and non-fucosylated bisected and multiantennary species.

In an embodiment of the invention, an anti-LAG3 antibody or antigen-binding fragment thereof (e.g., ADI-12126 or ADI-12152) comprises an immunoglobulin Fc domain that comprises glycans that comprise sialic acid (e.g., N-Acetylneuraminic acid), e.g., terminal α2,3-sialic acid or terminal α2,6-sialic acid. In an embodiment of the invention, the glycans on the Fc are 5, 10, 20, 50, 90% or more sialylated species. In an embodiment of the invention, the Fc comprises the mutations at positions 297, 264 and/or 243.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The anti-LAG3 antibodies and antigen-binding fragments thereof disclosed herein (e.g., ADI-12126 or ADI-12152) may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence.

Each anti-LAG3 antibody or antigen-binding fragment (e.g., ADI-12126 or ADI-12152) will have a characteristic melting temperature, with a higher melting temperature indicating greater overall stability in vivo (Krishnamurthy R and Manning M C (2002) Curr Pharm Biotechnol 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, anti-LAG3 antibodies and antigen-binding fragments thereof (e.g., ADI-12126 or ADI-12152) are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, anti-LAG3 antibodies and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

Antibody Conjugates

The anti-LAG3 antibodies and antigen-binding fragments thereof disclosed herein (e.g., ADI-12126 or ADI-12152) may also be conjugated to a chemical moiety. Such conjugated antibodies and fragments are part of the present invention. The chemical moiety may be, inter alia, a polymer, a polypeptide, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The anti-LAG3 antibodies and antigen-binding fragments thereof disclosed herein (e.g., ADI-12126 or ADI-12152) may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, ruthenium, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The anti-LAG3 antibodies and antigen-binding fragments disclosed herein (e.g., ADI-12126 or ADI-12152) may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The anti-LAG3 antibodies and antigen-binding fragments disclosed herein (e.g., ADI-12126 or ADI-12152) may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The anti-LAG3 antibodies and antigen-binding fragments thereof (e.g., ADI-12126 or ADI-12152) may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, Phytoiacca americana proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the anti-LAG3 antibodies and antigen-binding fragments thereof (e.g., ADI-12126 or ADI-12152) to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies and fragments are conventional and very well known in the art.

Therapeutic Uses

Further provided are methods for treating or preventing cancer in subjects, such as human subjects, in need of such treatment by administering an effective amount of the anti-LAG3 antibodies or antigen-binding fragments thereof of the present invention which are disclosed herein (e.g., ADI-12126 or ADI-12152) which may be effective for such treatment or prevention. In an embodiment of the invention, such a subject suffers from and is treated for cancer, e.g., a solid tumor which includes, in addition to the tumor cells, tumor infiltrating lymphocytes (TILs), such as T-cells, expressing LAG3. In an embodiment of the invention, the cancer is osteosarcoma, rhabdomyosarcoma, neuroblastoma, kidney cancer, leukemia, renal transitional cell cancer, bladder cancer, Wilm's cancer, ovarian cancer, pancreatic cancer, breast cancer (e.g., characterized by a mutation in BRCA1 and/or BRCA2), prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

The present invention also provides methods for treating or preventing an infectious disease in a subject by administering an effective amount of anti-LAG3 antibodies or antigen-binding fragments thereof disclosed herein (e.g., ADI-12126 or ADI-12152) to the subject which may be effective for such treatment or prevention. In an embodiment of the invention, the infectious disease is viral infection. In an embodiment of the invention, the infectious disease is bacterial infection. In an embodiment of the invention, the infectious disease is parasitic infection. In an embodiment of the invention, the infectious disease is fungal infection.

The present invention includes methods of treating any of the cancers or infectious diseases discussed herein by administering a therapeutically effective amount of an anti-LAG3 antibody or antigen-binding fragment thereof (e.g., ADI-12126 or ADI-12152) optionally in association with any of the further therapeutic agents or therapeutic procedures discussed herein as well as compositions including such an antibody or fragment in association with such a further therapeutic agent.

In an embodiment of the invention, the viral infection is infection with a virus selected from the group consisting of human immunodeficiency virus (HIV), ebola virus, hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment of the invention, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium* diphtherias, *Salmonella*, bacilli, *Vibrio cholerae, Clostridium tetan, Clostridium botulinum, Bacillus anthricis, Yersinia pestis, Mycobacterium leprae, Mycobacterium lepromatosis,* and *Borriella*.

In an embodiment of the invention, the fungal infection is infection with a fungus selected from the group consisting of *Candida (albicans, krusei, glabrata, tropicalis,* etc.), *Cryptococcus neoformans, Aspergillus (fumigatus, niger,* etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

In an embodiment of the invention, the parasitic infection is infection with a parasite selected from the group consisting of *Entamoeba histolytica, Balantidium coli, Naegleria fowleri, Acanthamoeba, Giardia* Zambia, *Cryptosporidium, Pneumocystis carinii, Plasmodium vivax, Babesia microti, Trypanosoma brucei, Trypanosoma cruzi, Leishmania donovani, Toxoplasma gondii, Nippostrongylus brasiliensis*.

In addition, the present invention provides a method for preventing or inhibiting LAG3 binding to WIC class II, enhancing antigen-specific T-cell activation or stimulating T-cell production of interleukin-2 in a subject (e.g., human), for example, wherein the subject suffers from cancer or infectious disease (e.g., as discussed herein) comprising administering an effective amount of anti-LAG3 antibody or antigen-binding fragment thereof (e.g., ADI-12126 or ADI-12152, to the subject, optionally, in association with a further therapeutic agent, e.g., pembrolizumab or nivolumab.

The scope of the present invention provides uses of the anti-LAG3 antibodies or antigen-binding fragments thereof disclosed herein (e.g., ADI-12126 or ADI-12152) in the manufacture of a medicament for treating cancer or infectious disease in a subject; as well as uses of the anti-LAG3 antibodies or antigen-binding fragments thereof disclosed herein (e.g., ADI-12126 or ADI-12152) for the treatment or prevention of cancer or infection disease in a subject.

The present invention includes methods for treating or preventing osteosarcoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing rhabdomyosarcoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing neuroblastoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing kidney cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing leukemia comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing renal transitional cell cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing bladder cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing Wilm's cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing ovarian cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing pancreatic cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing breast cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing breast cancer comprises administering an effective amount of an anti-LAG3 antibody or antigen-binding fragment thereof of the present invention in association with an anthracycline (e.g., doxorubicin and/or epirubicin) and/or a taxane (e.g., paclitaxel and/or docetaxel). Optionally, an anthracycline and taxane is in association with 5-fluorouracil (5-FU), cyclophosphamide, and carboplatin. In an embodiment of the invention, wherein the breast cancer is HER2 positive, the anti-LAG3 antibody or fragment is administered in association with trastuzumab, optionally with a taxane and/or pertuzumab.

The present invention includes methods for treating or preventing prostate cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing bone cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing lung cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing lung cancer comprises administering an effective amount of an anti-LAG3 antibody or antigen-binding fragment thereof of the present invention in association with bevacizumab and/or cetuximab.

The present invention includes methods for treating or preventing non-small cell lung cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing non-small cell lung cancer comprises administering an effective amount of an anti-LAG3 antibody or antigen-binding fragment thereof of the present invention in association with cisplatin, carboplatin, paclitaxel, albumin-bound paclitaxel, docetaxel, gemcitabine, vinorelbine, irinotecan, etoposide, vinblastine, and/or pemetrexed.

The present invention includes methods for treating or preventing gastric cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing colorectal cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing colorectal cancer comprises administering an effective amount of an anti-LAG3 antibody or antigen-binding fragment thereof of the present invention in association with 5-Fluorouracil (5-FU), capecitabine, irinotecan and/or oxaliplatin (e.g., FOLFOX, FOLFIRI, FOLFOXIRI or CapeOx).

The present invention includes methods for treating or preventing cervical cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing synovial sarcoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing head and neck cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing squamous cell carcinoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing multiple myeloma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing renal cell cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing retinoblastoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing hepatoblastoma comprising administering (optionally in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing hepatocellular carcinoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing melanoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing rhabdoid tumor of the kidney comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing Ewing's sarcoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing chondrosarcoma comprising administering (optionally in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing brain cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing glioblastoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing glioblastoma multiforme comprises administering an effective amount of an anti-LAG3 antibody or antigen-binding fragment thereof of the present invention in association with temozolomide.

The present invention includes methods for treating or preventing meningioma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing pituitary adenoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing vestibular schwannoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing a primitive neuroectodermal tumor comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing medulloblastoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing astrocytoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing anaplastic astrocytoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof. In an embodiment of the invention, the method for treating or preventing refractory anaplastic astrocytoma comprises administering an effective amount of an anti-LAG3 antibody or antigen-binding fragment thereof of the present invention in association with temozolomide.

The present invention includes methods for treating or preventing oligodendroglioma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing ependymoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing choroid plexus papilloma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing polycythemia vera comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing thrombocythemia comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing idiopathic myelfibrosis comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing soft tissue sarcoma comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing thyroid cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing endometrial cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing carcinoid cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing liver cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing breast cancer (e.g., characterized by a mutation in BRCA/and/or BRCA2) comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing gastric cancer comprising administering (optionally, in association with pembrolizumab or nivolumab) an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with human immunodeficiency virus (HIV) in a subject comprising administering) an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent such as a protease inhibitor, a nucleoside/nucleotide reverse transcriptase inhibitor, a non-nucleoside reverse transcriptase inhibitors, an entry inhibitor, a fusion inhibitor or an integrase inhibitors.

The present invention includes methods for treating or preventing an infection with Bundibugyo virus (BDBV), Sudan virus (SUDV), Tai Forest virus (TAFV) and/or ebola virus in a subject comprising administering) an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent, such as one or more antibodies that specifically bind to the BDBV, SUDV, TAFV or ebola virus or a nucleoside RNA polymerase inhibitor; or a vaccine.

The present invention includes methods for treating or preventing an infection with hepatitis A virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with hepatitis B virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with hepatitis C virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent such as interferon and/or ribavirin.

The present invention includes methods for treating or preventing an infection with herpes virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with vesicular stomatitis virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with herpes simplex virus-I in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with HAV-6 virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with herpes simplex virus-II in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with cytomegalovirus (CMV) in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with epstein Barr virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with adenovirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with influenza virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with flavivirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with echovirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with rhinovirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with coxsackie virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with coronavirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with respiratory syncytial virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with mumps virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with rotavirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with measles virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with rubella virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with parvovirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with vaccinia virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with human T-lymphotropic virus (HTLV) in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with dengue virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with papillomavirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with molluscum virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with poliovirus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with rabies virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with John Cunningham virus (JC virus) in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with arboviral encephalitis virus in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-viral therapeutic agent.

The present invention includes methods for treating or preventing an infection with Chlamydia trachomatis in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *rickettsia* bacteria in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with mycobacteria in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with staphylococci in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with streptococci in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with pneumonococci in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with meningococci in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with gonococci in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *klebsiella* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *proteus* (e.g., *P. vulgaris, P. mirabilis*, or *P. penneri*) in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *serratia* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *pseudomonas* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *legionella* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Corynebacterium diphtheriae* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Salmonella* (e.g., *Salmonella bongori* or *Salmonella enterica*) in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with bacilli in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Vibrio cholerae* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Clostridium tetani* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Clostridium botulinum* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Bacillus anthracis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Yersinia pestis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Leptospira* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Borrelia* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-bacterial antibiotic.

The present invention includes methods for treating or preventing an infection with *Candida albicans* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Candida krusei* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Candida glabrata* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Candida tropicalis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Cryptococcus neoformans* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Aspergillus fumigatus* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Aspergillus niger* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Mucorales mucor* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Mucorales absidia* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Mucorales rhizopus* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Sporothrix schenkii* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Blastomyces dermatitidis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Paracoccidioides brasihensis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Coccidioides immitis* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Histoplasma capsulatum* in a subject comprising administering an effective amount of an anti-LAG3 antibody or antigen-binding fragment thereof of the present invention (e.g., ADI-12126 or ADI-12152) to a subject, such as a human, in need thereof. Optionally, the subject is administered an anti-fungal therapeutic agent.

The present invention includes methods for treating or preventing an infection with *Entamoeba histolytica* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Balantidium coli* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Naegleria fowleri* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Acanthamoeba* sp. in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with Giardia Zambia in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Cryptosporidium* sp. in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Pneumocystis carinii* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Plasmodium vivax* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Babesia microti* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Trypanosoma brucei* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Trypanosoma cruzi* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Leishmania donovani* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with *Toxoplasma gondii* in a subject comprising administering an effective amount of an anti-LAG3 antibody or antigen-binding fragment thereof of the present invention (e.g., ADI-12126 or ADI-12152) to a subject, such as a human, in need thereof.

The present invention includes methods for treating or preventing an infection with Nippostrongylus *brasiliensis* in a subject comprising administering an effective amount of an anti-LAG3 antibody or antigen-binding fragment thereof of the present invention (e.g., ADI-12126 or ADI-12152) to a subject, such as a human, in need thereof.

A "subject" is a mammal such as, for example, a human, dog, cat, horse, cow, mouse, rat, monkey (e.g., cynomolgous monkey, e.g., *Macaca fascicularis* or *Macaca* mulatta) or rabbit.

In particular embodiments, the anti-LAG3 antibodies or antigen-binding fragments thereof of the present invention which are disclosed herein (e.g., ADI-12126 or ADI-12152) may be used alone, or in association with other, further therapeutic agents and/or therapeutic procedures, for treating or preventing any disease such as cancer, e.g., as discussed herein, in a subject in need of such treatment or prevention. Compositions or kits, e.g., pharmaceutical compositions comprising a pharmaceutically acceptable carrier, comprising such antibodies and fragments in association with further therapeutic agents are also part of the present invention.

In particular embodiments, the anti-LAG3 antibodies or antigen-binding fragments thereof of the present invention (e.g., ADI-12126 or ADI-12152) may be used in association with an anti-cancer therapeutic agent or immunomodulatory drug such as an immunomodulatory receptor inhibitor, e.g., an antibody or antigen-binding fragment thereof that specifically binds to the receptor.

In an embodiment of the invention, an anti-LAG3 antibody or antigen-binding fragment thereof of the present invention (e.g., ADI-12126 or ADI-12152) is in association with one or more of an inhibitors (e.g., a small organic molecule or an antibody or antigen-binding fragment thereof) such as: an MTOR (mammalian target of rapamycin) inhibitor, a cytotoxic agent, a platinum agent a BRAF inhibitor, a CDK4/6 inhibitor an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, an anti-LAG3 antibody or antigen-binding fragment thereof of the present invention (e.g., ADI-12126 or ADI-12152) is in association with one or more of: anti-PD1 (e.g., pembrolizumab, nivolumab, CT-011), anti-PDL1, anti-CTLA4, anti-TIM3, anti-CS1, (e.g., elotuzumab), anti-KIR2DL1/2/3 (e.g., lirilumab), anti-CD27, anti-CD137 (e.g., urelumab), anti-GITR (e.g., TRX518), anti-PD-L1 (e.g., BMS-936559, MSB0010718C or MPDL3280A), anti-PD-L2, anti-ILT1, anti-ILT2, anti-CEACAM1, anti-ILT3, anti-ILT4, anti-ILT5, anti-ILT6, anti-ILT7, anti-ILT8, anti-CD40, anti-OX40, anti-CD137, anti-KIR2DL1, anti-KIR2DL2/3, anti-KIR2DL4, anti-KIR2DL5A, anti-KIR2DL5B, anti-KIR3DL1, anti-KIR3DL2, anti-KIR3DL3, anti-NKG2A, anti-NKG2C, anti-NKG2E, or any small organic molecule inhibitor of such targets; IL-10, anti-IL10, anti-TSLP (thymic stromal lymphopoietin) or PEGylated IL-10.

In an embodiment of the invention, the molecular weight of the polyethylene glycol (PEG) moiety, on a PEGylated IL-10 molecule, is about 12,000 daltons or about 20,000 daltons. In an embodiment of the invention, PEGylated IL-10 (e.g., PEGylated human IL-10) comprises one or more polyethylene glycol molecules covalently attached via a linker (e.g., $C_{2-12}$ alkyl such as —$CH_2CH_2CH_2$—) to a single amino acid residue of a single subunit of IL-10, wherein said amino acid residue is the alpha amino group of the N-terminal amino acid residue or the epsilon amino group of a lysine residue. In an embodiment of the invention PEGylated IL-10 is: (PEG) b-L-NH-IL-10; wherein b is 1-9 and L is a $C_{2-12}$ alkyl linker moiety covalently attached to a nitrogen (N) of the single amino acid residue of the IL-10. In an embodiment of the invention, the IL-10 of PEGylated IL-10 has the formula: $[X—O(CH_2CH_2O)_n]_b$-L-NH-IL-10, wherein X is H or $C_{1-4}$ alkyl; n is 20 to 2300; b is 1 to 9; and L is a $C_{1-11}$ alkyl linker moiety which is covalently attached to the nitrogen (N) of the alpha amino group at the amino terminus of one IL-10 subunit; provided that when b is greater than 1, the total of n does not exceed 2300. See U.S. Pat. No. 7,052,686.

In an embodiment of the invention, the anti-IL-10 antibody or antigen-binding fragment thereof (e.g., human antibody) comprises the CDRs set forth below:

```
CDR-L1:
                                        (SEQ ID NO: 25)
KTSQNIFENLA;

CDR-L2:
                                        (SEQ ID NO: 26)
NASPLQA;

CDR-L3:
                                        (SEQ ID NO: 27)
HQYYSGYT;

CDR-H1:
                                        (SEQ ID NO: 28)
GFTFSDYHMA;

CDR-H2:
                                        (SEQ ID NO: 29)
SITLDATYTYYRDSVRG;

CDR-H3:
                                        (SEQ ID NO: 30)
HRGFSVWLDY (See U.S. Pat. No. 7,662,379)
```

In an embodiment of the invention, the anti-TSLP antibody or antigen-binding fragment thereof (e.g., human antibody) comprises the CDRs set forth below:

```
CDR-H1:
                                        (SEQ ID NO: 31)
GYIFTDYAMH;

CDR-H2:
                                        (SEQ ID NO: 32)
TFIPLLDTSDYNQNFK;

CDR-H3:
                                        (SEQ ID NO: 33)
MGVTHSYVMDA;
```

```
CDR-L1:
                                        (SEQ ID NO: 34)
RASQPISISVH;

CDR-L2:
                                        (SEQ ID NO: 35)
FASQSIS;

CDR-L3:
                                        (SEQ ID NO: 36)
QQTFSLPYT;

(see WO2008/76321)
```

In an embodiment of the invention, the anti-CD27 antibody or antigen-binding fragment thereof (e.g., human antibody) comprises the CDRs set forth below:

```
CDR-H1:
                                        (SEQ ID NO: 37)
GFIIKATYMH;

CDR-H2:
                                        (SEQ ID NO: 38)
RIDPANGETKYDPKFQV;

CDR-H3:
                                        (SEQ ID NO: 39)
YAWYFDV;

CDR-L1:
                                        (SEQ ID NO: 40)
RASENIYSFLA;

CDR-L2:
                                        (SEQ ID NO: 41)
HAKTLAE;

CDR-L3:
                                        (SEQ ID NO: 42)
QHYYGSPLT;

(See WO2012/04367).
```

Thus, the present invention includes compositions comprising an anti-LAG3 antibody or antigen-binding fragment thereof of the present invention (e.g., ADI-12126 or ADI-12152) in association with pembrolizumab; as well as methods for treating or preventing cancer in a subject comprising administering an effective amount of the anti-LAG3 antibody or antigen-binding fragment thereof in association with pembrolizumab (e.g., pembrolizumab dosed at 200 mg once every three weeks) to the subject. Optionally, the subject is also administered in association with a another further therapeutic agent.

In an embodiment of the invention, an anti-LAG3 antibody or antigen-binding fragment thereof of the present invention (e.g., ADI-12126 or ADI-12152) is in association with a pembrolizumab antibody which comprises an immunoglobulin heavy chain (or CDR-H1, CDR-H2 and CDR-H3 thereof) comprising the amino acid sequence:

```
                                        (SEQ ID NO: 43)
QVQLVQSGVEVKKPGASVKVSCKASGYTFTNYYMYWVRQAPGQGLEWMGG

INPSNGGTNENEKEKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLEPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK;

and an immunoglobulin light chain (or CDR-L1,
CDR-L2 and CDR-L3 thereof) comprising the amino
acid sequence:
                                        (SEQ ID NO: 44)
EIVLTQSPATLSLSPGERATLSCRASKGVSTSGYSYLHWYQQKPGQAPRLL

TYLASYLESGVPARFSGSGSGTDFTLTISSLEPEDFAVYYCQHSRDLPLTE

GGGTKVEIKRTVAAPSVFIFPPSDEQLKSGTASVVCLLNNEYPREAKVQWK

VDNALQSGNSQESVTEQDSKDSTYSLSSTLTLSKADYEKHKVYACEVTHQG

LSSPVTKSFNRGEC.
```

In an embodiment of the invention, an anti-LAG3 antibody or antigen-binding fragment thereof of the present invention (e.g., ADI-12126 or ADI-12152) is in association with an antibody comprising an immunoglobulin heavy chain (or CDR-H1, CDR-H2 and CDR-H3 thereof) comprising the amino acid sequence:

```
                                        (SEQ ID NO: 45)
QVQLVESGGGVVQPGRSLRLDCKASGITESNSGMHWVRQAPGKGLEWVAV

IWYDGSKRYYADSVKGRETISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLEPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK;

and an immunoglobulin light chain (or CDR-L1,
CDR-L2 and CDR-L3 thereof) comprising the amino
acid sequence:
                                        (SEQ ID NO: 46)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNEYPREAKVQWKV

DNALQSGNSQESVTEQDSKDSTYSLSSTLTLSKADYEKHKVYACEVTHQG

LSSPVTKSFNRGEC.
```

In an embodiment of the invention, an anti-LAG3 antibody or antigen-binding fragment thereof of the present invention (e.g., ADI-12126 or ADI-12152) is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, aflibercept, ALT-110, altretamine, amifostine, aminoglutethimide, amrubicin, amsacrine, anagrelide, anastrozole, angiostatin, AP-23573, ARQ-197, arzoxifene, AS-252424, AS-605240, asparaginase, ATI3387, AT-9263, atrasentan, axitinib, AZD1152, *Bacillus* Calmette- Guerin (BCG) vaccine, batabulin, BC-210, besodutox, bevacizumab, BGJ398, bicalutamide, Bio111, BIO140, BKM120, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, CEA (recombinant vaccinia-carcinoembryonic antigen vaccine), cediranib, CG-1521, CG-781, chlamydocin, chlorambucil, chlorotoxin, cilengitide, cimitidine, cisplatin, cladribine, clodronate, cobimetnib, COL-3, CP-724714, cyclophosphamide, cyproterone, cyproteroneacetate, cytarabine, cytosinearabinoside, dabrafenib, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, DNE03, docetaxel, dovitinib, doxorubicin, droloxifene, edotecarin, yttrium-90 labeled-edotreotide, edotreotide, EKB-569, EMD121974, encorafenib, endostatin, enzalutamide, enzastaurin, epirubicin, epithilone B, ERA-923, erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, fulvestrant, galeterone, ganetespib, gefitinib, gemcitabine, gimatecan, glucopyranosyl lipid A, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, imiquimod, INC280, INCB24360, INO1001, interferon, interleukin-2, interleukin-12, ipilimumab, irinotecan, JNJ-16241199, ketoconazole, KRX-0402, lapatinib, lasofoxifene, LEE011, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, LY3009120, marimastat, mechlorethamine, medroxyprogesteroneacetate, megestrolacetate, MEK162, melphalan, mercaptopurine, mesna, methotrexate, mithramycin, mitomycin, mitotane, mitoxantrone, a suspension of heat killed *Mycobacterium obuense*, tozasertib, MLN8054, natitoclax, neovastat, Neratinib, neuradiab, nilotinib, nilutimide, nolatrexed, NVP-BEZ235, oblimersen, octreotide, ofatumumab, oregovomab, ornatuzumab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, poly-ICLC, porfimer, prednisone, procarbazine, progestins, PSK protein bound polysaccharide (derived from Basidiomycete *coriolus versicolor*), PLX8394, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, 6-thioguanine, thiotepa, ticilimumab, tipifarnib, tivozanib, TKI-258, TLK286, TNFα (tumor necrosis factor alpha), topotecan, toremifene citrate, trabectedin, trametinib, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vemurafenib, vinblastine, vincristine, vindesine, vinorelbine, vitaxin, vitespan, vorinostat, VX-745, wortmannin, Xr311, Z-100 hot water extract of *Bacillus* tuberculosis, zanolimumab, ZK186619, ZK-304709, ZM336372 or ZSTK474.

In an embodiment of the invention, an anti-LAG3 antibody or antigen-binding fragment thereof of the present invention (e.g., ADI-12126 or ADI-12152) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an anti-LAG3 antibody or antigen-binding fragment thereof of the present invention (e.g., ADI-12126 or ADI-12152) is in association with an agent which treats or prevents such a deficiency, such as, e.g., filgrastim, PEG-filgrastim, erythropoietin, epoetin alfa or darbepoetin alfa.

In an embodiment of the invention, an anti-LAG3 antibody or antigen-binding fragment thereof (e.g., antagonist human antibody) of the present invention (e.g., ADI-12126 or ADI-12152) is in association with a vaccine. In an embodiment of the invention, the vaccine is an anti-cancer vaccine, a peptide vaccine or a DNA vaccine. For example, in an embodiment of the invention, the vaccine is a tumor cell (e.g., an irradiated tumor cell) or a dendritic cell (e.g., a dendritic cell pulsed with a tumor peptide).

In an embodiment of the invention, an anti-LAG3 antibody or antigen-binding fragment thereof of the present invention (e.g., ADI-12126 or ADI-12152) is administered in association with a therapeutic procedure. A therapeutic procedure is one or more steps carried out by a physician or clinician in treating a subject which is intended to alleviate one or more symptoms (e.g., of cancer and/or infectious disease) in the treated subject, whether by inducing the regression or elimination of such symptoms or by inhibiting the progression of such symptom(s), e.g., cancer symptoms such as tumor growth or metastasis, by any clinically measurable degree.

In an embodiment of the invention, a therapeutic procedure is anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures.

In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with an anti-LAG3 antibody or antigen-binding fragment thereof of the present invention (e.g., ADI-12126 or ADI-12152) is surgical tumorectomy.

In an embodiment of the invention, an anti-LAG3 antibody or antigen-binding fragment thereof of the present invention (e.g., ADI-12126 or ADI-12152) is in association with an MTOR (mammalian target of rapamycin) inhibitor.

In an embodiment of the invention, an anti-LAG3 antibody or antigen-binding fragment thereof of the present invention (e.g., ADI-12126 or ADI-12152) is in association with a cytotoxic agent.

In an embodiment of the invention, an anti-LAG3 antibody or antigen-binding fragment thereof of the present invention (e.g., ADI-12126 or ADI-12152) is in association with a platinum agent.

In an embodiment of the invention, an anti-LAG3 antibody or antigen-binding fragment thereof of the present invention (e.g., ADI-12126 or ADI-12152) is in association with an EGFR inhibitor.

In an embodiment of the invention, an anti-LAG3 antibody or antigen-binding fragment thereof of the present invention (e.g., ADI-12126 or ADI-12152) is in association with a VEGF inhibitor.

In an embodiment of the invention, an anti-LAG3 antibody or antigen-binding fragment thereof of the present invention (e.g., ADI-12126 or ADI-12152) is in association with a microtubule stabilizer.

In an embodiment of the invention, an anti-LAG3 antibody or antigen-binding fragment thereof of the present invention (e.g., ADI-12126 or ADI-12152) is in association with a taxane a CD20 inhibitor.

In an embodiment of the invention, an anti-LAG3 antibody or antigen-binding fragment thereof of the present invention (e.g., ADI-12126 or ADI-12152) is in association with a CD52 inhibitor.

In an embodiment of the invention, an anti-LAG3 antibody or antigen-binding fragment thereof of the present invention (e.g., ADI-12126 or ADI-12152) is in association with a CD30 inhibitor.

In an embodiment of the invention, an anti-LAG3 antibody or antigen-binding fragment thereof of the present invention (e.g., ADI-12126 or ADI-12152) is in association with a RANK (Receptor activator of nuclear factor kappa-B) inhibitor.

In an embodiment of the invention, an anti-LAG3 antibody or antigen-binding fragment thereof of the present invention (e.g., ADI-12126 or ADI-12152) is in association with a RANKL (Receptor activator of nuclear factor kappa-B ligand) inhibitor.

In an embodiment of the invention, an anti-LAG3 antibody or antigen-binding fragment thereof of the present invention (e.g., ADI-12126 or ADI-12152) is in association with a BRAF inhibitor, e.g., for treatment of melanoma.

In an embodiment of the invention, an anti-LAG3 antibody or antigen-binding fragment thereof of the present invention (e.g., ADI-12126 or ADI-12152) is in association with an a CDK4/6 inhibitor, e.g., for treatment of melanoma.

In an embodiment of the invention, an anti-LAG3 antibody or antigen-binding fragment thereof of the present invention (e.g., ADI-12126 or ADI-12152) is in association with an ERK inhibitor.

In an embodiment of the invention, an anti-LAG3 antibody or antigen-binding fragment thereof of the present invention (e.g., ADI-12126 or ADI-12152) is in association with a MAP Kinase inhibitor.

In an embodiment of the invention, an anti-LAG3 antibody or antigen-binding fragment thereof of the present invention (e.g., ADI-12126 or ADI-12152) is in association with an AKT inhibitor.

In an embodiment of the invention, an anti-LAG3 antibody or antigen-binding fragment thereof of the present invention (e.g., ADI-12126 or ADI-12152) is in association with a MEK inhibitor, e.g., for treatment of melanoma.

In an embodiment of the invention, an anti-LAG3 antibody or antigen-binding fragment thereof of the present invention (e.g., ADI-12126 or ADI-12152) is in association with a PI3K inhibitor.

In an embodiment of the invention, an anti-LAG3 antibody or antigen-binding fragment thereof of the present invention (e.g., ADI-12126 or ADI-12152) is in association with a HER1 inhibitor.

In an embodiment of the invention, an anti-LAG3 antibody or antigen-binding fragment thereof of the present invention (e.g., ADI-12126 or ADI-12152) is in association with a HER2 inhibitor.

In an embodiment of the invention, an anti-LAG3 antibody or antigen-binding fragment thereof of the present invention (e.g., ADI-12126 or ADI-12152) is in association with a HER3 inhibitor.

In an embodiment of the invention, an anti-LAG3 antibody or antigen-binding fragment thereof of the present invention (e.g., ADI-12126 or ADI-12152) is in association with a HER4 inhibitor.

In an embodiment of the invention, an anti-LAG3 antibody or antigen-binding fragment thereof of the present invention (e.g., ADI-12126 or ADI-12152) is in association with a Bcl2 inhibitor.

In an embodiment of the invention, an anti-LAG3 antibody or antigen-binding fragment thereof of the present invention (e.g., ADI-12126 or ADI-12152) is in association with a CD22 inhibitor.

In an embodiment of the invention, an anti-LAG3 antibody or antigen-binding fragment thereof of the present invention (e.g., ADI-12126 or ADI-12152) is in association with a CD79b inhibitor.

In an embodiment of the invention, an anti-LAG3 antibody or antigen-binding fragment thereof of the present invention (e.g., ADI-12126 or ADI-12152) is in association with an ErbB2 inhibitor.

In an embodiment of the invention, an anti-LAG3 antibody or antigen-binding fragment thereof of the present invention (e.g., ADI-12126 or ADI-12152) is in association with a farnesyl protein transferase inhibitor.

In an embodiment of the invention, an anti-LAG3 antibody or antigen-binding fragment thereof of the present invention (e.g., ADI-12126 or ADI-12152) is in association with anti-PD1.

In an embodiment of the invention, an anti-LAG3 antibody or antigen-binding fragment thereof of the present invention (e.g., ADI-12126 or ADI-12152) is in association with nivolumab.

In an embodiment of the invention, an anti-LAG3 antibody or antigen-binding fragment thereof of the present invention (e.g., ADI-12126 or ADI-12152) is in association with CT-011.

In an embodiment of the invention, an anti-LAG3 antibody or antigen-binding fragment thereof of the present invention (e.g., ADI-12126 or ADI-12152) is in association with anti-PDL1.

In an embodiment of the invention, an anti-LAG3 antibody or antigen-binding fragment thereof of the present invention (e.g., ADI-12126 or ADI-12152) is in association with anti-CTLA4.

In an embodiment of the invention, an anti-LAG3 antibody or antigen-binding fragment thereof of the present invention (e.g., ADI-12126 or ADI-12152) is in association with anti-TIM3.

In an embodiment of the invention, an anti-LAG3 antibody or antigen-binding fragment thereof of the present invention (e.g., ADI-12126 or ADI-12152) is in association with anti-CS1.

In an embodiment of the invention, an anti-LAG3 antibody or antigen-binding fragment thereof of the present invention (e.g., ADI-12126 or ADI-12152) is in association with elotuzumab.

In an embodiment of the invention, an anti-LAG3 antibody or antigen-binding fragment thereof of the present invention (e.g., ADI-12126 or ADI-12152) is in association with anti-KIR2DL1/2/3.

In an embodiment of the invention, an anti-LAG3 antibody or antigen-binding fragment thereof of the present invention (e.g., ADI-12126 or ADI-12152) is in association with lirilumab.

In an embodiment of the invention, an anti-LAG3 antibody or antigen-binding fragment thereof of the present invention (e.g., ADI-12126 or ADI-12152) is in association with an anti-CD137 antibody or antigen-binding fragment thereof, e.g., an agonist anti-CD137 antibody or fragment.

In an embodiment of the invention, an anti-LAG3 antibody or antigen-binding fragment thereof of the present invention (e.g., ADI-12126 or ADI-12152) is in association with urelumab.

In an embodiment of the invention, an anti-LAG3 antibody or antigen-binding fragment thereof of the present invention (e.g., ADI-12126 or ADI-12152) is in association with anti-GITR.

In an embodiment of the invention, an anti-LAG3 antibody or antigen-binding fragment thereof of the present invention (e.g., ADI-12126 or ADI-12152) is in association with TRX518.

In an embodiment of the invention, an anti-LAG3 antibody or antigen-binding fragment of the present invention (e.g., ADI-12126 or ADI-12152) is in association with anti-PD-L1.

In an embodiment of the invention, an anti-LAG3 antibody or antigen-binding fragment thereof of the present invention (e.g., ADI-12126 or ADI-12152) is in association with BMS-936559.

In an embodiment of the invention, an anti-LAG3 antibody or antigen-binding fragment thereof of the present invention (e.g., ADI-12126 or ADI-12152) is in association with MSB0010718C.

In an embodiment of the invention, an anti-LAG3 antibody or antigen-binding fragment thereof of the present invention (e.g., ADI-12126 or ADI-12152) is in association with MPDL3280A.

In an embodiment of the invention, an anti-LAG3 antibody or antigen-binding fragment thereof of the present invention (e.g., ADI-12126 or ADI-12152) is in association with anti-PD-L2.

In an embodiment of the invention, an anti-LAG3 antibody or antigen-binding fragment thereof of the present invention (e.g., ADI-12126 or ADI-12152) is in association with anti-ILT1.

In an embodiment of the invention, an anti-LAG3 antibody or antigen-binding fragment thereof of the present invention (e.g., ADI-12126 or ADI-12152) is in association with anti-ILT2.

In an embodiment of the invention, an anti-LAG3 antibody or antigen-binding fragment thereof of the present invention (e.g., ADI-12126 or ADI-12152) is in association with anti-CEACAM1.

In an embodiment of the invention, an anti-LAG3 antibody or antigen-binding fragment thereof of the present invention (e.g., ADI-12126 or ADI-12152) is in association with anti-ILT3.

In an embodiment of the invention, an anti-LAG3 antibody or antigen-binding fragment thereof of the present invention (e.g., ADI-12126 or ADI-12152) is in association with anti-ILT4.

In an embodiment of the invention, an anti-LAG3 antibody or antigen-binding fragment thereof of the present invention (e.g., ADI-12126 or ADI-12152) is in association with anti-ILT5.

In an embodiment of the invention, an anti-LAG3 antibody or antigen-binding fragment thereof of the present invention (e.g., ADI-12126 or ADI-12152) is in association with anti-ILT6.

In an embodiment of the invention, an anti-LAG3 antibody or antigen-binding fragment thereof of the present invention (e.g., ADI-12126 or ADI-12152) is in association with anti-ILT7.

In an embodiment of the invention, an anti-LAG3 antibody or antigen-binding fragment thereof of the present invention (e.g., ADI-12126 or ADI-12152) is in association with anti-ILT8.

In an embodiment of the invention, an anti-LAG3 antibody or antigen-binding fragment thereof of the present invention (e.g., ADI-12126 or ADI-12152) is in association with anti-CD40.

In an embodiment of the invention, an anti-LAG3 antibody or antigen-binding fragment thereof of the present invention (e.g., ADI-12126 or ADI-12152) is in association with anti-OX40.

In an embodiment of the invention, an anti-LAG3 antibody or antigen-binding fragment thereof of the present invention (e.g., ADI-12126 or ADI-12152) is in association with anti-CD137.

In an embodiment of the invention, an anti-LAG3 antibody or antigen-binding fragment thereof of the present invention (e.g., ADI-12126 or ADI-12152) is in association with anti-KIR2DL1.

In an embodiment of the invention, an anti-LAG3 antibody or antigen-binding fragment thereof of the present invention (e.g., ADI-12126 or ADI-12152) is in association with anti-KIR2DL2/3.

In an embodiment of the invention, an anti-LAG3 antibody or antigen-binding fragment thereof (e.g., antagonist human antibody) of the present invention (e.g., ADI-12126 or ADI-12152) is in association with anti-KIR2DL4.

In an embodiment of the invention, an anti-LAG3 antibody or antigen-binding fragment thereof (e.g., antagonist human antibody) of the present invention (e.g., ADI-12126 or ADI-12152) is in association with anti-KIR2DL5A.

In an embodiment of the invention, an anti-LAG3 antibody or antigen-binding fragment thereof (e.g., antagonist human antibody) of the present invention (e.g., ADI-12126 or ADI-12152) is in association with anti-KIR2DL5B.

In an embodiment of the invention, an anti-LAG3 antibody or antigen-binding fragment thereof (e.g., antagonist human antibody) of the present invention (e.g., ADI-12126 or ADI-12152) is in association with anti-KIR3DL1.

In an embodiment of the invention, an anti-LAG3 antibody or antigen-binding fragment thereof (e.g., antagonist human antibody) of the present invention (e.g., ADI-12126 or ADI-12152) is in association with anti-KIR3DL2.

In an embodiment of the invention, an anti-LAG3 antibody or antigen-binding fragment thereof (e.g., antagonist human antibody) of the present invention (e.g., ADI-12126 or ADI-12152) is in association with anti-KIR3DL3.

In an embodiment of the invention, an anti-LAG3 antibody or antigen-binding fragment thereof (e.g., antagonist human antibody) of the present invention (e.g., ADI-12126 or ADI-12152) is in association with anti-NKG2A.

In an embodiment of the invention, an anti-LAG3 antibody or antigen-binding fragment thereof (e.g., antagonist human antibody) of the present invention (e.g., ADI-12126 or ADI-12152) is in association with anti-NKG2C In an embodiment of the invention, an anti-LAG3 antibody or antigen-binding fragment thereof (e.g., antagonist human antibody) of the present invention (e.g., ADI-12126 or ADI-12152) is in association with anti-NKG2E.

In an embodiment of the invention, an anti-LAG3 antibody or antigen-binding fragment thereof (e.g., antagonist human antibody) of the present invention (e.g., ADI-12126 or ADI-12152) is in association with IL-10.

In an embodiment of the invention, an anti-LAG3 antibody or antigen-binding fragment thereof (e.g., antagonist human antibody) of the present invention (e.g., ADI-12126 or ADI-12152) is in association with anti-IL10.

In an embodiment of the invention, an anti-LAG3 antibody or antigen-binding fragment thereof (e.g., antagonist human antibody) of the present invention (e.g., ADI-12126 or ADI-12152) is in association with anti-TSLP (thymic stromal lymphopoietin).

In an embodiment of the invention, an anti-LAG3 antibody or antigen-binding fragment thereof (e.g., antagonist human antibody) of the present invention (e.g., ADI-12126 or ADI-12152) is in association with PEGylated IL-10. In an embodiment of the invention, PEGylated-IL-10 is administered to the subject at a dose of up to 20 micrograms/kg (e.g., 1, 2, 3, 4, 5, 6, 7, 8, 9, 10, 11, 12, 13, 14, 15, 16, 17, 18, 19 or 20 micrograms/kg). For example, up to 20 micrograms/kg daily, e.g., for up to four (e.g., 1, 2, 3 or 4) 28 day cycles—e.g., 20 micrograms/kg/day for four 28 day cycles.

In an embodiment of the invention, an anti-LAG3 antibody or antigen-binding fragment thereof (e.g., antagonist human antibody) of the present invention (e.g., ADI-12126 or ADI-12152) is in association with 13-cis-retinoic acid.

In an embodiment of the invention, an anti-LAG3 antibody or antigen-binding fragment thereof (e.g., antagonist human antibody) of the present invention (e.g., ADI-12126 or ADI-12152) is in association with 3-[5-(methylsulfonylpiperadinemethyl)-indolyl]-quinolone.

In an embodiment of the invention, an anti-LAG3 antibody or antigen-binding fragment thereof (e.g., antagonist human antibody) of the present invention (e.g., ADI-12126 or ADI-12152) is in association with 4-hydroxytamoxifen.

In an embodiment of the invention, an anti-LAG3 antibody or antigen-binding fragment thereof (e.g., antagonist human antibody) of the present invention (e.g., ADI-12126 or ADI-12152) is in association with 5-deooxyuridine.

In an embodiment of the invention, an anti-LAG3 antibody or antigen-binding fragment thereof (e.g., antagonist human antibody) of the present invention (e.g., ADI-12126 or ADI-12152) is in association with 5'-deoxy-5-fluorouridine.

In an embodiment of the invention, an anti-LAG3 antibody or antigen-binding fragment thereof (e.g., antagonist human antibody) of the present invention (e.g., ADI-12126 or ADI-12152) is in association with 5-fluorouracil.

In an embodiment of the invention, an anti-LAG3 antibody or antigen-binding fragment thereof (e.g., antagonist human antibody) of the present invention (e.g., ADI-12126 or ADI-12152) is in association with 6-mecaptopurine.

In an embodiment of the invention, an anti-LAG3 antibody or antigen-binding fragment thereof (e.g., antagonist human antibody) of the present invention (e.g., ADI-12126 or ADI-12152) is in association with 7-hydroxystaurosporine.

In an embodiment of the invention, an anti-LAG3 antibody or antigen-binding fragment thereof (e.g., antagonist human antibody) of the present invention (e.g., ADI-12126 or ADI-12152) is in association with A-443654.

In an embodiment of the invention, an anti-LAG3 antibody or antigen-binding fragment thereof (e.g., antagonist human antibody) of the present invention (e.g., ADI-12126 or ADI-12152) is in association with abirateroneacetate.

In an embodiment of the invention, an anti-LAG3 antibody or antigen-binding fragment thereof (e.g., antagonist human antibody) of the present invention (e.g., ADI-12126 or ADI-12152) is in association with abraxane.

In an embodiment of the invention, an anti-LAG3 antibody or antigen-binding fragment thereof (e.g., antagonist human antibody) of the present invention (e.g., ADI-12126 or ADI-12152) is in association with ABT-578.

In an embodiment of the invention, an anti-LAG3 antibody or antigen-binding fragment thereof (e.g., antagonist human antibody) of the present invention (e.g., ADI-12126 or ADI-12152) is in association with acolbifene.

In an embodiment of the invention, an anti-LAG3 antibody or antigen-binding fragment thereof (e.g., antagonist human antibody) of the present invention (e.g., ADI-12126 or ADI-12152) is in association with ADS-100380.

In an embodiment of the invention, an anti-LAG3 antibody or antigen-binding fragment thereof (e.g., antagonist human antibody) of the present invention (e.g., ADI-12126 or ADI-12152) is in association with ALT-110.

In an embodiment of the invention, an anti-LAG3 antibody or antigen-binding fragment thereof (e.g., antagonist human antibody) of the present invention (e.g., ADI-12126 or ADI-12152) is in association with altretamine.

In an embodiment of the invention, an anti-LAG3 antibody or antigen-binding fragment thereof (e.g., antagonist human antibody) of the present invention (e.g., ADI-12126 or ADI-12152) is in association with amifostine.

In an embodiment of the invention, an anti-LAG3 antibody or antigen-binding fragment thereof (e.g., antagonist human antibody) of the present invention (e.g., ADI-12126 or ADI-12152) is in association with aminoglutethimide.

In an embodiment of the invention, an anti-LAG3 antibody or antigen-binding fragment thereof (e.g., antagonist human antibody) of the present invention (e.g., ADI-12126 or ADI-12152) is in association with amrubicin.

In an embodiment of the invention, an anti-LAG3 antibody or antigen-binding fragment thereof (e.g., antagonist human antibody) of the present invention (e.g., ADI-12126 or ADI-12152) is in association with amsacrine.

In an embodiment of the invention, an anti-LAG3 antibody or antigen-binding fragment thereof (e.g., antagonist human antibody) of the present invention (e.g., ADI-12126 or ADI-12152) is in association with anagrelide.

In an embodiment of the invention, an anti-LAG3 antibody or antigen-binding fragment thereof (e.g., antagonist human antibody) of the present invention (e.g., ADI-12126 or ADI-12152) is in association with anastrozole.

In an embodiment of the invention, an anti-LAG3 antibody or antigen-binding fragment thereof (e.g., antagonist human antibody) of the present invention (e.g., ADI-12126 or ADI-12152) is in association with angiostatin.

In an embodiment of the invention, an anti-LAG3 antibody or antigen-binding fragment thereof (e.g., antagonist human antibody) of the present invention (e.g., ADI-12126 or ADI-12152) is in association with AP-23573.

In an embodiment of the invention, an anti-LAG3 antibody or antigen-binding fragment thereof (e.g., antagonist human antibody) of the present invention (e.g., ADI-12126 or ADI-12152) is in association with ARQ-197.

In an embodiment of the invention, an anti-LAG3 antibody or antigen-binding fragment thereof (e.g., antagonist human antibody) of the present invention (e.g., ADI-12126 or ADI-12152) is in association with arzoxifene.

In an embodiment of the invention, an anti-LAG3 antibody or antigen-binding fragment thereof (e.g., antagonist human antibody) of the present invention (e.g., ADI-12126 or ADI-12152) is in association with AS-252424.

In an embodiment of the invention, an anti-LAG3 antibody or antigen-binding fragment thereof (e.g., antagonist human antibody) of the present invention (e.g., ADI-12126 or ADI-12152) is in association with AS-605240.

In an embodiment of the invention, an anti-LAG3 antibody or antigen-binding fragment thereof (e.g., antagonist human antibody) of the present invention (e.g., ADI-12126 or ADI-12152) is in association with asparaginase.

In an embodiment of the invention, an anti-LAG3 antibody or antigen-binding fragment thereof (e.g., antagonist human antibody) of the present invention (e.g., ADI-12126 or ADI-12152) is in association with AT-9263.

In an embodiment of the invention, an anti-LAG3 antibody or antigen-binding fragment thereof (e.g., antagonist human antibody) of the present invention (e.g., ADI-12126 or ADI-12152) is in association with atrasentan.

In an embodiment of the invention, an anti-LAG3 antibody or antigen-binding fragment thereof (e.g., antagonist human antibody) of the present invention (e.g., ADI-12126 or ADI-12152) is in association with axitinib.

In an embodiment of the invention, an anti-LAG3 antibody or antigen-binding fragment thereof (e.g., antagonist human antibody) of the present invention (e.g., ADI-12126 or ADI-12152) is in association with AZD1152.

In an embodiment of the invention, an anti-LAG3 antibody or antigen-binding fragment thereof (e.g., antagonist human antibody) of the present invention (e.g., ADI-12126 or ADI-12152) is in association with *Bacillus* Calmette-Guerin (BCG) vaccine.

In an embodiment of the invention, an anti-LAG3 antibody or antigen-binding fragment thereof (e.g., antagonist human antibody) of the present invention (e.g., ADI-12126 or ADI-12152) is in association with batabulin.

In an embodiment of the invention, an anti-LAG3 antibody or antigen-binding fragment thereof (e.g., antagonist human antibody) of the present invention (e.g., ADI-12126 or ADI-12152) is in association with BC-210.

In an embodiment of the invention, an anti-LAG3 antibody or antigen-binding fragment thereof (e.g., antagonist human antibody) of the present invention (e.g., ADI-12126 or ADI-12152) is in association with besodutox.

In an embodiment of the invention, an anti-LAG3 antibody or antigen-binding fragment thereof (e.g., antagonist human antibody) of the present invention (e.g., ADI-12126 or ADI-12152) is in association with bevacizumab.

In an embodiment of the invention, an anti-LAG3 antibody or antigen-binding fragment thereof (e.g., antagonist human antibody) of the present invention (e.g., ADI-12126 or ADI-12152) is in association with bicalutamide.

In an embodiment of the invention, an anti-LAG3 antibody or antigen-binding fragment thereof (e.g., antagonist human antibody) of the present invention (e.g., ADI-12126 or ADI-12152) is in association with Bio111.

In an embodiment of the invention, an anti-LAG3 antibody or antigen-binding fragment thereof (e.g., antagonist human antibody) of the present invention (e.g., ADI-12126 or ADI-12152) is in association with BIO140.

In an embodiment of the invention, an anti-LAG3 antibody or antigen-binding fragment thereof (e.g., antagonist human antibody) of the present invention (e.g., ADI-12126 or ADI-12152) is in association with bleomycin.

In an embodiment of the invention, an anti-LAG3 antibody or antigen-binding fragment thereof (e.g., antagonist human antibody) of the present invention (e.g., ADI-12126 or ADI-12152) is in association with BMS-214662.

In an embodiment of the invention, an anti-LAG3 antibody or antigen-binding fragment thereof (e.g., antagonist human antibody) of the present invention (e.g., ADI-12126 or ADI-12152) is in association with BMS-247550.

In an embodiment of the invention, an anti-LAG3 antibody or antigen-binding fragment thereof (e.g., antagonist human antibody) of the present invention (e.g., ADI-12126 or ADI-12152) is in association with BMS-275291.

In an embodiment of the invention, an anti-LAG3 antibody or antigen-binding fragment thereof (e.g., antagonist human antibody) of the present invention (e.g., ADI-12126 or ADI-12152) is in association with BMS-310705.

In an embodiment of the invention, an anti-LAG3 antibody or antigen-binding fragment thereof (e.g., antagonist human antibody) of the present invention (e.g., ADI-12126 or ADI-12152) is in association with bortezimib.

In an embodiment of the invention, an anti-LAG3 antibody or antigen-binding fragment thereof (e.g., antagonist human antibody) of the present invention (e.g., ADI-12126 or ADI-12152) is in association with buserelin.

In an embodiment of the invention, an anti-LAG3 antibody or antigen-binding fragment thereof (e.g., antagonist human antibody) of the present invention (e.g., ADI-12126 or ADI-12152) is in association with busulfan.

In an embodiment of the invention, an anti-LAG3 antibody or antigen-binding fragment thereof (e.g., antagonist human antibody) of the present invention (e.g., ADI-12126 or ADI-12152) is in association with calcitriol.

In an embodiment of the invention, an anti-LAG3 antibody or antigen-binding fragment thereof (e.g., antagonist human antibody) of the present invention (e.g., ADI-12126 or ADI-12152) is in association with camptothecin.

In an embodiment of the invention, an anti-LAG3 antibody or antigen-binding fragment thereof (e.g., antagonist human antibody) of the present invention (e.g., ADI-12126 or ADI-12152) is in association with canertinib.

In an embodiment of the invention, an anti-LAG3 antibody or antigen-binding fragment thereof (e.g., antagonist human antibody) of the present invention (e.g., ADI-12126 or ADI-12152) is in association with capecitabine.

In an embodiment of the invention, an anti-LAG3 antibody or antigen-binding fragment thereof (e.g., antagonist human antibody) of the present invention (e.g., ADI-12126 or ADI-12152) is in association with carboplatin.

In an embodiment of the invention, an anti-LAG3 antibody or antigen-binding fragment thereof (e.g., antagonist human antibody) of the present invention (e.g., ADI-12126 or ADI-12152) is in association with carmustine.

In an embodiment of the invention, an anti-LAG3 antibody or antigen-binding fragment thereof (e.g., antagonist human antibody) of the present invention (e.g., ADI-12126 or ADI-12152) is in association with CC8490.

In an embodiment of the invention, an anti-LAG3 antibody or antigen-binding fragment thereof (e.g., antagonist human antibody) of the present invention (e.g., ADI-12126 or ADI-12152) is in association with CEA (recombinant vaccinia-carcinoembryonic antigen vaccine).

In an embodiment of the invention, an anti-LAG3 antibody or antigen-binding fragment thereof (e.g., antagonist human antibody) of the present invention (e.g., ADI-12126 or ADI-12152) is in association with cediranib.

In an embodiment of the invention, an anti-LAG3 antibody or antigen-binding fragment thereof (e.g., antagonist human antibody) of the present invention (e.g., ADI-12126 or ADI-12152) is in association with CG-1521.

In an embodiment of the invention, an anti-LAG3 antibody or antigen-binding fragment thereof (e.g., antagonist human antibody) of the present invention (e.g., ADI-12126 or ADI-12152) is in association with CG-781.

In an embodiment of the invention, an anti-LAG3 antibody or antigen-binding fragment thereof (e.g., antagonist human antibody) of the present invention (e.g., ADI-12126 or ADI-12152) is in association with chlamydocin.

In an embodiment of the invention, an anti-LAG3 antibody or antigen-binding fragment thereof (e.g., antagonist human antibody) of the present invention (e.g., ADI-12126 or ADI-12152) is in association with chlorambucil.

In an embodiment of the invention, an anti-LAG3 antibody or antigen-binding fragment thereof (e.g., antagonist human antibody) of the present invention (e.g., ADI-12126 or ADI-12152) is in association with chlorotoxin.

In an embodiment of the invention, an anti-LAG3 antibody or antigen-binding fragment thereof (e.g., antagonist human antibody) of the present invention (e.g., ADI-12126 or ADI-12152) is in association with cilengitide.

In an embodiment of the invention, an anti-LAG3 antibody or antigen-binding fragment thereof (e.g., antagonist human antibody) of the present invention (e.g., ADI-12126 or ADI-12152) is in association with cimitidine.

In an embodiment of the invention, an anti-LAG3 antibody or antigen-binding fragment thereof (e.g., antagonist human antibody) of the present invention (e.g., ADI-12126 or ADI-12152) is in association with cisplatin.

In an embodiment of the invention, an anti-LAG3 antibody or antigen-binding fragment thereof (e.g., antagonist human antibody) of the present invention (e.g., ADI-12126 or ADI-12152) is in association with cladribine.

In an embodiment of the invention, an anti-LAG3 antibody or antigen-binding fragment thereof (e.g., antagonist human antibody) of the present invention (e.g., ADI-12126 or ADI-12152) is in association with clodronate.

In an embodiment of the invention, an anti-LAG3 antibody or antigen-binding fragment thereof (e.g., antagonist human antibody) of the present invention (e.g., ADI-12126 or ADI-12152) is in association with COL-3.

In an embodiment of the invention, an anti-LAG3 antibody or antigen-binding fragment thereof (e.g., antagonist human antibody) of the present invention (e.g., ADI-12126 or ADI-12152) is in association with CP-724714.

In an embodiment of the invention, an anti-LAG3 antibody or antigen-binding fragment thereof (e.g., antagonist human antibody) of the present invention (e.g., ADI-12126 or ADI-12152) is in association with cyclophosphamide.

In an embodiment of the invention, an anti-LAG3 antibody or antigen-binding fragment thereof (e.g., antagonist human antibody) of the present invention (e.g., ADI-12126 or ADI-12152) is in association with cyproterone.

In an embodiment of the invention, an anti-LAG3 antibody or antigen-binding fragment thereof (e.g., antagonist human antibody) of the present invention (e.g., ADI-12126 or ADI-12152) is in association with cyproteroneacetate.

In an embodiment of the invention, an anti-LAG3 antibody or antigen-binding fragment thereof (e.g., antagonist human antibody) of the present invention (e.g., ADI-12126 or ADI-12152) is in association with cytarabine.

In an embodiment of the invention, an anti-LAG3 antibody or antigen-binding fragment thereof (e.g., antagonist human antibody) of the present invention (e.g., ADI-12126 or ADI-12152) is in association with cytosinearabinoside.

In an embodiment of the invention, an anti-LAG3 antibody or antigen-binding fragment thereof (e.g., antagonist human antibody) of the present invention (e.g., ADI-12126 or ADI-12152) is in association with dacarbazine.

In an embodiment of the invention, an anti-LAG3 antibody or antigen-binding fragment thereof (e.g., antagonist human antibody) of the present invention (e.g., ADI-12126 or ADI-12152) is in association with dacinostat.

In an embodiment of the invention, an anti-LAG3 antibody or antigen-binding fragment thereof (e.g., antagonist human antibody) of the present invention (e.g., ADI-12126 or ADI-12152) is in association with dactinomycin.

In an embodiment of the invention, an anti-LAG3 antibody or antigen-binding fragment thereof (e.g., antagonist human antibody) of the present invention (e.g., ADI-12126 or ADI-12152) is in association with dalotuzumab.

In an embodiment of the invention, an anti-LAG3 antibody or antigen-binding fragment thereof (e.g., antagonist human antibody) of the present invention (e.g., ADI-12126 or ADI-12152) is in association with danusertib.

In an embodiment of the invention, an anti-LAG3 antibody or antigen-binding fragment thereof (e.g., antagonist human antibody) of the present invention (e.g., ADI-12126 or ADI-12152) is in association with dasatanib.

In an embodiment of the invention, an anti-LAG3 antibody or antigen-binding fragment thereof (e.g., antagonist human antibody) of the present invention (e.g., ADI-12126 or ADI-12152) is in association with daunorubicin.

In an embodiment of the invention, an anti-LAG3 antibody or antigen-binding fragment thereof (e.g., antagonist human antibody) of the present invention (e.g., ADI-12126 or ADI-12152) is in association with decatanib.

In an embodiment of the invention, an anti-LAG3 antibody or antigen-binding fragment thereof (e.g., antagonist human antibody) of the present invention (e.g., ADI-12126 or ADI-12152) is in association with deguelin.

In an embodiment of the invention, an anti-LAG3 antibody or antigen-binding fragment thereof (e.g., antagonist human antibody) of the present invention (e.g., ADI-12126 or ADI-12152) is in association with denileukin.

In an embodiment of the invention, an anti-LAG3 antibody or antigen-binding fragment thereof (e.g., antagonist human antibody) of the present invention (e.g., ADI-12126 or ADI-12152) is in association with deoxycoformycin.

In an embodiment of the invention, an anti-LAG3 antibody or antigen-binding fragment thereof (e.g., antagonist human antibody) of the present invention (e.g., ADI-12126 or ADI-12152) is in association with depsipeptide.

In an embodiment of the invention, an anti-LAG3 antibody or antigen-binding fragment thereof (e.g., antagonist human antibody) of the present invention (e.g., ADI-12126 or ADI-12152) is in association with diarylpropionitrile.

In an embodiment of the invention, an anti-LAG3 antibody or antigen-binding fragment thereof (e.g., antagonist human antibody) of the present invention (e.g., ADI-12126 or ADI-12152) is in association with diethylstilbestrol.

In an embodiment of the invention, an anti-LAG3 antibody or antigen-binding fragment thereof (e.g., antagonist human antibody) of the present invention (e.g., ADI-12126 or ADI-12152) is in association with diftitox.

In an embodiment of the invention, an anti-LAG3 antibody or antigen-binding fragment thereof (e.g., antagonist human antibody) of the present invention (e.g., ADI-12126 or ADI-12152) is in association with docetaxel.

In an embodiment of the invention, an anti-LAG3 antibody or antigen-binding fragment thereof (e.g., antagonist human antibody) of the present invention (e.g., ADI-12126 or ADI-12152) is in association with dovitinib.

In an embodiment of the invention, an anti-LAG3 antibody or antigen-binding fragment thereof (e.g., antagonist human antibody) of the present invention (e.g., ADI-12126 or ADI-12152) is in association with doxorubicin.

In an embodiment of the invention, an anti-LAG3 antibody or antigen-binding fragment thereof (e.g., antagonist human antibody) of the present invention (e.g., ADI-12126 or ADI-12152) is in association with droloxifene.

In an embodiment of the invention, an anti-LAG3 antibody or antigen-binding fragment thereof (e.g., antagonist human antibody) of the present invention (e.g., ADI-12126 or ADI-12152) is in association with edotecarin.

In an embodiment of the invention, an anti-LAG3 antibody or antigen-binding fragment thereof (e.g., antagonist human antibody) of the present invention (e.g., ADI-12126 or ADI-12152) is in association with yttrium-90 labeled-edotreotide.

In an embodiment of the invention, an anti-LAG3 antibody or antigen-binding fragment thereof (e.g., antagonist human antibody) of the present invention (e.g., ADI-12126 or ADI-12152) is in association with edotreotide.

In an embodiment of the invention, an anti-LAG3 antibody or antigen-binding fragment thereof (e.g., antagonist human antibody) of the present invention (e.g., ADI-12126 or ADI-12152) is in association with EKB-569.

In an embodiment of the invention, an anti-LAG3 antibody or antigen-binding fragment thereof (e.g., antagonist human antibody) of the present invention (e.g., ADI-12126 or ADI-12152) is in association with EMD121974.

In an embodiment of the invention, an anti-LAG3 antibody or antigen-binding fragment thereof (e.g., antagonist human antibody) of the present invention (e.g., ADI-12126 or ADI-12152) is in association with endostatin.

In an embodiment of the invention, an anti-LAG3 antibody or antigen-binding fragment thereof (e.g., antagonist human antibody) of the present invention (e.g., ADI-12126 or ADI-12152) is in association with enzalutamide.

In an embodiment of the invention, an anti-LAG3 antibody or antigen-binding fragment thereof (e.g., antagonist human antibody) of the present invention (e.g., ADI-12126 or ADI-12152) is in association with enzastaurin.

In an embodiment of the invention, an anti-LAG3 antibody or antigen-binding fragment thereof (e.g., antagonist human antibody) of the present invention (e.g., ADI-12126 or ADI-12152) is in association with epirubicin.

In an embodiment of the invention, an anti-LAG3 antibody or antigen-binding fragment thereof (e.g., antagonist human antibody) of the present invention (e.g., ADI-12126 or ADI-12152) is in association with epithilone B.

In an embodiment of the invention, an anti-LAG3 antibody or antigen-binding fragment thereof (e.g., antagonist human antibody) of the present invention (e.g., ADI-12126 or ADI-12152) is in association with ERA-923.

In an embodiment of the invention, an anti-LAG3 antibody or antigen-binding fragment thereof (e.g., antagonist human antibody) of the present invention (e.g., ADI-12126 or ADI-12152) is in association with cetuximab.

In an embodiment of the invention, an anti-LAG3 antibody or antigen-binding fragment thereof (e.g., antagonist human antibody) of the present invention (e.g., ADI-12126 or ADI-12152) is in association with erlotinib.

In an embodiment of the invention, an anti-LAG3 antibody or antigen-binding fragment thereof (e.g., antagonist human antibody) of the present invention (e.g., ADI-12126 or ADI-12152) is in association with estradiol.

In an embodiment of the invention, an anti-LAG3 antibody or antigen-binding fragment thereof (e.g., antagonist human antibody) of the present invention (e.g., ADI-12126 or ADI-12152) is in association with estramustine.

In an embodiment of the invention, an anti-LAG3 antibody or antigen-binding fragment thereof (e.g., antagonist human antibody) of the present invention (e.g., ADI-12126 or ADI-12152) is in association with etoposide.

In an embodiment of the invention, an anti-LAG3 antibody or antigen-binding fragment thereof (e.g., antagonist human antibody) of the present invention (e.g., ADI-12126 or ADI-12152) is in association with everolimus.

In an embodiment of the invention, an anti-LAG3 antibody or antigen-binding fragment thereof (e.g., antagonist human antibody) of the present invention (e.g., ADI-12126 or ADI-12152) is in association with exemestane.

In an embodiment of the invention, an anti-LAG3 antibody or antigen-binding fragment thereof (e.g., antagonist human antibody) of the present invention (e.g., ADI-12126 or ADI-12152) is in association with ficlatuzumab.

In an embodiment of the invention, an anti-LAG3 antibody or antigen-binding fragment thereof (e.g., antagonist human antibody) of the present invention (e.g., ADI-12126 or ADI-12152) is in association with finasteride.

In an embodiment of the invention, an anti-LAG3 antibody or antigen-binding fragment thereof (e.g., antagonist human antibody) of the present invention (e.g., ADI-12126 or ADI-12152) is in association with flavopiridol.

In an embodiment of the invention, an anti-LAG3 antibody or antigen-binding fragment thereof (e.g., antagonist human antibody) of the present invention (e.g., ADI-12126 or ADI-12152) is in association with floxuridine.

In an embodiment of the invention, an anti-LAG3 antibody or antigen-binding fragment thereof (e.g., antagonist human antibody) of the present invention (e.g., ADI-12126 or ADI-12152) is in association with fludarabine.

In an embodiment of the invention, an anti-LAG3 antibody or antigen-binding fragment thereof (e.g., antagonist human antibody) of the present invention (e.g., ADI-12126 or ADI-12152) is in association with fludrocortisone.

In an embodiment of the invention, an anti-LAG3 antibody or antigen-binding fragment thereof (e.g., antagonist human antibody) of the present invention (e.g., ADI-12126 or ADI-12152) is in association with fluoxymesterone.

In an embodiment of the invention, an anti-LAG3 antibody or antigen-binding fragment thereof (e.g., antagonist human antibody) of the present invention (e.g., ADI-12126 or ADI-12152) is in association with flutamide.

In an embodiment of the invention, an anti-LAG3 antibody or antigen-binding fragment thereof (e.g., antagonist human antibody) of the present invention (e.g., ADI-12126 or ADI-12152) is in association with FOLFOX regimen.

In an embodiment of the invention, an anti-LAG3 antibody or antigen-binding fragment thereof (e.g., antagonist human antibody) of the present invention (e.g., ADI-12126 or ADI-12152) is in association with fulvestrant.

In an embodiment of the invention, an anti-LAG3 antibody or antigen-binding fragment thereof (e.g., antagonist human antibody) of the present invention (e.g., ADI-12126 or ADI-12152) is in association with galeterone.

In an embodiment of the invention, an anti-LAG3 antibody or antigen-binding fragment thereof (e.g., antagonist human antibody) of the present invention (e.g., ADI-12126 or ADI-12152) is in association with gefitinib.

In an embodiment of the invention, an anti-LAG3 antibody or antigen-binding fragment thereof (e.g., antagonist human antibody) of the present invention (e.g., ADI-12126 or ADI-12152) is in association with gemcitabine.

In an embodiment of the invention, an anti-LAG3 antibody or antigen-binding fragment thereof (e.g., antagonist human antibody) of the present invention (e.g., ADI-12126 or ADI-12152) is in association with gimatecan.

In an embodiment of the invention, an anti-LAG3 antibody or antigen-binding fragment thereof (e.g., antagonist human antibody) of the present invention (e.g., ADI-12126 or ADI-12152) is in association with glycopyranosyl lipid A.

In an embodiment of the invention, an anti-LAG3 antibody or antigen-binding fragment thereof (e.g., antagonist human antibody) of the present invention (e.g., ADI-12126 or ADI-12152) is in association with goserelin.

In an embodiment of the invention, an anti-LAG3 antibody or antigen-binding fragment thereof (e.g., antagonist human antibody) of the present invention (e.g., ADI-12126 or ADI-12152) is in association with goserelin acetate.

In an embodiment of the invention, an anti-LAG3 antibody or antigen-binding fragment thereof (e.g., antagonist human antibody) of the present invention (e.g., ADI-12126 or ADI-12152) is in association with gossypol.

In an embodiment of the invention, an anti-LAG3 antibody or antigen-binding fragment thereof (e.g., antagonist human antibody) of the present invention (e.g., ADI-12126 or ADI-12152) is in association with GSK461364.

In an embodiment of the invention, an anti-LAG3 antibody or antigen-binding fragment thereof (e.g., antagonist human antibody) of the present invention (e.g., ADI-12126 or ADI-12152) is in association with GSK690693.

In an embodiment of the invention, an anti-LAG3 antibody or antigen-binding fragment thereof (e.g., antagonist human antibody) of the present invention (e.g., ADI-12126 or ADI-12152) is in association with HMR-3339.

In an embodiment of the invention, an anti-LAG3 antibody or antigen-binding fragment thereof (e.g., antagonist human antibody) of the present invention (e.g., ADI-12126 or ADI-12152) is in association with hydroxyprogesteronecaproate.

In an embodiment of the invention, an anti-LAG3 antibody or antigen-binding fragment thereof (e.g., antagonist human antibody) of the present invention (e.g., ADI-12126 or ADI-12152) is in association with hydroxyurea.

In an embodiment of the invention, an anti-LAG3 antibody or antigen-binding fragment thereof (e.g., antagonist human antibody) of the present invention (e.g., ADI-12126 or ADI-12152) is in association with IC87114.

In an embodiment of the invention, an anti-LAG3 antibody or antigen-binding fragment thereof (e.g., antagonist human antibody) of the present invention (e.g., ADI-12126 or ADI-12152) is in association with idarubicin.

In an embodiment of the invention, an anti-LAG3 antibody or antigen-binding fragment thereof (e.g., antagonist human antibody) of the present invention (e.g., ADI-12126 or ADI-12152) is in association with idoxyfene.

In an embodiment of the invention, an anti-LAG3 antibody or antigen-binding fragment thereof (e.g., antagonist human antibody) of the present invention (e.g., ADI-12126 or ADI-12152) is in association with ifosfamide.

In an embodiment of the invention, an anti-LAG3 antibody or antigen-binding fragment thereof (e.g., antagonist human antibody) of the present invention (e.g., ADI-12126 or ADI-12152) is in association with IM862.

In an embodiment of the invention, an anti-LAG3 antibody or antigen-binding fragment thereof (e.g., antagonist human antibody) of the present invention (e.g., ADI-12126 or ADI-12152) is in association with imatinib.

In an embodiment of the invention, an anti-LAG3 antibody or antigen-binding fragment thereof (e.g., antagonist human antibody) of the present invention (e.g., ADI-12126 or ADI-12152) is in association with imiquimod.

In an embodiment of the invention, an anti-LAG3 antibody or antigen-binding fragment thereof (e.g., antagonist human antibody) of the present invention (e.g., ADI-12126 or ADI-12152) is in association with IMC-1C11.

In an embodiment of the invention, an anti-LAG3 antibody or antigen-binding fragment thereof (e.g., antagonist human antibody) of the present invention (e.g., ADI-12126 or ADI-12152) is in association with INCB24360.

In an embodiment of the invention, an anti-LAG3 antibody or antigen-binding fragment thereof (e.g., antagonist human antibody) of the present invention (e.g., ADI-12126 or ADI-12152) is in association with INO1001.

In an embodiment of the invention, an anti-LAG3 antibody or antigen-binding fragment thereof (e.g., antagonist human antibody) of the present invention (e.g., ADI-12126 or ADI-12152) is in association with interferon.

In an embodiment of the invention, an anti-LAG3 antibody or antigen-binding fragment thereof (e.g., antagonist human antibody) of the present invention (e.g., ADI-12126 or ADI-12152) is in association with interleukin-2 (IL-2).

In an embodiment of the invention, an anti-LAG3 antibody or antigen-binding fragment thereof (e.g., antagonist human antibody) of the present invention (e.g., ADI-12126 or ADI-12152) is in association with interleukin-12 (IL-12).

In an embodiment of the invention, an anti-LAG3 antibody or antigen-binding fragment thereof (e.g., antagonist human antibody) of the present invention (e.g., ADI-12126 or ADI-12152) is in association with ipilimumab.

In an embodiment of the invention, an anti-LAG3 antibody or antigen-binding fragment thereof (e.g., antagonist human antibody) of the present invention (e.g., ADI-12126 or ADI-12152) is in association with irinotecan.

In an embodiment of the invention, an anti-LAG3 antibody or antigen-binding fragment thereof (e.g., antagonist human antibody) of the present invention (e.g., ADI-12126 or ADI-12152) is in association with JNJ-16241199.

In an embodiment of the invention, an anti-LAG3 antibody or antigen-binding fragment thereof (e.g., antagonist human antibody) of the present invention (e.g., ADI-12126 or ADI-12152) is in association with ketoconazole.

In an embodiment of the invention, an anti-LAG3 antibody or antigen-binding fragment thereof (e.g., antagonist human antibody) of the present invention (e.g., ADI-12126 or ADI-12152) is in association with KRX-0402.

In an embodiment of the invention, an anti-LAG3 antibody or antigen-binding fragment thereof (e.g., antagonist human antibody) of the present invention (e.g., ADI-12126 or ADI-12152) is in association with lapatinib.

In an embodiment of the invention, an anti-LAG3 antibody or antigen-binding fragment thereof (e.g., antagonist human antibody) of the present invention (e.g., ADI-12126 or ADI-12152) is in association with lasofoxifene.

In an embodiment of the invention, an anti-LAG3 antibody or antigen-binding fragment thereof (e.g., antagonist human antibody) of the present invention (e.g., ADI-12126 or ADI-12152) is in association with letrozole.

In an embodiment of the invention, an anti-LAG3 antibody or antigen-binding fragment thereof (e.g., antagonist human antibody) of the present invention (e.g., ADI-12126 or ADI-12152) is in association with leucovorin.

In an embodiment of the invention, an anti-LAG3 antibody or antigen-binding fragment thereof of the present invention (e.g., ADI-12126 or ADI-12152) is in association with leuprolide.

In an embodiment of the invention, an anti-LAG3 antibody or antigen-binding fragment thereof (e.g., antagonist human antibody) of the present invention (e.g., ADI-12126 or ADI-12152) is in association with leuprolide acetate.

In an embodiment of the invention, an anti-LAG3 antibody or antigen-binding fragment thereof (e.g., antagonist human antibody) of the present invention (e.g., ADI-12126 or ADI-12152) is in association with levamisole.

In an embodiment of the invention, an anti-LAG3 antibody or antigen-binding fragment thereof (e.g., antagonist human antibody) of the present invention (e.g., ADI-12126 or ADI-12152) is in association with liposome entrapped paclitaxel.

In an embodiment of the invention, an anti-LAG3 antibody or antigen-binding fragment thereof (e.g., antagonist human antibody) of the present invention (e.g., ADI-12126 or ADI-12152) is in association with lomustine.

In an embodiment of the invention, an anti-LAG3 antibody or antigen-binding fragment thereof (e.g., antagonist human antibody) of the present invention (e.g., ADI-12126 or ADI-12152) is in association with lonafarnib.

In an embodiment of the invention, an anti-LAG3 antibody or antigen-binding fragment thereof (e.g., antagonist human antibody) of the present invention (e.g., ADI-12126 or ADI-12152) is in association with lucanthone.

In an embodiment of the invention, an anti-LAG3 antibody or antigen-binding fragment thereof (e.g., antagonist human antibody) of the present invention (e.g., ADI-12126 or ADI-12152) is in association with LY292223.

In an embodiment of the invention, an anti-LAG3 antibody or antigen-binding fragment thereof (e.g., antagonist human antibody) of the present invention (e.g., ADI-12126 or ADI-12152) is in association with LY292696.

In an embodiment of the invention, an anti-LAG3 antibody or antigen-binding fragment thereof (e.g., antagonist human antibody) of the present invention (e.g., ADI-12126 or ADI-12152) is in association with LY293646.

In an embodiment of the invention, an anti-LAG3 antibody or antigen-binding fragment thereof (e.g., antagonist human antibody) of the present invention (e.g., ADI-12126 or ADI-12152) is in association with LY293684.

In an embodiment of the invention, an anti-LAG3 antibody or antigen-binding fragment thereof (e.g., antagonist human antibody) of the present invention (e.g., ADI-12126 or ADI-12152) is in association with LY294002.

In an embodiment of the invention, an anti-LAG3 antibody or antigen-binding fragment thereof (e.g., antagonist human antibody) of the present invention (e.g., ADI-12126 or ADI-12152) is in association with LY317615.

In an embodiment of the invention, an anti-LAG3 antibody or antigen-binding fragment thereof (e.g., antagonist human antibody) of the present invention (e.g., ADI-12126 or ADI-12152) is in association with marimastat.

In an embodiment of the invention, an anti-LAG3 antibody or antigen-binding fragment thereof (e.g., antagonist human antibody) of the present invention (e.g., ADI-12126 or ADI-12152) is in association with mechlorethamine.

In an embodiment of the invention, an anti-LAG3 antibody or antigen-binding fragment thereof (e.g., antagonist human antibody) of the present invention (e.g., ADI-12126 or ADI-12152) is in association with medroxyprogesteroneacetate.

In an embodiment of the invention, an anti-LAG3 antibody or antigen-binding fragment thereof (e.g., antagonist human antibody) of the present invention (e.g., ADI-12126 or ADI-12152) is in association with megestrolacetate.

In an embodiment of the invention, an anti-LAG3 antibody or antigen-binding fragment thereof (e.g., antagonist human antibody) of the present invention (e.g., ADI-12126 or ADI-12152) is in association with melphalan.

In an embodiment of the invention, an anti-LAG3 antibody or antigen-binding fragment thereof (e.g., antagonist human antibody) of the present invention (e.g., ADI-12126 or ADI-12152) is in association with mercaptopurine.

In an embodiment of the invention, an anti-LAG3 antibody or antigen-binding fragment thereof (e.g., antagonist human antibody) of the present invention (e.g., ADI-12126 or ADI-12152) is in association with mesna.

In an embodiment of the invention, an anti-LAG3 antibody or antigen-binding fragment thereof (e.g., antagonist human antibody) of the present invention (e.g., ADI-12126 or ADI-12152) is in association with methotrexate.

In an embodiment of the invention, an anti-LAG3 antibody or antigen-binding fragment thereof (e.g., antagonist human antibody) of the present invention (e.g., ADI-12126 or ADI-12152) is in association with mithramycin.

In an embodiment of the invention, an anti-LAG3 antibody or antigen-binding fragment thereof (e.g., antagonist human antibody) of the present invention (e.g., ADI-12126 or ADI-12152) is in association with mitomycin.

In an embodiment of the invention, an anti-LAG3 antibody or antigen-binding fragment thereof (e.g., antagonist human antibody) of the present invention (e.g., ADI-12126 or ADI-12152) is in association with mitotane.

In an embodiment of the invention, an anti-LAG3 antibody or antigen-binding fragment thereof (e.g., antagonist human antibody) of the present invention (e.g., ADI-12126 or ADI-12152) is in association with mitoxantrone.

In an embodiment of the invention, an anti-LAG3 antibody or antigen-binding fragment thereof (e.g., antagonist human antibody) of the present invention (e.g., ADI-12126 or ADI-12152) is in association with tozasertib.

In an embodiment of the invention, an anti-LAG3 antibody or antigen-binding fragment thereof (e.g., antagonist human antibody) of the present invention (e.g., ADI-12126 or ADI-12152) is in association with a suspension of heat killed *Mycobacterium obuense*.

In an embodiment of the invention, an anti-LAG3 antibody or antigen-binding fragment thereof (e.g., antagonist human antibody) of the present invention (e.g., ADI-12126 or ADI-12152) is in association with MLN8054.

In an embodiment of the invention, an anti-LAG3 antibody or antigen-binding fragment thereof (e.g., antagonist human antibody) of the present invention (e.g., ADI-12126 or ADI-12152) is in association with neovastat.

In an embodiment of the invention, an anti-LAG3 antibody or antigen-binding fragment thereof (e.g., antagonist human antibody) of the present invention (e.g., ADI-12126 or ADI-12152) is in association with Neratinib.

In an embodiment of the invention, an anti-LAG3 antibody or antigen-binding fragment thereof (e.g., antagonist human antibody) of the present invention (e.g., ADI-12126 or ADI-12152) is in association with neuradiab.

In an embodiment of the invention, an anti-LAG3 antibody or antigen-binding fragment thereof (e.g., antagonist human antibody) of the present invention (e.g., ADI-12126 or ADI-12152) is in association with nilotinib.

In an embodiment of the invention, an anti-LAG3 antibody or antigen-binding fragment thereof (e.g., antagonist human antibody) of the present invention (e.g., ADI-12126 or ADI-12152) is in association with nilutimide.

In an embodiment of the invention, an anti-LAG3 antibody or antigen-binding fragment thereof (e.g., antagonist human antibody) of the present invention (e.g., ADI-12126 or ADI-12152) is in association with nolatrexe.

In an embodiment of the invention, an anti-LAG3 antibody or antigen-binding fragment thereof (e.g., antagonist human antibody) of the present invention (e.g., ADI-12126 or ADI-12152) is in association with NVP-BEZ235.

In an embodiment of the invention, an anti-LAG3 antibody or antigen-binding fragment thereof (e.g., antagonist human antibody) of the present invention (e.g., ADI-12126 or ADI-12152) is in association with oblimersen.

In an embodiment of the invention, an anti-LAG3 antibody or antigen-binding fragment thereof (e.g., antagonist human antibody) of the present invention (e.g., ADI-12126 or ADI-12152) is in association with octreotide.

In an embodiment of the invention, an anti-LAG3 antibody or antigen-binding fragment thereof (e.g., antagonist human antibody) of the present invention (e.g., ADI-12126 or ADI-12152) is in association with ofatumumab.

In an embodiment of the invention, an anti-LAG3 antibody or antigen-binding fragment thereof (e.g., antagonist human antibody) of the present invention (e.g., ADI-12126 or ADI-12152) is in association with oregovomab.

In an embodiment of the invention, an anti-LAG3 antibody or antigen-binding fragment thereof (e.g., antagonist human antibody) of the present invention (e.g., ADI-12126 or ADI-12152) is in association with orteronel.

In an embodiment of the invention, an anti-LAG3 antibody or antigen-binding fragment thereof (e.g., antagonist human antibody) of the present invention (e.g., ADI-12126 or ADI-12152) is in association with oxaliplatin.

In an embodiment of the invention, an anti-LAG3 antibody or antigen-binding fragment thereof (e.g., antagonist human antibody) of the present invention (e.g., ADI-12126 or ADI-12152) is in association with paclitaxel.

In an embodiment of the invention, an anti-LAG3 antibody or antigen-binding fragment thereof (e.g., antagonist human antibody) of the present invention (e.g., ADI-12126 or ADI-12152) is in association with palbociclib.

In an embodiment of the invention, an anti-LAG3 antibody or antigen-binding fragment thereof (e.g., antagonist human antibody) of the present invention (e.g., ADI-12126 or ADI-12152) is in association with pamidronate.

In an embodiment of the invention, an anti-LAG3 antibody or antigen-binding fragment thereof (e.g., antagonist human antibody) of the present invention (e.g., ADI-12126 or ADI-12152) is in association with panitumumab.

In an embodiment of the invention, an anti-LAG3 antibody or antigen-binding fragment thereof (e.g., antagonist human antibody) of the present invention (e.g., ADI-12126 or ADI-12152) is in association with pazopanib.

In an embodiment of the invention, an anti-LAG3 antibody or antigen-binding fragment thereof (e.g., antagonist human antibody) of the present invention (e.g., ADI-12126 or ADI-12152) is in association with PD0325901.

In an embodiment of the invention, an anti-LAG3 antibody or antigen-binding fragment thereof (e.g., antagonist human antibody) of the present invention (e.g., ADI-12126 or ADI-12152) is in association with PD184352.

In an embodiment of the invention, an anti-LAG3 antibody or antigen-binding fragment thereof (e.g., antagonist human antibody) of the present invention (e.g., ADI-12126 or ADI-12152) is in association with PEG-interferon.

In an embodiment of the invention, an anti-LAG3 antibody or antigen-binding fragment thereof (e.g., antagonist human antibody) of the present invention (e.g., ADI-12126 or ADI-12152) is in association with pemetrexed.

In an embodiment of the invention, an anti-LAG3 antibody or antigen-binding fragment thereof (e.g., antagonist human antibody) of the present invention (e.g., ADI-12126 or ADI-12152) is in association with pentostatin.

In an embodiment of the invention, an anti-LAG3 antibody or antigen-binding fragment thereof (e.g., antagonist human antibody) of the present invention (e.g., ADI-12126 or ADI-12152) is in association with perifosine.

In an embodiment of the invention, an anti-LAG3 antibody or antigen-binding fragment thereof (e.g., antagonist human antibody) of the present invention (e.g., ADI-12126 or ADI-12152) is in association with phenylalanine mustard.

In an embodiment of the invention, an anti-LAG3 antibody or antigen-binding fragment thereof (e.g., antagonist human antibody) of the present invention (e.g., ADI-12126 or ADI-12152) is in association with PI-103.

In an embodiment of the invention, an anti-LAG3 antibody or antigen-binding fragment thereof (e.g., antagonist human antibody) of the present invention (e.g., ADI-12126 or ADI-12152) is in association with pictilisib.

In an embodiment of the invention, an anti-LAG3 antibody or antigen-binding fragment thereof (e.g., antagonist human antibody) of the present invention (e.g., ADI-12126 or ADI-12152) is in association with PIK-75.

In an embodiment of the invention, an anti-LAG3 antibody or antigen-binding fragment thereof (e.g., antagonist human antibody) of the present invention (e.g., ADI-12126 or ADI-12152) is in association with pipendoxifene.

In an embodiment of the invention, an anti-LAG3 antibody or antigen-binding fragment thereof (e.g., antagonist human antibody) of the present invention (e.g., ADI-12126 or ADI-12152) is in association with PKI-166.

In an embodiment of the invention, an anti-LAG3 antibody or antigen-binding fragment thereof (e.g., antagonist human antibody) of the present invention (e.g., ADI-12126 or ADI-12152) is in association with plicamycin.

In an embodiment of the invention, an anti-LAG3 antibody or antigen-binding fragment thereof (e.g., antagonist human antibody) of the present invention (e.g., ADI-12126 or ADI-12152) is in association with poly-ICLC.

In an embodiment of the invention, an anti-LAG3 antibody or antigen-binding fragment thereof (e.g., antagonist human antibody) of the present invention (e.g., ADI-12126 or ADI-12152) is in association with porfimer.

In an embodiment of the invention, an anti-LAG3 antibody or antigen-binding fragment thereof (e.g., antagonist human antibody) of the present invention (e.g., ADI-12126 or ADI-12152) is in association with prednisone.

In an embodiment of the invention, an anti-LAG3 antibody or antigen-binding fragment thereof (e.g., antagonist human antibody) of the present invention (e.g., ADI-12126 or ADI-12152) is in association with procarbazine.

In an embodiment of the invention, an anti-LAG3 antibody or antigen-binding fragment thereof (e.g., antagonist human antibody) of the present invention (e.g., ADI-12126 or ADI-12152) is in association with progestins.

In an embodiment of the invention, an anti-LAG3 antibody or antigen-binding fragment thereof (e.g., antagonist human antibody) of the present invention (e.g., ADI-12126 or ADI-12152) is in association with PSK protein bound polysaccharide (derived from Basidiomycete *coriolus versicolor*).

In an embodiment of the invention, an anti-LAG3 antibody or antigen-binding fragment thereof (e.g., antagonist human antibody) of the present invention (e.g., ADI-12126 or ADI-12152) is in association with PX-866.

In an embodiment of the invention, an anti-LAG3 antibody or antigen-binding fragment thereof (e.g., antagonist human antibody) of the present invention (e.g., ADI-12126 or ADI-12152) is in association with R-763.

In an embodiment of the invention, an anti-LAG3 antibody or antigen-binding fragment thereof (e.g., antagonist human antibody) of the present invention (e.g., ADI-12126 or ADI-12152) is in association with raloxifene.

In an embodiment of the invention, an anti-LAG3 antibody or antigen-binding fragment thereof (e.g., antagonist human antibody) of the present invention (e.g., ADI-12126 or ADI-12152) is in association with raltitrexed.

In an embodiment of the invention, an anti-LAG3 antibody or antigen-binding fragment thereof (e.g., antagonist human antibody) of the present invention (e.g., ADI-12126 or ADI-12152) is in association with razoxin.

In an embodiment of the invention, an anti-LAG3 antibody or antigen-binding fragment thereof (e.g., antagonist human antibody) of the present invention (e.g., ADI-12126 or ADI-12152) is in association with ridaforolimus.

In an embodiment of the invention, an anti-LAG3 antibody or antigen-binding fragment thereof (e.g., antagonist human antibody) of the present invention (e.g., ADI-12126 or ADI-12152) is in association with rituximab.

In an embodiment of the invention, an anti-LAG3 antibody or antigen-binding fragment thereof (e.g., antagonist human antibody) of the present invention (e.g., ADI-12126 or ADI-12152) is in association with romidepsin.

In an embodiment of the invention, an anti-LAG3 antibody or antigen-binding fragment thereof (e.g., antagonist human antibody) of the present invention (e.g., ADI-12126 or ADI-12152) is in association with RTA744.

In an embodiment of the invention, an anti-LAG3 antibody or antigen-binding fragment thereof (e.g., antagonist human antibody) of the present invention (e.g., ADI-12126 or ADI-12152) is in association with rubitecan.

In an embodiment of the invention, an anti-LAG3 antibody or antigen-binding fragment thereof (e.g., antagonist human antibody) of the present invention (e.g., ADI-12126 or ADI-12152) is in association with scriptaid.

In an embodiment of the invention, an anti-LAG3 antibody or antigen-binding fragment thereof (e.g., antagonist human antibody) of the present invention (e.g., ADI-12126 or ADI-12152) is in association with Sdx102.

In an embodiment of the invention, an anti-LAG3 antibody or antigen-binding fragment thereof (e.g., antagonist human antibody) of the present invention (e.g., ADI-12126 or ADI-12152) is in association with seliciclib.

In an embodiment of the invention, an anti-LAG3 antibody or antigen-binding fragment thereof (e.g., antagonist human antibody) of the present invention (e.g., ADI-12126 or ADI-12152) is in association with selumetinib.

In an embodiment of the invention, an anti-LAG3 antibody or antigen-binding fragment thereof (e.g., antagonist human antibody) of the present invention (e.g., ADI-12126 or ADI-12152) is in association with semaxanib.

In an embodiment of the invention, an anti-LAG3 antibody or antigen-binding fragment thereof (e.g., antagonist human antibody) of the present invention (e.g., ADI-12126 or ADI-12152) is in association with SF1126.

In an embodiment of the invention, an anti-LAG3 antibody or antigen-binding fragment thereof (e.g., antagonist human antibody) of the present invention (e.g., ADI-12126 or ADI-12152) is in association with sirolimus.

In an embodiment of the invention, an anti-LAG3 antibody or antigen-binding fragment thereof (e.g., antagonist human antibody) of the present invention (e.g., ADI-12126 or ADI-12152) is in association with SN36093.

In an embodiment of the invention, an anti-LAG3 antibody or antigen-binding fragment thereof (e.g., antagonist human antibody) of the present invention (e.g., ADI-12126 or ADI-12152) is in association with sorafenib.

In an embodiment of the invention, an anti-LAG3 antibody or antigen-binding fragment thereof (e.g., antagonist human antibody) of the present invention (e.g., ADI-12126 or ADI-12152) is in association with spironolactone.

In an embodiment of the invention, an anti-LAG3 antibody or antigen-binding fragment thereof (e.g., antagonist human antibody) of the present invention (e.g., ADI-12126 or ADI-12152) is in association with squalamine.

In an embodiment of the invention, an anti-LAG3 antibody or antigen-binding fragment thereof (e.g., antagonist human antibody) of the present invention (e.g., ADI-12126 or ADI-12152) is in association with SR13668.

In an embodiment of the invention, an anti-LAG3 antibody or antigen-binding fragment thereof (e.g., antagonist human antibody) of the present invention (e.g., ADI-12126 or ADI-12152) is in association with streptozocin.

In an embodiment of the invention, an anti-LAG3 antibody or antigen-binding fragment thereof (e.g., antagonist human antibody) of the present invention (e.g., ADI-12126 or ADI-12152) is in association with SU6668.

In an embodiment of the invention, an anti-LAG3 antibody or antigen-binding fragment thereof (e.g., antagonist human antibody) of the present invention (e.g., ADI-12126 or ADI-12152) is in association with suberoylanalide hydroxamic acid.

In an embodiment of the invention, an anti-LAG3 antibody or antigen-binding fragment thereof (e.g., antagonist human antibody) of the present invention (e.g., ADI-12126 or ADI-12152) is in association with sunitinib.

In an embodiment of the invention, an anti-LAG3 antibody or antigen-binding fragment thereof (e.g., antagonist human antibody) of the present invention (e.g., ADI-12126 or ADI-12152) is in association with synthetic estrogen.

In an embodiment of the invention, an anti-LAG3 antibody or antigen-binding fragment thereof (e.g., antagonist human antibody) of the present invention (e.g., ADI-12126 or ADI-12152) is in association with talampanel.

In an embodiment of the invention, an anti-LAG3 antibody or antigen-binding fragment thereof (e.g., antagonist human antibody) of the present invention (e.g., ADI-12126 or ADI-12152) is in association with talimogene laherparepvec.

In an embodiment of the invention, an anti-LAG3 antibody or antigen-binding fragment thereof (e.g., antagonist human antibody) of the present invention (e.g., ADI-12126 or ADI-12152) is in association with tamoxifen.

In an embodiment of the invention, an anti-LAG3 antibody or antigen-binding fragment thereof (e.g., antagonist human antibody) of the present invention (e.g., ADI-12126 or ADI-12152) is in association with temozolomide.

In an embodiment of the invention, an anti-LAG3 antibody or antigen-binding fragment thereof (e.g., antagonist human antibody) of the present invention (e.g., ADI-12126 or ADI-12152) is in association with temsirolimus.

In an embodiment of the invention, an anti-LAG3 antibody or antigen-binding fragment thereof (e.g., antagonist human antibody) of the present invention (e.g., ADI-12126 or ADI-12152) is in association with teniposide.

In an embodiment of the invention, an anti-LAG3 antibody or antigen-binding fragment thereof (e.g., antagonist human antibody) of the present invention (e.g., ADI-12126 or ADI-12152) is in association with tesmilifene.

In an embodiment of the invention, an anti-LAG3 antibody or antigen-binding fragment thereof (e.g., antagonist human antibody) of the present invention (e.g., ADI-12126 or ADI-12152) is in association with testosterone.

In an embodiment of the invention, an anti-LAG3 antibody or antigen-binding fragment thereof (e.g., antagonist human antibody) of the present invention (e.g., ADI-12126 or ADI-12152) is in association with tetrandrine.

In an embodiment of the invention, an anti-LAG3 antibody or antigen-binding fragment thereof (e.g., antagonist human antibody) of the present invention (e.g., ADI-12126 or ADI-12152) is in association with TGX-221.

In an embodiment of the invention, an anti-LAG3 antibody or antigen-binding fragment thereof (e.g., antagonist human antibody) of the present invention (e.g., ADI-12126 or ADI-12152) is in association with thalidomide.

In an embodiment of the invention, an anti-LAG3 antibody or antigen-binding fragment thereof (e.g., antagonist human antibody) of the present invention (e.g., ADI-12126 or ADI-12152) is in association with 6-thioguanine.

In an embodiment of the invention, an anti-LAG3 antibody or antigen-binding fragment thereof (e.g., antagonist human antibody) of the present invention (e.g., ADI-12126 or ADI-12152) is in association with thiotepa.

In an embodiment of the invention, an anti-LAG3 antibody or antigen-binding fragment thereof (e.g., antagonist human antibody) of the present invention (e.g., ADI-12126 or ADI-12152) is in association with ticilimumab.

In an embodiment of the invention, an anti-LAG3 antibody or antigen-binding fragment thereof (e.g., antagonist human antibody) of the present invention (e.g., ADI-12126 or ADI-12152) is in association with tipifarnib.

In an embodiment of the invention, an anti-LAG3 antibody or antigen-binding fragment thereof (e.g., antagonist human antibody) of the present invention (e.g., ADI-12126 or ADI-12152) is in association with tivozanib.

In an embodiment of the invention, an anti-LAG3 antibody or antigen-binding fragment thereof (e.g., antagonist human antibody) of the present invention (e.g., ADI-12126 or ADI-12152) is in association with TKI-258.

In an embodiment of the invention, an anti-LAG3 antibody or antigen-binding fragment thereof (e.g., antagonist human antibody) of the present invention (e.g., ADI-12126 or ADI-12152) is in association with TLK286.

In an embodiment of the invention, an anti-LAG3 antibody or antigen-binding fragment thereof (e.g., antagonist human antibody) of the present invention (e.g., ADI-12126 or ADI-12152) is in association with topotecan.

In an embodiment of the invention, an anti-LAG3 antibody or antigen-binding fragment thereof (e.g., antagonist human antibody) of the present invention (e.g., ADI-12126 or ADI-12152) is in association with toremifene citrate.

In an embodiment of the invention, an anti-LAG3 antibody or antigen-binding fragment thereof (e.g., antagonist human antibody) of the present invention (e.g., ADI-12126 or ADI-12152) is in association with trabectedin.

In an embodiment of the invention, an anti-LAG3 antibody or antigen-binding fragment thereof (e.g., antagonist human antibody) of the present invention (e.g., ADI-12126 or ADI-12152) is in association with trastuzumab.

In an embodiment of the invention, an anti-LAG3 antibody or antigen-binding fragment thereof (e.g., antagonist human antibody) of the present invention (e.g., ADI-12126 or ADI-12152) is in association with tretinoin.

In an embodiment of the invention, an anti-LAG3 antibody or antigen-binding fragment thereof (e.g., antagonist human antibody) of the present invention (e.g., ADI-12126 or ADI-12152) is in association with trichostatin A.

In an embodiment of the invention, an anti-LAG3 antibody or antigen-binding fragment thereof (e.g., antagonist human antibody) of the present invention (e.g., ADI-12126 or ADI-12152) is in association with triciribinephosphate monohydrate.

In an embodiment of the invention, an anti-LAG3 antibody or antigen-binding fragment thereof (e.g., antagonist human antibody) of the present invention (e.g., ADI-12126 or ADI-12152) is in association with triptorelin pamoate.

In an embodiment of the invention, an anti-LAG3 antibody or antigen-binding fragment thereof (e.g., antagonist human antibody) of the present invention (e.g., ADI-12126 or ADI-12152) is in association with TSE-424.

In an embodiment of the invention, an anti-LAG3 antibody or antigen-binding fragment thereof (e.g., antagonist human antibody) of the present invention (e.g., ADI-12126 or ADI-12152) is in association with tumor necrosis factor alpha (TNFα).

In an embodiment of the invention, an anti-LAG3 antibody or antigen-binding fragment thereof (e.g., antagonist human antibody) of the present invention (e.g., ADI-12126 or ADI-12152) is in association with uracil mustard.

In an embodiment of the invention, an anti-LAG3 antibody or antigen-binding fragment thereof (e.g., antagonist human antibody) of the present invention (e.g., ADI-12126 or ADI-12152) is in association with valproic acid.

In an embodiment of the invention, an anti-LAG3 antibody or antigen-binding fragment thereof (e.g., antagonist human antibody) of the present invention (e.g., ADI-12126 or ADI-12152) is in association with valrubicin.

In an embodiment of the invention, an anti-LAG3 antibody or antigen-binding fragment thereof (e.g., antagonist human antibody) of the present invention (e.g., ADI-12126 or ADI-12152) is in association with vandetanib.

In an embodiment of the invention, an anti-LAG3 antibody or antigen-binding fragment thereof (e.g., antagonist human antibody) of the present invention (e.g., ADI-12126 or ADI-12152) is in association with vatalanib.

In an embodiment of the invention, an anti-LAG3 antibody or antigen-binding fragment thereof (e.g., antagonist human antibody) of the present invention (e.g., ADI-12126 or ADI-12152) is in association with VEGF trap.

In an embodiment of the invention, an anti-LAG3 antibody or antigen-binding fragment thereof (e.g., antagonist human antibody) of the present invention (e.g., ADI-12126 or ADI-12152) is in association with vinblastine.

In an embodiment of the invention, an anti-LAG3 antibody or antigen-binding fragment thereof (e.g., antagonist human antibody) of the present invention (e.g., ADI-12126 or ADI-12152) is in association with vincristine.

In an embodiment of the invention, an anti-LAG3 antibody or antigen-binding fragment thereof (e.g., antagonist human antibody) of the present invention (e.g., ADI-12126 or ADI-12152) is in association with vindesine.

In an embodiment of the invention, an anti-LAG3 antibody or antigen-binding fragment thereof (e.g., antagonist human antibody) of the present invention (e.g., ADI-12126 or ADI-12152) is in association with vinorelbine.

In an embodiment of the invention, an anti-LAG3 antibody or antigen-binding fragment thereof (e.g., antagonist human antibody) of the present invention (e.g., ADI-12126 or ADI-12152) is in association with vitaxin.

In an embodiment of the invention, an anti-LAG3 antibody or antigen-binding fragment thereof (e.g., antagonist human antibody) of the present invention (e.g., ADI-12126 or ADI-12152) is in association with vitespan.

In an embodiment of the invention, an anti-LAG3 antibody or antigen-binding fragment thereof (e.g., antagonist human antibody) of the present invention (e.g., ADI-12126 or ADI-12152) is in association with vorinostat.

In an embodiment of the invention, an anti-LAG3 antibody or antigen-binding fragment thereof (e.g., antagonist human antibody) of the present invention (e.g., ADI-12126 or ADI-12152) is in association with VX-745.

In an embodiment of the invention, an anti-LAG3 antibody or antigen-binding fragment thereof (e.g., antagonist human antibody) of the present invention (e.g., ADI-12126 or ADI-12152) is in association with wortmannin.

In an embodiment of the invention, an anti-LAG3 antibody or antigen-binding fragment thereof (e.g., antagonist human antibody) of the present invention (e.g., ADI-12126 or ADI-12152) is in association with Xr311.

In an embodiment of the invention, an anti-LAG3 antibody or antigen-binding fragment thereof (e.g., antagonist human antibody) of the present invention (e.g., ADI-12126 or ADI-12152) is in association with zanolimumab.

In an embodiment of the invention, an anti-LAG3 antibody or antigen-binding fragment thereof (e.g., antagonist human antibody) of the present invention (e.g., ADI-12126 or ADI-12152) is in association with Z-100 hot water extract of *Bacillus* tuberculosis.

In an embodiment of the invention, an anti-LAG3 antibody or antigen-binding fragment thereof (e.g., antagonist human antibody) of the present invention (e.g., ADI-12126 or ADI-12152) is in association with ZK186619.

In an embodiment of the invention, an anti-LAG3 antibody or antigen-binding fragment thereof (e.g., antagonist human antibody) of the present invention (e.g., ADI-12126 or ADI-12152) is in association with ZK-304709.

In an embodiment of the invention, an anti-LAG3 antibody or antigen-binding fragment thereof (e.g., antagonist human antibody) of the present invention (e.g., ADI-12126 or ADI-12152) is in association with ZM336372.

In an embodiment of the invention, an anti-LAG3 antibody or antigen-binding fragment thereof (e.g., antagonist human antibody) of the present invention (e.g., ADI-12126 or ADI-12152) is in association with ZSTK474.

In an embodiment of the invention, an anti-LAG3 antibody or antigen-binding fragment thereof (e.g., antagonist human antibody) of the present invention (e.g., ADI-12126 or ADI-12152) is in association with casopitant.

In an embodiment of the invention, an anti-LAG3 antibody or antigen-binding fragment thereof (e.g., antagonist human antibody) of the present invention (e.g., ADI-12126 or ADI-12152) is in association with netupitant.

In an embodiment of the invention, an anti-LAG3 antibody or antigen-binding fragment thereof (e.g., antagonist human antibody) of the present invention (e.g., ADI-12126 or ADI-12152) is in association with an NK-1 receptor antagonist.

In an embodiment of the invention, an anti-LAG3 antibody or antigen-binding fragment thereof (e.g., antagonist human antibody) of the present invention (e.g., ADI-12126 or ADI-12152) is in association with palonosetron.

In an embodiment of the invention, an anti-LAG3 antibody or antigen-binding fragment thereof (e.g., antagonist human antibody) of the present invention (e.g., ADI-12126 or ADI-12152) is in association with aprepitant.

In an embodiment of the invention, an anti-LAG3 antibody or antigen-binding fragment thereof (e.g., antagonist human antibody) of the present invention (e.g., ADI-12126 or ADI-12152) is in association with diphenhydramine.

In an embodiment of the invention, an anti-LAG3 antibody or antigen-binding fragment thereof (e.g., antagonist human antibody) of the present invention (e.g., ADI-12126 or ADI-12152) is in association with hydroxyzine.

In an embodiment of the invention, an anti-LAG3 antibody or antigen-binding fragment thereof (e.g., antagonist human antibody) of the present invention (e.g., ADI-12126 or ADI-12152) is in association with metoclopramide.

In an embodiment of the invention, an anti-LAG3 antibody or antigen-binding fragment thereof (e.g., antagonist human antibody) of the present invention (e.g., ADI-12126 or ADI-12152) is in association with lorazepam.

In an embodiment of the invention, an anti-LAG3 antibody or antigen-binding fragment thereof (e.g., antagonist human antibody) of the present invention (e.g., ADI-12126 or ADI-12152) is in association with alprazolam.

In an embodiment of the invention, an anti-LAG3 antibody or antigen-binding fragment thereof (e.g., antagonist human antibody) of the present invention (e.g., ADI-12126 or ADI-12152) is in association with haloperidol.

In an embodiment of the invention, an anti-LAG3 antibody or antigen-binding fragment thereof (e.g., antagonist human antibody) of the present invention (e.g., ADI-12126 or ADI-12152) is in association with droperidol.

In an embodiment of the invention, an anti-LAG3 antibody or antigen-binding fragment thereof (e.g., antagonist human antibody) of the present invention (e.g., ADI-12126 or ADI-12152) is in association with dronabinol.

In an embodiment of the invention, an anti-LAG3 antibody or antigen-binding fragment thereof (e.g., antagonist human antibody) of the present invention (e.g., ADI-12126 or ADI-12152) is in association with dexamethasone.

In an embodiment of the invention, an anti-LAG3 antibody or antigen-binding fragment thereof (e.g., antagonist human antibody) of the present invention (e.g., ADI-12126 or ADI-12152) is in association with methylprednisolone.

In an embodiment of the invention, an anti-LAG3 antibody or antigen-binding fragment thereof (e.g., antagonist human antibody) of the present invention (e.g., ADI-12126 or ADI-12152) is in association with prochlorperazine.

In an embodiment of the invention, an anti-LAG3 antibody or antigen-binding fragment thereof (e.g., antagonist human antibody) of the present invention (e.g., ADI-12126 or ADI-12152) is in association with granisetron.

In an embodiment of the invention, an anti-LAG3 antibody or antigen-binding fragment thereof (e.g., antagonist human antibody) of the present invention (e.g., ADI-12126 or ADI-12152) is in association with ondansetron.

In an embodiment of the invention, an anti-LAG3 antibody or antigen-binding fragment thereof (e.g., antagonist human antibody) of the present invention (e.g., ADI-12126 or ADI-12152) is in association with dolasetron.

In an embodiment of the invention, an anti-LAG3 antibody or antigen-binding fragment thereof (e.g., antagonist human antibody) of the present invention (e.g., ADI-12126 or ADI-12152) is in association with tropisetron.

In an embodiment of the invention, an anti-LAG3 antibody or antigen-binding fragment thereof (e.g., antagonist human antibody) of the present invention (e.g., ADI-12126 or ADI-12152) is in association with filgrastim.

In an embodiment of the invention, an anti-LAG3 antibody or antigen-binding fragment thereof (e.g., antagonist human antibody) of the present invention (e.g., ADI-12126 or ADI-12152) is in association with PEG-filgrastim.

In an embodiment of the invention, an anti-LAG3 antibody or antigen-binding fragment thereof (e.g., antagonist human antibody) of the present invention (e.g., ADI-12126 or ADI-12152) is in association with erythropoietin.

In an embodiment of the invention, an anti-LAG3 antibody or antigen-binding fragment thereof (e.g., antagonist human antibody) of the present invention (e.g., ADI-12126 or ADI-12152) is in association with epoetin alfa.

In an embodiment of the invention, an anti-LAG3 antibody or antigen-binding fragment thereof (e.g., antagonist human antibody) of the present invention (e.g., ADI-12126 or ADI-12152) is in association with darbepoetin alfa.

In an embodiment of the invention, an anti-LAG3 antibody or antigen-binding fragment thereof (e.g., antagonist human antibody) of the present invention (e.g., ADI-12126 or ADI-12152) is in association with dabrafenib.

In an embodiment of the invention, an anti-LAG3 antibody or antigen-binding fragment thereof (e.g., antagonist human antibody) of the present invention (e.g., ADI-12126 or ADI-12152) is in association with trametinib.

In an embodiment of the invention, an anti-LAG3 antibody or antigen-binding fragment thereof (e.g., antagonist human antibody) of the present invention (e.g., ADI-12126 or ADI-12152) is in association with vemurafenib.

In an embodiment of the invention, an anti-LAG3 antibody or antigen-binding fragment thereof (e.g., antagonist human antibody) of the present invention (e.g., ADI-12126 or ADI-12152) is in association with cobimetnib.

In an embodiment of the invention, an anti-LAG3 antibody or antigen-binding fragment thereof (e.g., antagonist human antibody) of the present invention (e.g., ADI-12126 or ADI-12152) is in association with LY3009120.

In an embodiment of the invention, an anti-LAG3 antibody or antigen-binding fragment thereof (e.g., antagonist human antibody) of the present invention (e.g., ADI-12126 or ADI-12152) is in association with DNE03.

In an embodiment of the invention, an anti-LAG3 antibody or antigen-binding fragment thereof (e.g., antagonist human antibody) of the present invention (e.g., ADI-12126 or ADI-12152) is in association with ATI13387.

In an embodiment of the invention, an anti-LAG3 antibody or antigen-binding fragment thereof (e.g., antagonist human antibody) of the present invention (e.g., ADI-12126 or ADI-12152) is in association with ganetespib.

In an embodiment of the invention, an anti-LAG3 antibody or antigen-binding fragment thereof (e.g., antagonist human antibody) of the present invention (e.g., ADI-12126 or ADI-12152) is in association with encorafenib.

In an embodiment of the invention, an anti-LAG3 antibody or antigen-binding fragment thereof (e.g., antagonist human antibody) of the present invention (e.g., ADI-12126 or ADI-12152) is in association with MEK162.

In an embodiment of the invention, an anti-LAG3 antibody or antigen-binding fragment thereof (e.g., antagonist human antibody) of the present invention (e.g., ADI-12126 or ADI-12152) is in association with BKM120.

In an embodiment of the invention, an anti-LAG3 antibody or antigen-binding fragment thereof (e.g., antagonist human antibody) of the present invention (e.g., ADI-12126 or ADI-12152) is in association with LEE011.

In an embodiment of the invention, an anti-LAG3 antibody or antigen-binding fragment thereof (e.g., antagonist human antibody) of the present invention (e.g., ADI-12126 or ADI-12152) is in association with BGJ398.

In an embodiment of the invention, an anti-LAG3 antibody or antigen-binding fragment thereof (e.g., antagonist human antibody) of the present invention (e.g., ADI-12126 or ADI-12152) is in association with INC280.

In an embodiment of the invention, an anti-LAG3 antibody or antigen-binding fragment thereof (e.g., antagonist human antibody) of the present invention (e.g., ADI-12126 or ADI-12152) is in association with PLX8394.

In an embodiment of the invention, an anti-LAG3 antibody or antigen-binding fragment thereof (e.g., antagonist human antibody) of the present invention (e.g., ADI-12126 or ADI-12152) is in association with ornatuzumab.

In an embodiment of the invention, an anti-LAG3 antibody or antigen-binding fragment thereof (e.g., antagonist human antibody) of the present invention (e.g., ADI-12126 or ADI-12152) is in association with natitoclax.

In an embodiment of the invention, an anti-LAG3 antibody or antigen-binding fragment thereof (e.g., antagonist human antibody) of the present invention (e.g., ADI-12126 or ADI-12152) is in association with aflibercept.

The term "in association with" indicates that the components, an anti-LAG3 antibody or antigen-binding fragment thereof of the present invention (e.g., ADI-12126 or ADI-12152) along with another agent such as pembrolizumab or nivolumab, can be formulated into a single composition, e.g., for simultaneous delivery, or formulated separately into two or more compositions (e.g., a kit). Each component can be administered to a subject at the same time as the other component or at a different time than when the other component is administered; for example, each administration may be given non-simultaneously (e.g., separately or sequentially) at intervals over a given period of time. Moreover, the separate components may be administered to a subject by the same or by a different route (e.g., wherein an anti-LAG3 antibody or antigen-binding fragment thereof (e.g., ADI-12126A is administered parenterally and paclitaxel is administered orally).

Assays and Experimental and Diagnostic Uses

The present invention includes any method for forming a complex between an anti-LAG3 antibody or antigen-binding fragment thereof of the present invention (e.g., ADI-12126 or ADI-12152) and LAG3 (e.g., human LAG3) comprising contacting the LAG3 polypeptide with the anti-LAG3 antibody or fragment under conditions suitable for binding and complex formation.

The anti-LAG3 antibodies and antigen-binding fragments thereof disclosed herein (e.g., ADI-12126 or ADI-12152) may be used as affinity purification agents. In this process, the anti-LAG3 antibodies and antigen-binding fragments thereof are immobilized on a solid phase such a sephadex, glass or agarose resin or filter paper, using methods well known in the art. The immobilized antibody or fragment is contacted with a sample containing the LAG3 protein (or a fragment thereof) to be purified, and, thereafter, the support is washed with a suitable solvent that will remove substantially all of the material in the sample except the LAG3 protein which is bound to the immobilized antibody or fragment. Finally, the support is washed with a solvent which elutes the bound LAG3 (e.g., protein A). Such immobilized antibodies and fragments as well as complexes thereof with LAG3 form part of the present invention.

The present invention provides methods for using the anti-LAG3 antibodies and antigen-binding fragments thereof of the present invention to determine the extent of T-cell activation that a particular subject is having or could have in the present of the antibody or fragment. For example, embodiments of the invention include methods including:
(i) contacting T-cells (e.g., CD4+ T-cells) from a subject with superantigen (e.g., any one or more of a staphylococcal superantigen such as SEA, SEB (*Staphylococcus* enterotoxin B), SEC2, SEC3, SED, SEH and/or TSST; and/or any one or more of a streptococcal superantigen such as SPE-A, SPE-C, SPE-H and/or SMEZ-2), e.g., at a concentration of 500 pg/ml or more, such as about 10 ng/ml or 100 ng/ml, in the presence of the anti-LAG3 antibody or fragment (optionally, the T-cells are pre-incubated with the superantigen (e.g., SEB) and antibody or fragment for about 48 or 72 hours) and
(ii) determining the level of production of cytokine (e.g., TNF-alpha, GM-CSF, IFN-gamma and/or IL-2) of said T-cells; wherein the level of production of said cytokine(s) indicates the level of T-cell activation in the present of the antibody or fragment.
Subjects possessing T-cells which exhibit higher cytokine production in the presence of superantigen and anti-LAG3 antibody or fragment than in the absence of the antibody or fragment are considered superior candidates for receipt of the antibody or fragment as a therapy, e.g., for treating cancer or infection. In an embodiment of the invention, such superior candidates are selected for receipt of the antibody or fragment. In an embodiment of the invention, such superior candidates are administered an effective amount of the antibody or fragment. In an embodiment of the invention, the method includes the step (before step (i) above) of isolating the T-cells from the blood of the subject. In an embodiment of the invention, the T-cells are contacted with anti-LAG3 antibody or antigen-binding fragment thereof of the present invention and pembrolizumab.

Further provided are antigens for generating secondary antibodies which are useful, for example, for performing Western blots and other immunoassays discussed herein. In particular, polypeptides are disclosed which comprise the variable regions and/or CDR sequences of an anti-LAG3 antibody or fragment disclosed herein (e.g., ADI-12126 or ADI-12152) and which may be used to generate anti-idiotypic antibodies for use in specifically detecting the presence of the antibody, e.g., in a therapeutic context.

The present invention includes cell-based ELISA methods using the anti-LAG3 antibodies and antigen-binding fragments thereof of the present invention (e.g., ADI-12126 or ADI-12152). In an embodiment of the invention, the method includes the steps: (i) contacting cells (e.g., cells or tissue taken from a tumor, e.g., which include lymphocytes suspected of expressing LAG3) that are immobilized to a solid surface (e.g., a microplate) which are to be tested for the presence of LAG3, with an anti-LAG3 antibody or antigen-binding fragment thereof of the present invention,
(ii) optionally washing the mixture to remove unbound anti-LAG3 antibody or fragment,
(iii) contacting the anti-LAG3 antibody or fragment with a labeled secondary antibody or antigen-binding fragment thereof that binds to the anti-LAG3 antibody or fragment,
(iv) optionally washing the complex to remove unbound antibodies or fragments; and
(v) detecting the presence of the label on the secondary antibody or fragment; wherein detection of the label indicates that the cells contain LAG3. For example, the present invention includes such cell-based ELISA methods for identifying LAG3+ cells in a tumor sample.

The present invention includes ELISA assays (enzyme-linked immunosorbent assay) incorporating the use of an immobilized anti-LAG3 antibody or antigen-binding fragment thereof disclosed herein (e.g., ADI-12126 or ADI-12152). For example, such a method comprises the following steps:
(a) coat a substrate (e.g., surface of a microtiter plate well, e.g., a plastic plate) with anti-LAG3 antibody or antigen-binding fragment thereof (e.g., ADI-12126 or ADI-12152);
(b) apply a sample to be tested for the presence of LAG3 to the substrate (e.g., cells taken from a tumor, e.g., which include lymphocytes suspected of expressing LAG3);
(c) wash the plate, so that unbound material in the sample is removed;
(d) apply detectably labeled antibodies (e.g., enzyme-linked antibodies) which are also specific to the LAG3 antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.
Detection of the label associated with the substrate indicates the presence of the LAG3 protein. The ELISA methods can also be used identifying LAG3+ cells in a tumor sample.

In a further embodiment, the labeled antibody or antigen-binding fragment thereof is labeled with peroxidase which reacts with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3$H) which can be detected by scintillation counter in the presence of a scintillant.

An anti-LAG3 antibody or antigen-binding fragment thereof of the invention (e.g., ADI-12126 or ADI-12152) may be used in a Western blot or immune-protein blot procedure. Such a procedure forms part of the present invention and includes e.g.:
(1) providing a membrane or other solid substrate comprising a sample to be tested for the presence of LAG3 (optionally the method includes the step of transferring proteins from a sample to be tested for the presence of LAG3 (e.g., from a PAGE or SDS-PAGE electrophoretic separation of the proteins in the sample) onto a membrane or other solid substrate using a method known in the art (e.g., semi-dry blotting or tank blotting)); and contacting the membrane or other solid substrate to be tested for the presence of bound LAG3 or a fragment thereof with an anti-LAG3 antibody or antigen-binding fragment thereof of the invention.

Such a membrane may take the form, for example, of a nitrocellulose or vinyl-based (e.g., polyvinylidene fluoride (PVDF)) membrane to which the proteins to be tested for the presence of LAG3 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-LAG3 antibody or fragment, the membrane is optionally blocked, e.g., with non-fat dry milk or the like so as to bind non-specific protein binding sites on the membrane.
(2) optionally, washing the membrane one or more times to remove unbound anti-LAG3 antibody or fragment and other unbound substances; and
(3) detecting the bound anti-LAG3 antibody or fragment.

Detection of the bound antibody or fragment indicates that the LAG3 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody label.

The anti-LAG3 antibodies and antigen-binding fragments thereof disclosed herein (e.g., ADI-12126 or ADI-12152) may also be used for immunohistochemistry. Such a method forms part of the present invention and comprises, e.g.,
(1) contacting cells or tissue (for example, comprising TILs and tumor cells (e.g., melanoma tumor)) to be tested for the presence of LAG3 protein with an anti-LAG3 antibody or antigen-binding fragment thereof of the invention; and
(2) detecting the antibody or fragment on or in the cells or tissue.

If the antibody or fragment itself is detectably labeled, it can be detected directly. Alternatively, the antibody or fragment may be bound by a detectably labeled secondary antibody wherein the label is then detected. Detection can be by visual inspection, e.g., under a microscope.

Anti-LAG3 antibodies and antigen-binding fragments thereof disclosed herein (e.g., ADI-12126 or ADI-12152) may also be used for in vivo tumor imaging. Such a method may include injection of a detectably labeled, e.g., radiolabeled, anti-LAG3 antibody or antigen-binding fragment thereof (as discussed herein) into the body of a patient to be tested for the presence of a tumor or other tissue or cell associated with LAG3 expression (e.g., which expresses LAG3, for example, on tumor infiltrating lymphocytes (TILs)) followed by imaging, e.g., nuclear imaging, of the body of the patient to detect the presence of the labeled antibody or fragment e.g., at loci comprising a high concentration of the antibody or fragment which are bound to or associated with the tumor. The detection of the loci indicates the presence of the LAG3 (e.g., the LAG3$^+$ TILs in a tumor).

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) *International Rev. Neurobiol.* 67:385-440).

The present invention provide a method for determining whether a tumor in a subject is sensitive to treatment with an anti-LAG3 antibody or antigen-binding fragment thereof of the present invention comprising determining whether the LAG3 is expressed in or on the tumor infiltrating lymphocytes (TILs) and, if said expression is identified, determining that the tumor is sensitive to said treatment. The TILs can be determined to express LAG3 using any of the methods set forth herein, e.g., ELISA or in vivo imaging. In an embodiment of the invention, the method comprises the step of obtaining a sample of said tumor tissue before making the determination of LAG3 expression is done. For example, in an embodiment of the invention, the sample is obtained surgically, e.g., by biopsy, for example, needle biopsy or partial tumorectomy. In an embodiment of the invention, LAG3 expression is determined by contacting the TILs with the antibody or fragment and detecting the presence of the antibody or fragment bound to the tumor tissue or fragment.

Pharmaceutical Compositions and Administration

To prepare pharmaceutical or sterile compositions of the anti-LAG3 antibodies and antigen-binding fragments thereof (e.g., ADI-12126 or ADI-12152), the antibody or antigen-binding fragment thereof can be admixed with a pharmaceutically acceptable carrier or excipient. See, e.g., *Remington's Pharmaceutical Sciences* and U.S. Pharmacopeia: National Formulary, Mack Publishing Company, Easton, Pa. (1984). Such compositions are part of the present invention.

The scope of the present invention includes dessicated, e.g., freeze-dried, compositions comprising an anti-LAG3 antibody or antigen-binding fragment thereof (e.g., ADI-12126 or ADI-12152) or a pharmaceutical composition thereof that includes a pharmaceutically acceptable carrier but substantially lacks water.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Toxicity and therapeutic efficacy of the antibody or fragment compositions, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose effective in 50% of the population). The dose ratio between toxic and therapeutic effects is the therapeutic index ($LD_{50}$/$ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-LAG3 antibody or antigen-binding fragment thereof disclosed herein (e.g., ADI-12126 or ADI-12152) is administered to the subject in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present invention provided methods for administering an anti-LAG3 antibody or antigen-binding fragment thereof (e.g., ADI-12126 or ADI-12152) comprising introducing the antibody or fragment into the body of a subject. For example, the method comprises piercing the body of the subject with a needle of a syringe and injecting the antibody or fragment into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the antibodies or antigen-binding fragments (e.g., ADI-12126 or ADI-12152), polypeptides or polynucleotides set forth herein or a pharmaceutical composition thereof comprising a pharmaceutically acceptable carrier.

The present invention also provides an injection device comprising any of the anti-LAG3 antibodies or antigen-binding fragments (e.g., ADI-12126 or ADI-12152), polypeptides or polynucleotides set forth herein or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an anti-LAG3 antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

Alternately, one may administer the anti-LAG3 antibody or antigen-binding fragment (e.g., ADI-12126 or ADI-12152) in a local rather than systemic manner, for example, via injection of the antibody or fragment directly into a tumor, e.g., a tumor having $LAG3^+$ TILs. Furthermore, one may administer the antibody or fragment in a targeted drug delivery system, for example, in a liposome coated with a tissue-specific antibody, targeting, for example, a tumor e.g., a $LAG3^+$ tumor, e.g., characterized by immunopathology. The liposomes will be targeted to and taken up selectively by the afflicted tissue. Such methods and liposomes are part of the present invention.

"Treat" or "treating" means to administer anti-LAG3 antibodies or antigen-binding fragments thereof of the present invention (e.g., ADI-12126 or ADI-12152), to a subject (e.g., a human) having one or more symptoms of a disease for which the anti-LAG3 antibodies and antigen-binding fragments are effective, e.g., in the treatment of a subject having cancer or an infectious disease, or being suspected of having cancer or infectious disease, for which the agent has therapeutic activity. Typically, the antibody or fragment is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the antibody or fragment may vary according to factors such as the disease stage, age, and weight of the patient, and the ability of the drug to elicit a desired response in the subject.

Antibodies or antigen-binding fragments thereof disclosed herein (e.g., ADI-12126 or ADI-12152) may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. An effective dose of an anti-LAG3 antibody or antigen-binding fragment thereof of the present invention, is from about 0.01 mg/kg (body weight) to about 100 mg/kg (body weight), e.g., for treatment or prevention of cancer or infectious diseases.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Guidance in selecting appropriate doses of anti-LAG3 antibodies or fragments is available (see, e.g., Wawrzynczak (1996) Antibody Therapy, *Bios Scientific Pub. Ltd*, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343:1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

Kits

Further provided are kits comprising one or more components that include, but are not limited to, an anti-LAG3 antibody or antigen-binding fragment, as discussed herein (e.g., ADI-12126 or ADI-12152) in association with one or more additional components including, but not limited to, a further therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-LAG33 antibody or antigen-binding fragment thereof of the invention (e.g., ADI-12126 or ADI-12152) or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-LAG3 antibody or antigen-binding fragment thereof of the invention (e.g., ADI-12126 or ADI-12152) or pharmaceutical composition thereof in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and the anti-LAG3 antibody or antigen-binding fragment thereof of the present invention, e.g., wherein the injection device includes the antibody or fragment or wherein the antibody or fragment is in a separate vessel.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Therapeutic Kits

As a matter of convenience, an anti-LAG3 antibody or antigen-binding fragment thereof of the invention (e.g., ADI-12126 or ADI-12152) can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-LAG3 antibody or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-LAG3 antibody or antigen-binding fragment thereof and a further therapeutic agent or a vaccine. The kit may optionally further include a syringe for parenteral, e.g., intravenous, administration. In another aspect, the kit comprises an anti-LAG3 antibody or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-LAG3 antibody or fragment. In certain embodiments, an anti-LAG3 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bispecific antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248: 1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2_{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

These examples are intended to exemplify the present invention are not a limitation thereof. Compositions and methods set forth in the Examples form part of the present invention.

Example 1: Affinity Measurements of Antibodies of the Present Invention

The affinities of the anti-LAG3 antibodies for human and cynomolgous monkey LAG3 were determined using a cell based Kinetic Exclusion Assay (KinExA). Cell based KinExA can be used to measure the affinity of a molecule for a binding partner on a cell surface (Rathanaswami et al.

Analylitical Biochemistry 373(1): 52-60 (2008); Xie et al. J. Immunol. Methods 304 (1-2): 1-14 (2005)). In this case, BaF/3 cells were stably transfected with human or cynomolgus monkey LAG3 proteins. Transfected cells or the parental BaF/3 control cell line were grown to a density of $1.7 \times 10^6$ to $3.2 \times 10^6$ cells per ml at 37° C., 120 RPM, 5% $CO_2$, in 1×RPMI 1640 media with 10% FBS, 10 ng/ml IL-3, 5 µg/ml puromycin. Cells were concentrated, mixed with 15 pM or 150 pM antibody in cell culture media and incubated 24 to 48 hours at room temperature while rotating at 20 to 30 RPM. Cells were present at a top concentration of $2 \times 10^7$ cells per ml (parental BaF/3 or cynomolgus LAG3 transfectants) or $1 \times 10^7$ cells per ml (human LAG3 transfectants) and diluted in a 2-fold, 18 member series. The cells were pelleted and free antibody in the supernatant was measured using a KinExA 3200 instrument (Sapidyne, Idaho, USA). The instrument bound the free antibody to polymethyl methacrylate beads (Sapidyne) that had been coated with goat F(ab')2 anti-human Fcγ (Jackson ImmunoResearch Laboratories, Pennsylvania, USA). Antibody on the beads was labeled with 1.5 µg/ml Alexa Fluor® 647 conjugated goat anti-human (Fab')$_2$ (Jackson ImmunoResearch Laboratories), washed and the fluorescent signal was read all using the KinExA™ 3200. The data from the 15 pM and 150 pM concentrations of each antibody were fit simultaneously using KinExA™ Pro n-Curve Analysis software version 4.0.11 (Sapidyne).

TABLE 1

Cell based Kinexa $K_D$ Determination (a) Human LAG3 affinity measurement (pM)

| mAb | Hu LAG3 $K_D$ | | | Average | ref = ADI-12126 $K_D/K_D$ ref |
|---|---|---|---|---|---|
| | n = 1 | n = 2 | n = 3 | | |
| ADI-12126 M115L | 22 | 29 | 22 | 25 | 1.1 |
| ADI-12126 M57G/M115L | 15 | 25 | 13 | 18 | 0.8 |

TABLE 1-continued

Cell based Kinexa $K_D$ Determination

| ADI-12126 M57A/M115L | 17 | 30 | 17 | 21 | 0.9 |
|---|---|---|---|---|---|
| ADI-12126 | 27 | 29 | 11 | 22 | 1.0 |

(b) Cynomolgous monkey LAG3 affinity measurement (pM)

| mAb | Cy LAG3 $K_D$ | | | Average | Cy/Hu $K_D$ Ratio | ref = ADI-12126 $K_D/K_D$ ref |
|---|---|---|---|---|---|---|
| | n = 1 | n = 2 | n = 3 | | | |
| ADI-12126 M115L | 46 | 54 | 29 | 43 | 1.7 | 0.9 |
| ADI-12126 M57G/M115L | 100 | 124 | 153 | 126 | 7.1 | 2.6 |
| ADI-12126 M57A/M115L | 554 | 163 | 385 | 367 | 17 | 7.6 |
| ADI-12126 | 37 | 60 | 48 | 48 | 2.2 | 1.0 |

The kinetic binding activity of mouse anti-human LAG3 ADI-12126 variants using human LAG3-His tagged recombinant protein was measured by surface plasmon resonance using a Biacore T200 system (Biacore, GE Healthcare, Piscataway, N.J.). Approximately 4000 RU of Goat Anti-Mouse IgG Fc gamma, Fragment Specific (Jackson ImmunoResearch Catalog #115-006-071, Lot 81313) was immobilized via amine coupling chemistry onto a Series S CM4 sensor chip, catalog number BR-1005-34. Human anti-human LAG3 clones were injected over the immobilized anti-human surfaces at 1 ug/mL for a capture level of 40 RU. HBS-EP+ buffer (BR-1006-69) was used as the running buffer with a flow rate of 30 µL/min.

Varying concentrations of human LAG3-His protein ranging from 0.15 nM to 18.8 nM, at a flow rate of 40 µL/min were injected over the antibody surfaces. Following each injection cycle, the Series S CM4 chip surface was regenerated using one six second injection of 10 mM Glycine pH 1.5 solution followed by an injection of 12.5 mM NaOH solution at a flow rate of 60 µL/min.

Background subtraction binding sensorgrams were used for analyzing the rate constant of association ($k_a$) and dissociation ($k_d$), and the equilibrium dissociation constant $K_D$. The resulting data sets were fitted with a 1:1 Langmuir Binding Model using the Biacore T200 evaluation software (version 2.0). Table 3 summarizes the affinities for the ADI-12126 antibodies to recombinant human LAG3.

TABLE 3

Biacore affinity measurement of ADI-12126 variants

| Antibody | Biacore affinity (pM) | | | Fold weaker than ADI-12126 (M57, M115) IgG4 S228P/Kappa |
|---|---|---|---|---|
| | n = 1 | n = 2 | Average | |
| ADI-12126 (M57, M115) IgG4 S228P/Kappa | 2.2 | 2.3 | 2.2 | |
| ADI-12126 (Q1E, M57G, M115L) IgG4 S228P/Kappa | 11 | 10 | 10 | 4.6 |
| ADI-12126 (Q1E, M57S, M115L) IgG4 S228P/Kappa | 134 | 119 | 127 | 5.8 |
| ADI-12126 (Q1E, M57T, M115L) IgG4 S228P/Kappa | 66 | 65 | 66 | 15 |
| ADI-12126 (Q1E, M57Y, M115L) IgG4 S228P/Kappa | 32 | 34 | 33 | 29 |
| ADI-12126 (Q1E, M57V, M115L) IgG4 S228P/Kappa | 282 | 250 | 266 | 56 |
| ADI-12126 (Q1E, M57A, M115L) IgG4 S228P/Kappa | 13 | 13 | 13 | 118 |
| ADI-12126 (Q1E, M57, M115L) IgG4 S228P/Kappa | 2.1 | 2.5 | 2.3 | about 1 |

Example 2: Jurkat Cell Activation Assay

Prepared a Raji cell suspension ($2\times10^5$ cells/ml) in RPMI media containing 10% dialyzed FBS. Incubated the Raji cells with 120 ng/ml of SED toxin for 30 minutes in a 37° C. incubator. Simultaneously incubated a cell suspension of Jurkat cells, $8\times10^6$ cells/ml (Clone G10-expressing Human LAG3 OR Mid pool-expressing cyno LAG3) with a log fold titration of (starting at 10 ug/ml) anti-LAG3 or control antibodies. Added the SED (*Staphylococcus* enterotoxin D) loaded Raji cells to the cells incubated with antibody for 24 hours in a 37° C. incubator (i.e., Raji and Jurkat cells were incubated together for 24 hours at 37° C.). Collected supernatants and analyzed using the IL2 V plex kit or a 10 plex from MSD (sandwich immunoassays which use electrochemiluminescent labels conjugated to detection antibodies (MSD=mesoscale device)).

TABLE 4

IL2 Induction of Jurkat Cells in the Presence of Anti-LAG3 Antibodies.

| Description | EC50 ng/ml in the aLag3 DT1088G10-Raji-SED assay | R-squared |
|---|---|---|
| Human x [LAG3_H] mAb (ADI-12126) IgG4 S228P/Kappa (PK) | 111.3 | 0.9808 |
| Human x [LAG3_H] mAb (ADI-12126) IgG4 S228P/Kappa (CE) | 112.5 | 0.9942 |

Example 3: Pharmacokinetics, Stability and Disposition of ADI-12126 Q1E M57G M115L Following IV Dosing in Normal Mice ADI-12126 Q1E M57G M115L is a humanized IgG4/kappa monoclonal antibody that binds to the immune checkpoint receptor lymphocyte activation gene-3 (LAG-3) and blocks interaction with its ligand, Major Histocompatibility Complex (MHC) II.

SUMMARY

The pharmacokinetics, stability, protein interactions, and biodistribution of ADI-12126 Q1E M57G M115L monoclonal antibody were characterized in normal female C57Bl/6 mice. Stability, protein interactions, and biodistribution were characterized for up to 7 days following a single intravenous dose of 3 mg/kg.

ADI-12126 Q1E M57G M115L exhibited acceptable PK in mice. The estimated Clearance (Cl) was 1.76 (ml/day/kg). The Cmax was calculated as 82.2 μg/mL with an $AUC_{0-inf}$ of 1710 (day·μg/mL). The volume of distribution at equilibrium (Vss) was 66.6 (mL/kg).

ADI-12126 Q1E M57G M115L was stable in the circulation with no detectable evidence of high molecular weight complex formation or systemic catabolism throughout the study.

ADI-12126 Q1E M57G M115L tissue-to-blood ratios were <0.53 at all collected time points indicative of a lack of tissue uptake or accumulation with an organ disposition pattern typical of normal endogenous immunoglobulin molecules.

Materials and Methods

TABLE 5

List of materials.

| Material | Vendor | Catalog no./reference |
|---|---|---|
| Amicon ® Ultra-15 centrifugal filter unit with Ultracel-10 membrane | EMD Millipore | UFC901008 |
| ACQUITY UPLC BEH200 Guard Column | Waters | 186006850 |
| ACQUITY UPLC BEH200 Column | Waters | 186006852 |
| BupH ™ borate buffer packs | Thermo Scientific | 28384 |
| CAPIJECT ® micro tube containing 0.78 mg disodium-ethylenediaminetetraacetic acid | Terumo Medical | T-MQK |
| Costar 96 well round bottom assay plate, black polystyrene | Corning Incorporated | 3792 |
| Cryolys ® cooling system | Bertin Technologies | EQ05068-200-RD000.0 |
| Dulbecco's phosphate-buffered saline | Mediatech | 21-031-CV |
| Dye removal columns and resin | Thermo Scientific | 22858 |
| DyLight ™ 650 N-hydroxysuccinimide ester | Thermo Scientific | 62265, 62266 |
| Falcon centrifuge tubes | Becton Dickinson | 352098 |
| Gel filtration standard | Bio-Rad | 151-1901 |
| Halt ™ protease inhibitor single use cocktail | Thermo Scientific | 78430, 78245 |
| Matrix storage tubes; 1.4 mL, blank polypropylene, round bottom, sterile | Thermo Scientific | 4248 |
| PreCellys ® 24 Lyzer/homogenizer | Bertin Technologies | EQ03119.200.RD000.0 |
| PreCellys ® lysing kit/tissue homogenizing CK Mix | Bertin Technologies | 03961-1-009 |
| Roche protease inhibitor cocktail | Roche | 1-697-498 |
| SecurityGuard ™ cartridges | Phenomenex | AJ0-4488 |
| Microcentrifuge tubes, polypropylene | Corning Incorporated | 430915 |
| Millex-GV syringe filter unit | EMD Millipore | SLGV033RS |
| Matrix storage tubes; 1.4 mL, blank polypropylene, round bottom, sterile | Thermo Scientific | 4248 |
| Halt protease inhibitor cocktail | Thermo Scientific | 1-697-498 |
| Slide-A-Lyzer ™ dialysis cassettes, 10K MWCO, 3 mL | Thermo Scientific | 66380 |

EDTA = ethylenediaminetetraacetic acid;
MWCO = molecular weight cutoff;
no. = number Preparation of DyLight™ 650-Labeled ADI-12126 Q1E M57G M115L DyLight™ 650 labeling kits were used to conjugate an N-hydroxysuccinimide ester fluorescence dye (excitation at 652 nm and emission at 672 nm) to ADI-12126 Q1E M57G M115L. Prior to labeling, ADI-12126 Q1E M57G M115L was buffer-exchanged to 50 mM sodium borate, 100 mM sodium chloride buffer, pH 8.5 using a 10 kilodalton (kD) molecular weight cut-off Slide-A-Lizer™ dialysis cassette. The reaction mixture contained 1.2 mg ADI-12126 Q1E M57G M115L in a final volume of 0.5 mL. The reaction was initiated by combining ADI-12126 Q1E M57G with the dye and continued for 1 hour at room temperature (RT) protected from light. Unconjugated dye was removed using a purification resin packed into spin columns. When necessary, samples were further concentrated by Amicon® ultra centrifugation filter devices with a 10 kD cut-off membrane. The labeled ADI-12126 Q1E M57G M115L was filtered using a 0.22-μm Durapore® polyvinylidene fluoride (PVDF) membrane. A NanoDrop™ apparatus (Thermo Scientific) was used to characterize the labeled reagents for determination of protein concentration and degree of labeling (DOL) as dye-to-protein, mole-to-mole ratio. The purity and integrity of the DyLight™ 650-labeled ADI-12126 Q1E M57G M115L was assessed and confirmed by size-exclusion high performance liquid chromatography (SEC-HPLC).

Preparation of ADI-12126 Q1E M57G M115L Dosing Solutions

DyLight™ 650-labeled ADI-12126 Q1E M57G M115L was stored at 4° C. protected from light prior to the preparation of the dosing solution. The degree of labeling (DOL), presented as the molar ratio of DyLight™ 650 to ADI-12126 Q1E M57G M115L, was 2.04. The dosing solution was prepared using the body weight average (18.6 grams) of the animals.

The dosing solution was prepared by diluting 0.456 mL of DyLight™ 650-labeled ADI-12126 Q1E M57G M115L (5.7 mg/mL) in 2.597 mL of Dulbecco's phosphate buffered saline (DPBS), in sterile Falcon polypropylene tubes. The final concentration of the dosing solution was 0.93 mg/mL. Sterile Lo-Dose™ U-100 insulin syringes were pre-filled with dosing solution and stored at 4° C. protected from light until time of dosing.

TABLE 6

| Test Animals. | |
|---|---|
| Species | Mouse |
| Strain | C57Bl/6 |

TABLE 6-continued

| Test Animals. | |
|---|---|
| Sex | Female |
| Source | The Jackson Laboratory |
| Number of animals used | 21 |
| Age of animals at experiment initiation | 10 weeks |

Procedures involving the care and use of animals in the study were reviewed and approved by the Institutional Animal Care and Use Committee at Merck Research Laboratories.

During the study, the care and use of animals were conducted in accordance with the principles outlined in the guidance of the Association for Assessment and Accreditation of Laboratory Animal Care (AAALAC), the Animal Welfare Act, the American Veterinary Medical Association (AVMA) Euthanasia Panel on Euthanasia, and the Institute for Laboratory Animal Research (ILAR) Guide to the Care and Use of Laboratory Animals.

Study Design/Protocol-Animal Model

One group of 21 normal, female C57Bl/6 mice were administered a single 3 mg/kg (100 μL) IV dose of DyLight™ 650-labeled ADI-12126 Q1E M57G M115L on Day 0.

Prior to dosing, a heat lamp pre-warmed the animals for several minutes. The animals were placed in an acrylic animal restrainer then, within 1 minute, the total dose volume was administered into the lateral tail vein.

TABLE 7

Group Designation, Dose Level, and Dosing Schedule.

| Group | No. of animals | Treatment | Time of dose | [1]Dose level (mg/kg) | ROA | No. of animals per time point | Time points |
|---|---|---|---|---|---|---|---|
| 1 | 21 | DyLight ™ 650-labeled ADI-12126 Q1E M57G M115L Lot number 41AJT | Day 0 | 3 | IV | 3 | 2 and 6 hours and Days 1, 2, 3, 5, and 7 |

[1]Dosing volume was 100 μL per mouse.
IV = intravenous;
No. = number;
ROA = route of administration Collection and Processing of Blood Samples Animals were euthanized by carbon dioxide inhalation and whole blood was collected from the animals via terminal cardiac puncture. Blood samples were taken at 2 and 6 hours and on Days 1, 2, 3, 5, and 7 for processing and analysis. Collected blood (~500 μL per sample) was transferred into dipotassium-ethylenediaminetetraacetic acid CapiJect micro collection tubes (TerumoMedical Corporation, Somerset, N.J.) and placed on ice. An aliquot of 100 μL of blood was pipetted into a Matrix polypropylene tube (Thermo Fisher Scientific). Plasma was obtained from remaining portion of whole blood by centrifugation at 6000×g for 6 minutes. The separated plasma was removed (~200 μL) and transferred to polypropylene vials. Plasma samples were stored at −80° C. until analysis.

Collection and Processing of Organs

Liver, kidneys, spleen, lungs, and ileum were collected for analysis at 2 hours, days 1 and 2. Organs were weighted and placed in 2 mL of PreCellys® tissue homogenizing tubes containing homogenization beads. Lysate buffer containing Halt™ protease inhibitor cocktail was added to each tube. Organ preparations were homogenized using a PreCellys® 24 instrument (Bertin Technologies) according to the manufacturer's instructions.

Assay Methods-Size-Exclusion High-Performance Liquid Chromatography Analysis of Plasma Samples Plasma samples were added to an Acquity UPLC BEH200 size-exclusion chromatography equipped with a Guard Column. An Agilent 1200 high-performance liquid chromatography (HPLC) system equipped with integrated ultraviolet (UV) (Agilent Technologies Inc.), and fluorescent detectors (Hamamatsu Corporation) was used. Molecular weight markers (Bio-Rad) were used to assess column performance prior to the analysis of plasma samples. The size exclusion procedure consisted of an 8 minute isocratic run with DPBS, in mobile phase, at a flow rate of 0.35 mL per minute. The procedure was performed at RT. The effluent was analyzed optically by fluorescent intensity at excitation and emission wavelengths of 646 and 674 nm, respectively. SEC-HPLC data was collected and analyzed with Agilent ChemStation software (Agilent Technologies, Inc.), version 2.

Analysis of Fluorescence Intensity of Blood, Plasma, and Lysate Samples

A Modulus™ microplate multimode reader (Turner Biosystems) was used to measure fluorescence intensity in blood, plasma, liver, kidney, lung, spleen and ileum lysate samples. The microplate reader was equipped with a fluorescence optical filter featuring excitation and emission wavelengths of 625 nm and 660 to 720 nm, respectively.

For pharmacokinetics, fluorescence intensity was measured in plasma at 2 and 6 hours and on days 1, 2, 3, 5, and 7. For tissue distribution, fluorescence intensity was measured in whole blood and tissue lysate samples at 2 hours and on days 2 and 5. Three fluorescence intensity calibration curves (blood, plasma, and liver lysate) were prepared to characterize the samples. The blood calibration curve was used to characterize blood, lung lysates, and spleen lysate samples. The plasma calibration curve was used to characterize plasma and ileum lysate samples. The liver calibration curve was used to characterize liver and kidney lysate samples. The tissue lysate samples were diluted to 1:10 final dilution (w/v) with tissue lysis buffer (1×DPBS with 0.1% Triton X100) for a total volume of 150 µL. Subsequently, they were transferred to a low fluorescent background, 96-well, polystyrene plates for analysis in the Modulus™ microplate multimode reader. A set of corresponding blank tissue lysates provided background correction.

Data Analyses

Fluorescence intensity data were fit using linear regression analysis in Microsoft Excel, 2010. Data from 2 animals per time point were plotted individually along with mean values. Concentrations were calculated as microgram equivalents per gram of wet tissue. Tissue-to-blood ratios were calculated using the concentration of DyLight™ 650-labeled ADI-12126 Q1E M57G M115L in tissues and blood.

Concentration-time data for ADI-12126 Q1E M57G M115L in individual plasma samples were determined using noncompartmental analysis (NCA). All pharmacokinetic (PK) parameters were estimated or calculated using Phoenix® WinNonlin software (Certara). Model 201 (IV input bolus) was used for the NCA. All concentration data and PK parameters were rounded to 3 significant FIGS.

Results

Pharmacokinetics of DyLight™ 650-Labeled ADI-12126 Q1E M57G M115L in Mice

ADI-12126 Q1E M57G M115L exhibited adequate PK in mice. The estimated Clearance (Cl) was 1.76 (ml/day/kg). The Cmax was calculated as 82.2 µg/mL with an $AUC_{0-inf}$ of 1710 (day·µg/mL). The volume of distribution at equilibrium (Vss) was 66.6 (mL/kg).

TABLE 8

PK Parameters for DyLight ™ 650-labeled ADI-12126 Q1E M57G M115L by Noncompartmental Analysis.

| $C_{max}$ (µg/mL) | $AUC_{0-inf}$ (day · µg/mL) | Cl (mL/day/kg) | $V_{ss}$ (mL/kg) | Dose (mg/kg) |
|---|---|---|---|---|
| 82.2 | 1710 | 1.76 | 66.6 | 3.0 |

All PK parameters were estimated or calculated using Phoenix ® WinNonlin (Certara). All concentration data and PK parameters were rounded to 3 significant figures.
$AUC_{0-inf}$ = area under the curve from zero up to infinite time;
Cl = clearance;
$C_{max}$ = observed maximum concentration;
IV = intravenous;
NCA = noncompartmental analysis;
PK = pharmacokinetic;
$V_{ss}$ = volume of distribution at equilibrium Systemic Stability and Protein Interactions of DyLight™ 650-Labeled ADI-12126 Q1E M57G M115L Fluorescence SEC-HPLC was used to evaluate the stability and protein interactions of DyLight™ 650-labeled ADI-12126 Q1E M57G M115L in plasma. All tested samples showed none or minimal amount of high molecular weight (HMW) complex formation. There was no evidence of degraded signal, protein interactions or catabolized DyLight™ 650-labeled ADI-12126 Q1E M57G M115L. The main chromatographic peak corresponds to intact monomeric IgG and the total amount of the intact IgG peak decreases with time due to drug clearance.

Stability and Protein Interactions of DyLight™ 650-Labeled ADI-12126 Q1E M57G M115L by SEC-HPLC Fluorescence size-exclusion high-performance liquid chromatography was used to evaluate the stability and protein interactions of DyLight™ 650-labeled ADI-12126 Q1E M57G M115L in plasma of dosed animals. Plasma samples were collected for analysis from the animals sampled at 2 and 6 hours, and on Days 1, 2, 3, 5, and 7 following a single intravenous 3 mg/kg dose of DyLight™ 650 labeled ADI-12126 Q1E M57G M115L ADI-12126 Q1E M57G M115L was stable in the circulation with no detectable evidence of high molecular weight complex formation or systemic catabolism throughout the study.

Tissue Distribution of DyLight™ 650 Labeled ADI-12126 Q1E M57G M115L

The tissue distribution of DyLight™ 650-labeled ADI-12126 Q1E M57G M115L was evaluated at 2 hours and on days 2 and 5 in liver, kidneys, lungs, spleen and ileum. A tissue-to-blood ratio >1.0 would be indicative of positive tissue uptake. Calculated tissue to blood were <0.53 for all tested tissues and time points, indicative of a negative ADI-12126 Q1E M57G M115L organ uptake or accumulation with an organ disposition pattern typical of normal endogenous immunoglobulin molecules.

TABLE 9

Average Tissue to Blood of Ratio of DL650-Human x [LAG3_H] mAb (ADI-12126 Q1E M57G M115L) IgG4.

| Time (Day) | Liver | Kidney | Lung | Spleen | Ileum | Plasma | WB |
|---|---|---|---|---|---|---|---|
| 2 hr | 0.23 | 0.23 | 0.17 | 0.37 | 0.07 | 2.09 | 1.0 |
| 2 day | 0.32 | 0.25 | 0.17 | 0.52 | 0.09 | 1.94 | 1.0 |
| 5 day | 0.34 | 0.23 | 0.19 | 0.41 | 0.08 | 2.18 | 1.0 |

DL650-Labeled ADI-12126 Q1E M57G M115L DOL = 2.04

Example 4: Characterization of Stability, Recovery and Protein Interactions of ADI-12126 Q1E M57G M115L in Human, and Cynomolgus Monkey Plasma ADI-12126 Q1E M57G M115L is a humanized IgG4/kappa monoclonal antibody that binds to the immune checkpoint receptor lymphocyte activation gene-3 (LAG-3) and blocks interaction with its ligand, Major Histocompatibility Complex (MHC) II.

SUMMARY

This study describes the stability, recovery, and potential protein interactions of ADI-12126 Q1E M57G M115L in human and cynomolgus monkey plasma after incubation for up to 14 days at 37° C.

DyLight™ 650-ADI-12126 Q1E M57G M115L was 90.6% and 90.3% stable in human and cynomolgus monkey plasma at 14 days of incubation. The recovery of the DyLight™ 650-labeled ADI-12126 Q1E M57G was >89% in human and cynomolgus monkey plasma at 14 days of incubation. Accordingly, only minimal levels of high molecular weight complexes and loss of the fluorescent moiety were observed in both biomatrices over the 14 day time course.

Materials & Methods

Source of Plasma

Pooled human, and cynomolgus monkey plasma containing dipotassium ethylenediaminetetraacetic acid was obtained from Bioreclamation Inc. Plasma was transported to Merck Research Laboratories (Palo Alto, Calif., USA) on dry ice and stored at −80° C. until use.

Preparation of DyLight™ 650-Labeled ADI-12126 Q1E M57G M115L

ADI-12126 Q1E M57G M115L was labeled as described before in the Pharmacokinetics, stability and disposition study. The purity and integrity of the DyLight™ 650-labeled ADI-12126 Q1E M57G M115L used in this study was assessed and confirmed by size-exclusion high performance liquid chromatography (SEC-HPLC). The degree of labeling (DOL) was 3.1.

Assessment of DyLight™ 650-Labeled ADI-12126 Q1E M57G M115L Stability, Recovery, and Interactions in Plasma DyLight™ 650-labeled ADI-12126 Q1E M57G M115L (at a final concentration of 200 μg/mL) was incubated with neat, pooled human, or cynomolgus monkey plasma containing dipotassium ethylenediaminetetraacetic acid at 37° C.

Aliquots of plasma (100 μL) were collected after 0, 2 hours and 1, 2, 4, 7, 10 and 14 days of incubation with DyLight™ 650-labeled ADI-12126 Q1E M57G M115L, snap frozen, and stored at −80° C. until use. Each sample was diluted 1:10 in DPBS (final concentration of 20 μg/mL DyLight™ 650-labeled ADI-12126 Q1E M57G M115L) and analyzed by size-exclusion high-performance liquid chromatography (SEC-HPLC).

Size-Exclusion High-Performance Liquid Chromatography

Samples were applied onto an Acquity UPLC Protein BEH SEC column (200A, 1.7 um, 4.6 mm×150 mm). The samples were separated using an Agilent 1260 high-performance liquid chromatography (HPLC) system equipped with a diode array detector, ultraviolet-visible (UV-Vis) spectroscopy (Agilent Technologies Inc.), and fluorescent detector (Hamamatsu Photonics K.K).

The size-exclusion procedure was an 8 minute isocratic run with DPBS as mobile phase at a flow rate of 0.35 mL per minute at room temperature. The effluent was monitored optically by total fluorescent intensity at excitation and emission of 646 and 674 nm, respectively. Data collection and analysis were performed using the Agilent ChemStation software V2 (Agilent Technologies Inc.). Molecular weight markers were run before analysis of experimental samples for assessment of column performance.

Data Analysis

The main peak and all other detectable peak areas detected by SEC-HPLC were integrated. Stability of DyLight™ 650-labeled ADI-12126 Q1E M57G M115L was calculated as the percent of intact monomeric IgG peak area relative to the total fluorescence area in each chromatogram. The recovery of DyLight™ 650-labeled ADI-12126 Q1E M57G M115L was calculated as the percent of the intact monomeric IgG peak at each sequential time point relative to the initial incubation time point (time 0).

Results

Stability, Recovery, and Interactions of DyLight™ 650-Labeled ADI-12126 Q1E M57G M115L in Plasma from Humans, and Cynomolgus Monkeys DyLight™ 650-ADI-12126 Q1E M57G M115L was 90.6% and 90.3% stable in human and cynomolgus monkey plasma at 14 days of incubation. The recovery of the DyLight™ 650-labeled ADI-12126 Q1E M57G was >89% in human and cynomolgus monkey plasma at 14 days of incubation. Accordingly, only minimal levels of high molecular weight complexes and loss of the fluorescent moiety were observed in all both biomatrices over the 14 day time course.

TABLE 10

Stability and Recovery of DyLight ™ 650-labeled ADI-12126 Q1E M57G M115L in Human, and Cynomolgus Monkey Plasma.

| | Human plasma | | Cynomolgus Monkey plasma | |
|---|---|---|---|---|
| Time point (Day) | [1] Stability (% total peak area) | [2] Recovery (% of time 0) | [1] Stability (% total peak area) | [2] Recovery (% of time 0) |
| 0 | 94.8 | 100.0 | 96.3 | 100.0 |
| 0.083 (2 h) | 93.4 | 98.1 | 92.9 | 101.1 |
| 1 Days | 93.2 | 102.4 | 92.7 | 94.4 |
| 2 Days | 92.7 | 103.5 | 92.4 | 87.5 |
| 4 Days | 92.3 | 106.1 | 91.8 | 91.9 |
| 7 Days | 91.9 | 101.8 | 91.3 | 91.0 |
| 10 Days | 91.3 | 103.4 | 90.8 | 90.6 |
| 14 Days | 90.6 | 101.5 | 90.3 | 89.7 |

DyLight ™ 650-labeled ADI-12126 Q1E M57G M115L was incubated in neat, pooled human, or cynomolgus monkey plasma for up to 14 days at 37° C.
[1] The stability of DyLight ™ 650-labeled ADI-12126 Q1E M57G M115L was calculated as the percent of intact monomeric IgG peak area relative to the total fluorescent area in each chromatogram.
[2] The recovery of DyLight ™ 650-labeled ADI-12126 Q1E M57G M115L was calculated as the percent of the intact monomeric IgG peak at each sequential time point relative to the initial incubation time point (Time 0).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

We claim:

1. An antibody or antigen-binding fragment thereof that specifically binds human LAG3 of SEQ ID NO: 53 comprising:
    (a) the CDR1, CDR2, and CDR3 of a $V_L$ region of an immunoglobulin chain that comprises the amino acid sequence set forth in SEQ ID NO: 2 or 4; and
    (b) the CDR1, CDR2, and CDR3 of a $V_H$ region of an immunoglobulin chain that comprises the amino acid sequence set forth in SEQ ID NO: 1 or 3.

2. The antibody or fragment of claim 1 comprising:
    a light chain variable domain comprising:
    CDR-L1 that comprises the amino acid sequence in SEQ ID NO: 8;
    CDR-L2 that comprises the amino acid sequence in SEQ ID NO: 9; and
    CDR-L3 that comprises the amino acid sequence: in SEQ ID NO: 10; and
    a heavy chain variable domain comprising:
    CDR-H1 that comprises the amino acid sequence in SEQ ID NO: 5;
    CDR-H2 that comprises the amino acid sequence in SEQ ID NO: 6; and
    CDR-H3 that comprises the amino acid sequence in SEQ ID NO: 7.

3. The antibody or antigen-binding fragment of claim 1 comprising:
    a light chain variable region comprising: CDR-L1 that comprises the amino acid sequence in SEQ ID NO: 14; CDR-L2 that comprises the amino acid sequence in SEQ ID NO: 15; and CDR-L3 that comprises the amino acid sequence in SEQ ID NO: 16; and a heavy chain variable region comprising: CDR-H1 that comprises the amino acid sequence in SEQ ID NO: 11; CDR-H2 that comprises the amino acid sequence in SEQ ID NO: 12; and CDR-H3 that comprises the amino acid sequence in SEQ ID NO: 13.

4. The antibody or antigen-binding fragment of claim 1 comprising:
    (1)
    a light chain immunoglobulin comprising CDR-L1, CDR-L2 and CDR-L3 of the immunoglobulin comprising the amino acid sequence of SEQ ID NO: 2, and having at least 90% amino acid sequence identity to the amino acid sequence set forth in SEQ ID NO: 2; and a heavy chain immunoglobulin comprising CDR-H1, CDR-H2 and CDR-H3 of the immunoglobulin comprising the amino acid sequence of SEQ ID NO: 1, and having at least 90% amino acid sequence identity to the amino acid sequence set forth in SEQ ID NO: 1; or
    (2)
    a light chain immunoglobulin comprising CDR-L1, CDR-L2 and CDR-L3 of the immunoglobulin comprising the amino acid sequence of SEQ ID NO: 4, and having at least 90% amino acid sequence identity to the amino acid sequence set forth in SEQ ID NO: 4; and a heavy chain immunoglobulin comprising CDR-H1, CDR-H2 and CDR-H3 of the immunoglobulin comprising the amino acid sequence of SEQ ID NO: 3, and having at least 90% amino acid sequence identity to the amino acid sequence set forth in SEQ ID NO: 3.

5. The antibody or antigen-binding fragment of claim 4 wherein said sequence identity is at least 95%, 96%, 97%, 98%, 99% or 100%.

6. The antibody or antigen-binding fragment of claim 5 comprising:
    (1)
    a light chain immunoglobulin comprising the amino acid sequence set forth in SEQ ID NO: 2; and
    a heavy chain immunoglobulin comprising the amino acid sequence set forth in SEQ ID NO: 1; or
    (2)
    a light chain immunoglobulin comprising the amino acid sequence set forth in SEQ ID NO: 4; and
    a heavy chain immunoglobulin comprising the amino acid sequence set forth in SEQ ID NO: 3; or
    (3)
    a light chain immunoglobulin comprising the amino acid sequence set forth in SEQ ID NO: 22; and
    a heavy chain immunoglobulin comprising the amino acid sequence set forth in SEQ ID NO: 21; or
    (4)
    a light chain immunoglobulin comprising the amino acid sequence set forth in SEQ ID NO: 24; and
    a heavy chain immunoglobulin comprising the amino acid sequence set forth in SEQ ID NO: 23.

7. The antibody or fragment of claim 6 which is glycosylated with engineered yeast N-linked glycans or CHO N-linked glycans.

8. The antibody or fragment of claim 6 which is an antibody.

9. The antibody or antigen-binding fragment of claim 5 comprising:
    a light chain variable region comprising the amino acid sequence set forth in SEQ ID NO: 4; and
    a heavy chain variable region comprising the amino acid sequence set forth in SEQ ID NO: 3.

10. The antibody of claim 5 comprising:
    a light chain immunoglobulin comprising the amino acid sequence set forth in SEQ ID NO: 24;
    and a heavy chain immunoglobulin comprising the amino acid sequence set forth in SEQ ID NO: 23.

11. A composition or kit comprising the antibody, or antigen-binding fragment, of claim 1 and, optionally, a pharmaceutically acceptable carrier or diluent; which is optionally in association with a further therapeutic agent.

12. The composition or kit of claim 11 wherein the further therapeutic agent is an anti-PD-1 antibody.

13. An antibody or antigen-binding fragment thereof that specifically binds human LAG3 of SEQ ID NO: 53 comprising a light chain variable region comprising an amino acid sequence set forth in SEQ ID NO: 2, and a heavy chain variable region comprising an amino acid sequence set forth in SEQ ID NO: 1, wherein $X_1$=E, $X_2$=G and $X_3$=L; $X_1$=Q, $X_2$=M and $X_3$=M; $X_1$=E, $X_2$=A and $X_3$=L; or $X_1$=E, $X_2$=M and $X_3$=L.

14. The antibody or antigen-binding fragment thereof of claim 13 comprising:
a light chain variable region comprising an amino acid sequence set forth in SEQ ID NO: 2, and a heavy chain variable region comprising an amino acid sequence set forth in SEQ ID NO: 1, wherein $X_1$=E, $X_2$=G and $X_3$=L.

15. The antibody of claim 13 comprising: a light chain immunoglobulin comprising the amino acid sequence set forth in SEQ ID NO: 22; and a heavy chain immunoglobulin comprising the amino acid sequence set forth in SEQ ID NO: 21; wherein $X_1$=E, $X_2$=G and $X_3$=L.

16. The antibody of claim 13 comprising: a light chain immunoglobulin comprising an amino acid sequence set forth in SEQ ID NO: 22, and a heavy chain immunoglobulin comprising an amino acid sequence set forth in SEQ ID NO: 21, wherein $X_1$=Q, $X_2$=M and $X_3$=M.

17. The antibody of claim 13 comprising: a light chain immunoglobulin comprising an amino acid sequence set forth in SEQ ID NO: 22, and a heavy chain immunoglobulin comprising an amino acid sequence set forth in SEQ ID NO:21, wherein $X_1$=E, $X_2$=A and $X_3$=L.

18. The antibody of claim 13 comprising: a light chain immunoglobulin comprising an amino acid sequence set forth in SEQ ID NO: 22, and a heavy chain immunoglobulin comprising an amino acid sequence set forth in SEQ ID NO: 21, wherein $X_1$=E, $X_2$=M and $X_3$=L.

* * * * *